(12) United States Patent
Ross et al.

(10) Patent No.: US 8,806,973 B2
(45) Date of Patent: Aug. 19, 2014

(54) ADAPTERS FOR USE BETWEEN SURGICAL HANDLE ASSEMBLY AND SURGICAL END EFFECTOR

(75) Inventors: Adam J. Ross, Prospect, CT (US); John W. Beardsley, Wallingford, CT (US); Peter Datcuk, Quakerstown, PA (US); Michael A. Zemlok, Prospect, CT (US); Teddy R. Bryant, Branford, CT (US)

(73) Assignee: Covidien LP, Mansfield, MA (US)

( * ) Notice: Subject to any disclaimer, the term of this patent is extended or adjusted under 35 U.S.C. 154(b) by 166 days.

(21) Appl. No.: 12/946,082

(22) Filed: Nov. 15, 2010

(65) Prior Publication Data

US 2011/0174099 A1 Jul. 21, 2011

Related U.S. Application Data

(60) Provisional application No. 61/308,045, filed on Feb. 25, 2010, provisional application No. 61/265,942, filed on Dec. 2, 2009.

(51) Int. Cl.
*F16H 25/12* (2006.01)
*A61B 17/00* (2006.01)

(52) U.S. Cl.
CPC ....... *A61B 17/00* (2013.01); *A61B 2017/00464* (2013.01)
USPC .............................................. 74/89.32; 74/89

(58) Field of Classification Search
CPC ........... A61B 2017/00477; A61B 2017/00398; A61B 2017/00017; A61B 2017/00464
See application file for complete search history.

(56) References Cited

U.S. PATENT DOCUMENTS

| 6,817,508 | B1 | 11/2004 | Racenet et al. |
| 7,147,138 | B2 | 12/2006 | Shelton |
| 7,947,034 | B2 | 5/2011 | Whitman |
| 8,114,118 | B2 | 2/2012 | Knodel et al. |
| 8,182,494 | B1 | 5/2012 | Yencho et al. |
| 8,292,150 | B2 | 10/2012 | Bryant |
| 8,517,241 | B2 | 8/2013 | Nicholas et al. |
| 2003/0130677 | A1 | 7/2003 | Whitman et al. |
| 2005/0125027 | A1 | 6/2005 | Knodel et al. |
| 2005/0131442 | A1* | 6/2005 | Yachia et al. ................. 606/185 |
| 2007/0016067 | A1* | 1/2007 | Webster et al. ............... 600/464 |
| 2007/0055219 | A1 | 3/2007 | Whitman et al. |

(Continued)

FOREIGN PATENT DOCUMENTS

| CA | 2451558 | 1/2003 |
| CN | 102 247 182 | 11/2011 |

(Continued)

OTHER PUBLICATIONS

European Search Report for EP 10252037.6-1269 date of completion is Mar. 1, 2011 (3 pages).

(Continued)

*Primary Examiner* — Gary Jackson
*Assistant Examiner* — Scott T Luan

(57) ABSTRACT

Adapter assemblies are provided for selectively interconnecting a surgical end effector that is configured to perform at least a pair of functions and a surgical device that is configured to actuate the end effector, wherein the end effector includes a first axially translatable drive member and a second axially translatable drive member, and wherein the surgical device includes a first rotatable drive shaft and a second rotatable drive shaft.

14 Claims, 54 Drawing Sheets

(56) References Cited

U.S. PATENT DOCUMENTS

| | | | |
|---|---|---|---|
| 2008/0255413 A1* | 10/2008 | Zemlok et al. | 600/106 |
| 2009/0090763 A1 | 4/2009 | Zemlok et al. | |
| 2009/0145947 A1 | 6/2009 | Scirica et al. | |
| 2009/0179063 A1 | 7/2009 | Milliman et al. | |
| 2009/0254094 A1 | 10/2009 | Knapp et al. | |
| 2010/0225073 A1 | 9/2010 | Porter et al. | |
| 2011/0125138 A1 | 5/2011 | Malinouskas et al. | |
| 2011/0174099 A1 | 7/2011 | Ross et al. | |
| 2011/0290854 A1 | 12/2011 | Timm et al. | |
| 2011/0295242 A1 | 12/2011 | Spivey et al. | |
| 2011/0295269 A1 | 12/2011 | Swensgard et al. | |
| 2012/0000962 A1 | 1/2012 | Racenet et al. | |
| 2012/0089131 A1 | 4/2012 | Zemlok et al. | |
| 2012/0253329 A1 | 10/2012 | Zemlok et al. | |
| 2012/0310220 A1 | 12/2012 | Malkowski et al. | |
| 2012/0323226 A1 | 12/2012 | Chowaniec et al. | |
| 2013/0018361 A1 | 1/2013 | Bryant | |
| 2013/0098966 A1 | 4/2013 | Kostrzewski et al. | |
| 2013/0098968 A1 | 4/2013 | Aranyi et al. | |
| 2013/0098969 A1 | 4/2013 | Scirica et al. | |
| 2013/0214025 A1 | 8/2013 | Zemlok et al. | |
| 2013/0240596 A1 | 9/2013 | Whitman | |
| 2013/0274722 A1 | 10/2013 | Kostrzewski et al. | |

FOREIGN PATENT DOCUMENTS

| | | |
|---|---|---|
| EP | 0 634 144 | 1/1995 |
| EP | 0634144 A1 | 1/1995 |
| EP | 1813199 | 8/2007 |
| EP | 1813211 | 8/2007 |
| EP | 2 005 898 | 12/2008 |
| EP | 2 005 898 A2 | 12/2008 |
| EP | 2 098 170 | 9/2009 |
| EP | 2098170 A2 | 9/2009 |
| EP | 2236098 | 10/2010 |
| EP | 2263568 | 12/2010 |
| EP | 2329773 | 6/2011 |
| EP | 2586382 | 5/2013 |
| EP | 2606834 | 6/2013 |
| WO | WO 03/000138 | 1/2003 |
| WO | WO 2007/014355 | 2/2007 |
| WO | WO2007/014355 A2 | 2/2007 |
| WO | WO 2009/039506 A1 | 3/2009 |
| WO | WO 2011/108840 | 9/2011 |

OTHER PUBLICATIONS

Extended European Search Report corresponding to EP 13 17 5377.4, completed Jul. 30, 2013, and mailed Aug. 6, 2013; (5 pp).
Extended European Search Report corresponding to EP No. 11 17 8021.9, mailed Jun. 4, 2013; (3 pp).
Extended European Search Report corresponding to EP No. 13 16 3033.7, completed Jun. 27, 2013; (8 pp).
Extended European Search Report corresponding to EP No. 12 18 6177.7, completed Aug. 14, 2013 and mailed Aug. 23, 2013; (8 pp).
Partial European Search Report corresponding to EP No. 13 17 1742.3, completed Sep. 17, 2013 and mailed Sep. 25, 2013; (8 pp).
Partial European Search Report corresponding to EP No. 13 17 2400.7, completed Sep. 18, 2013 and mailed Oct. 1, 2013; (7 pp).
Extended European Search Report corresponding to EP No. 13 17 5475.6, completed Sep. 23, 2013 and mailed Oct. 1, 2013; (8 pp).
Extended European Search Report corresponding to EP No. 13 17 5478.0, completed Sep. 24, 2013 and mailed Oct. 2, 2013; (6 pp).
Extended European Search Report corresponding to EP No. 13 17 5479.8, completed Sep. 27, 2013 and mailed Oct. 10, 2013; (7 pp).
Partial Extended European Search Report corresponding to EP 13 17 5477.2, completed Oct. 7, 2013 and mailed Oct. 15, 2013; (7 pp).
Extended European Search Report corresponding to EP No. 08 25 2703.7, completed Oct. 23, 2008 and mailed Oct. 31, 2008; (7 pp).
European Search Report corresponding to European Application EP 13 17 5479.8, mailed on Oct. 10, 2013; 7 pages.

\* cited by examiner

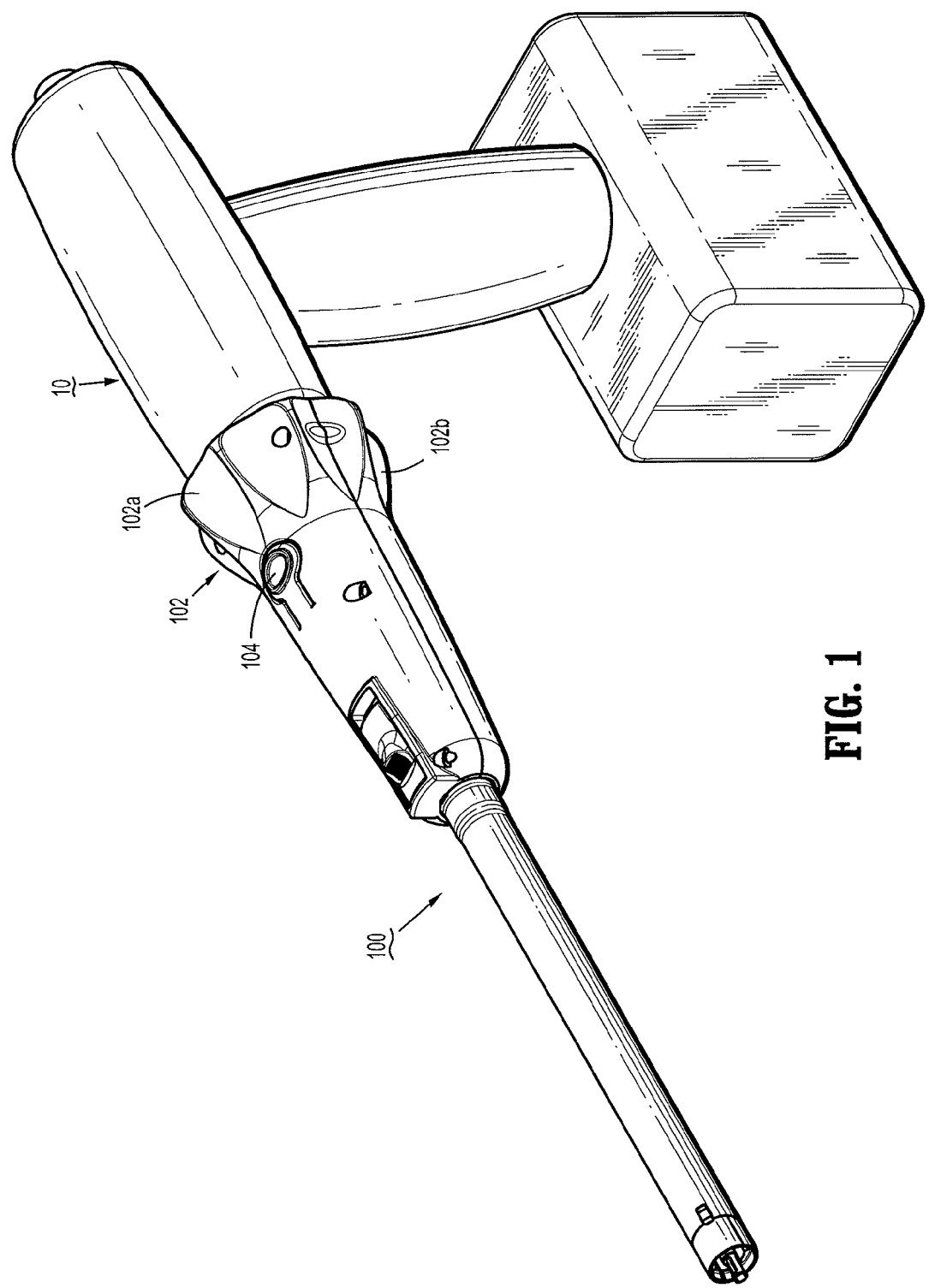

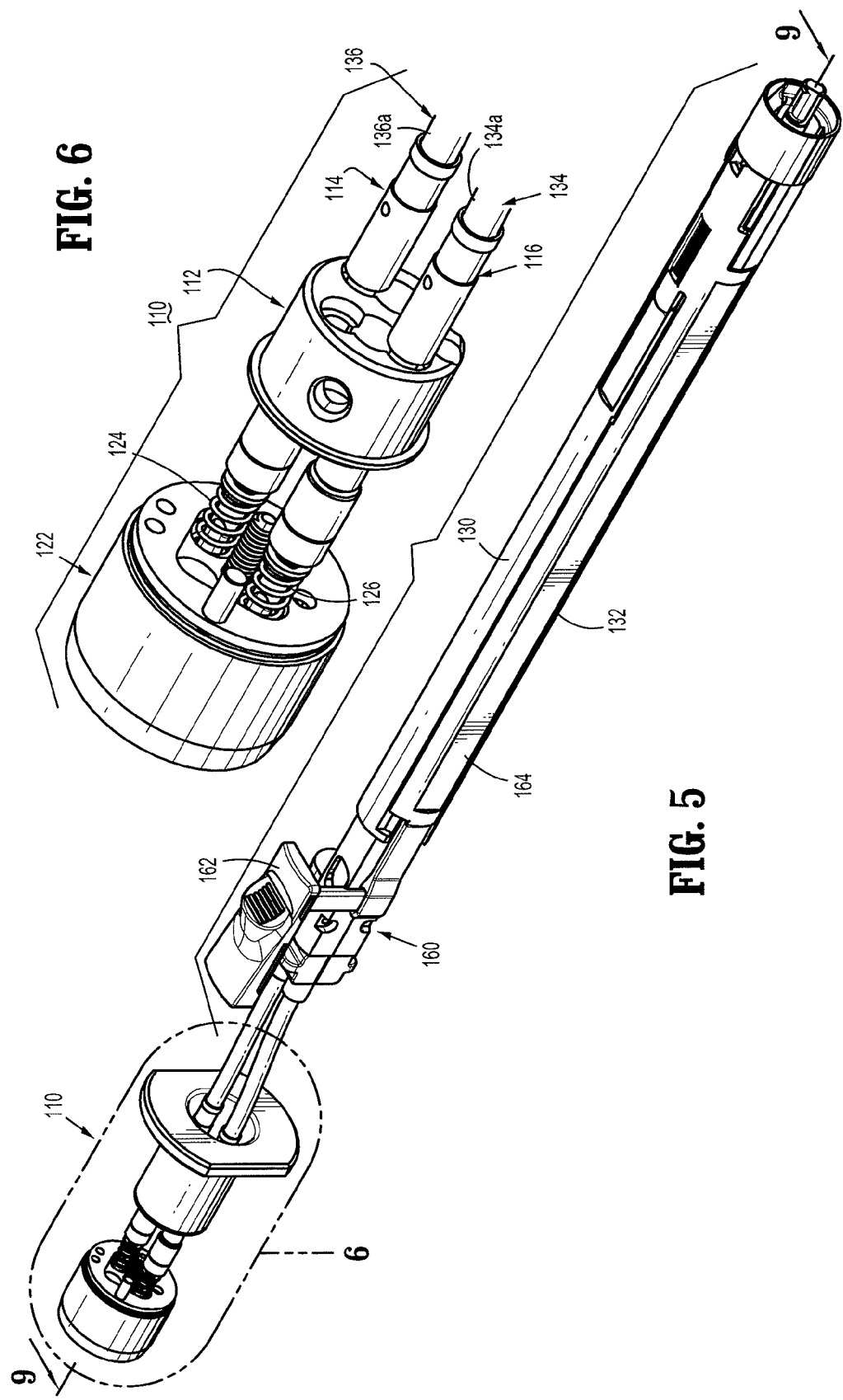

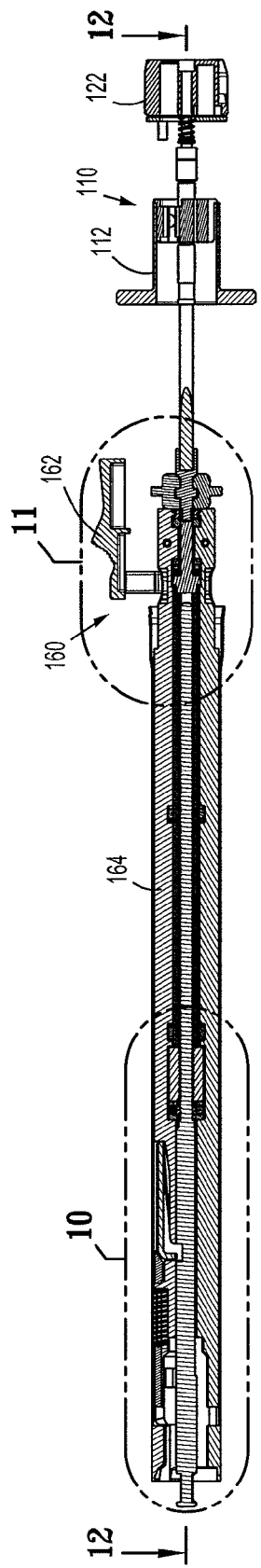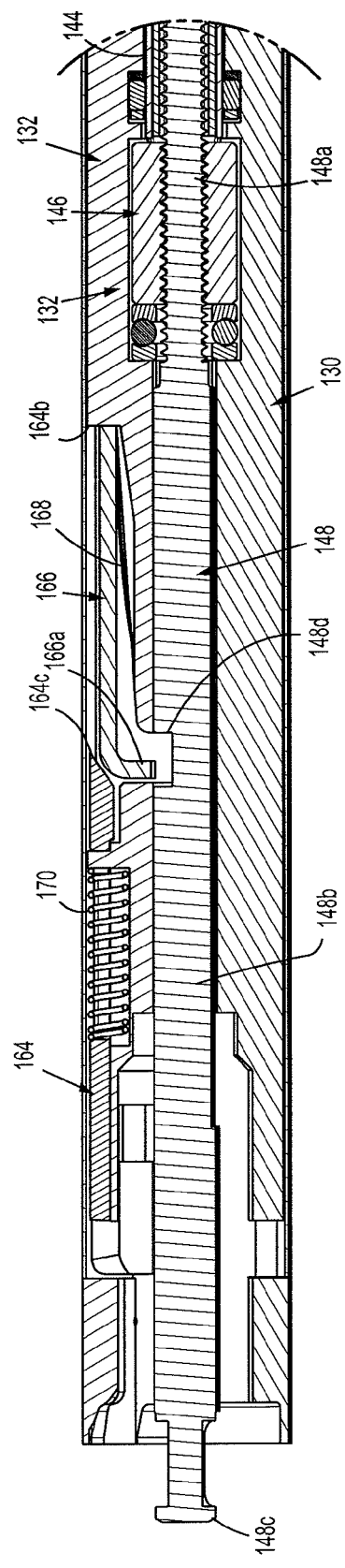
FIG. 9
FIG. 10

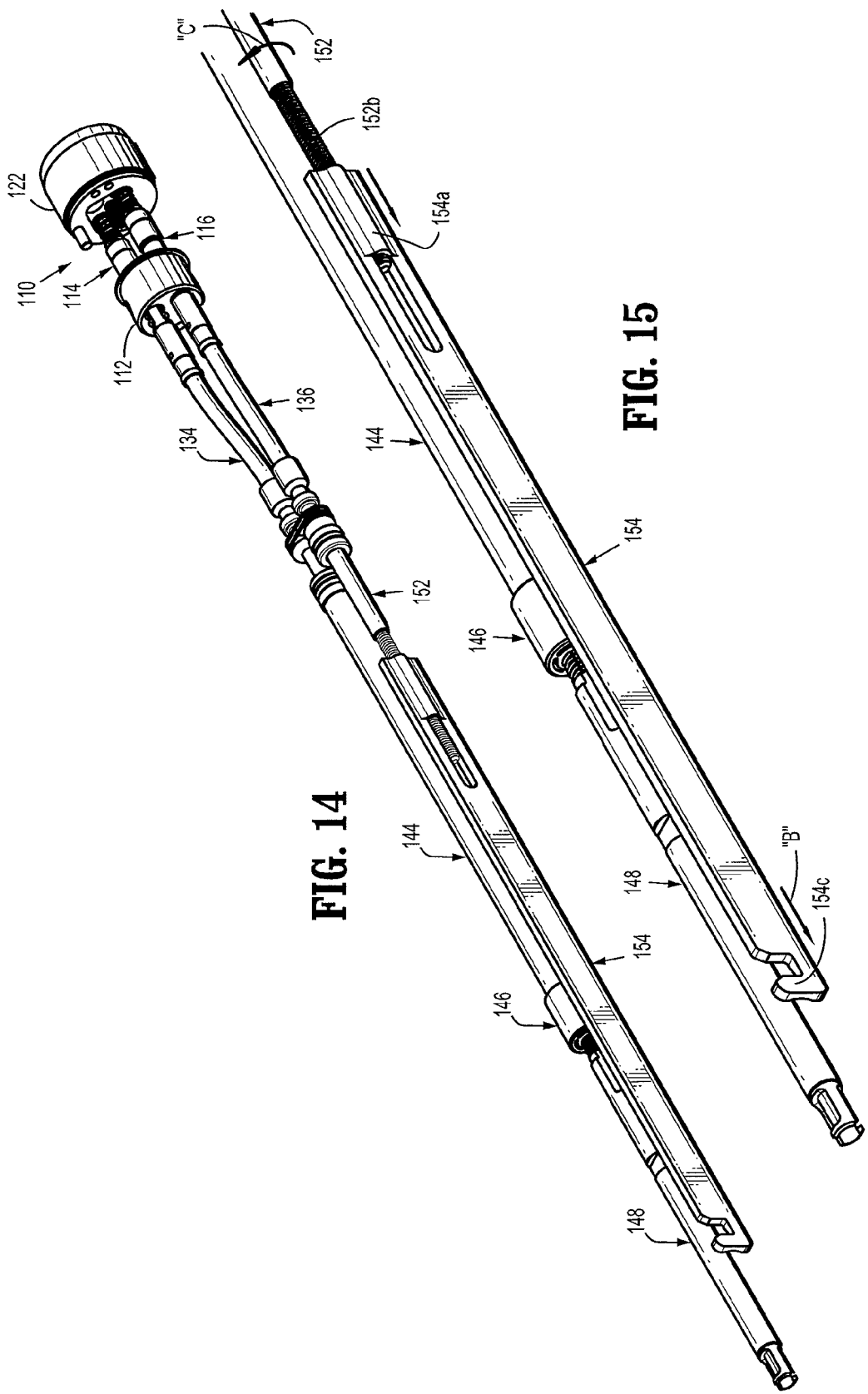

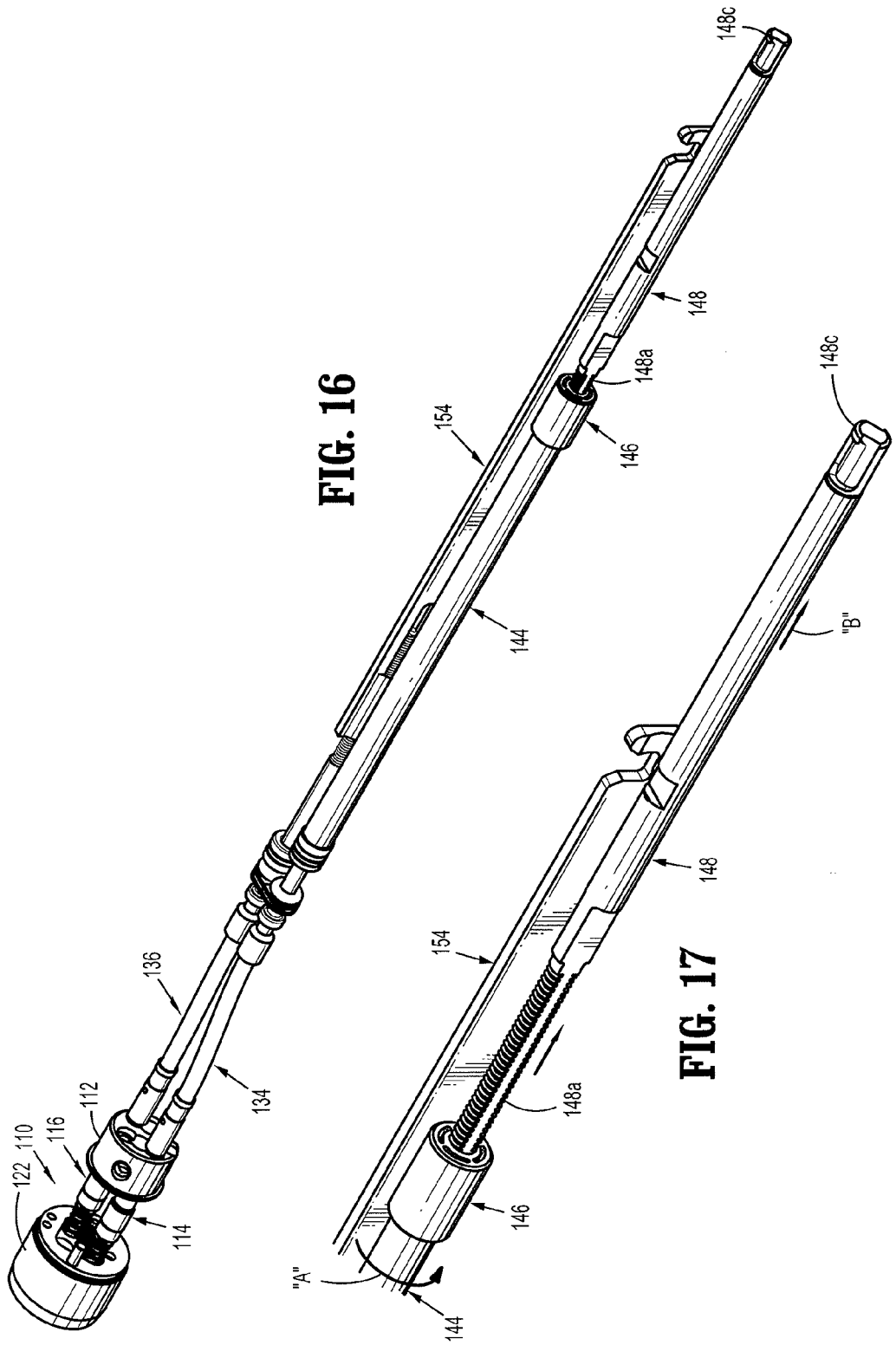

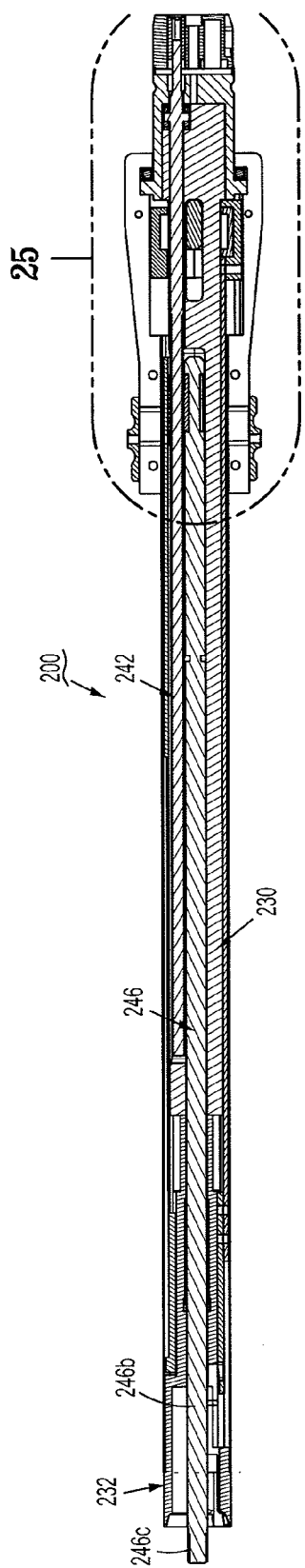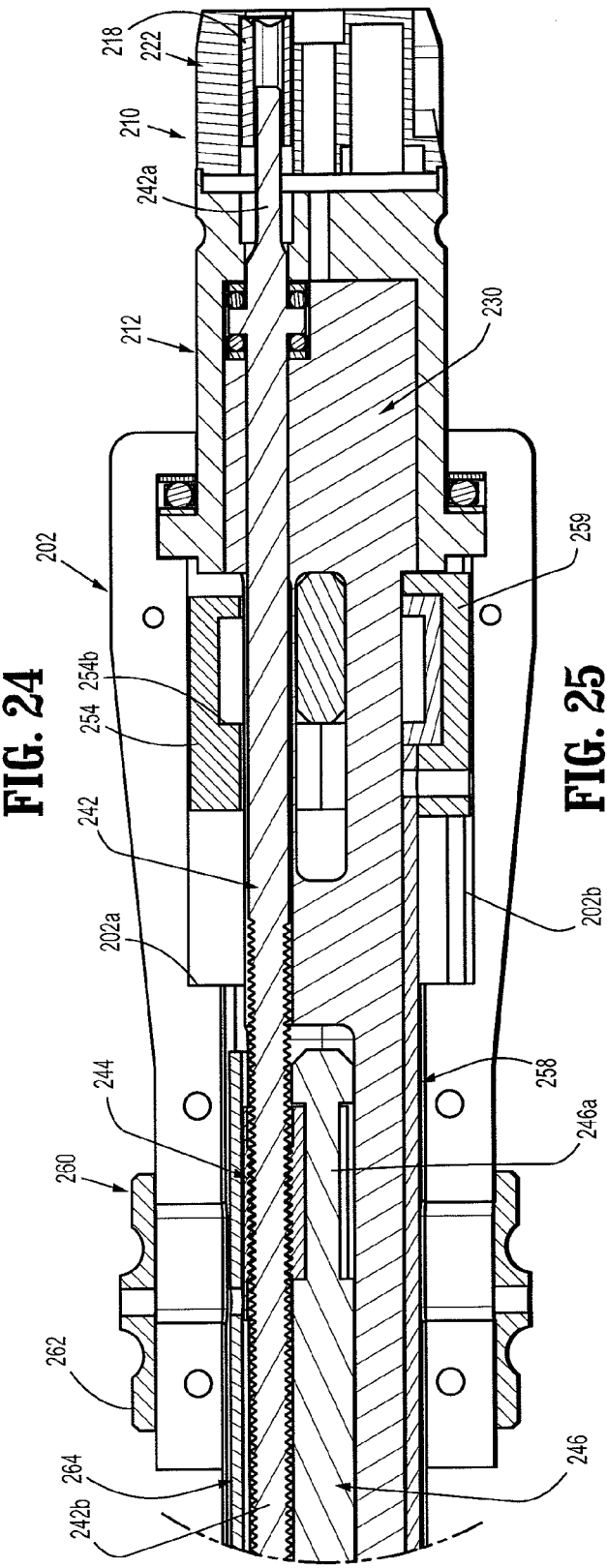

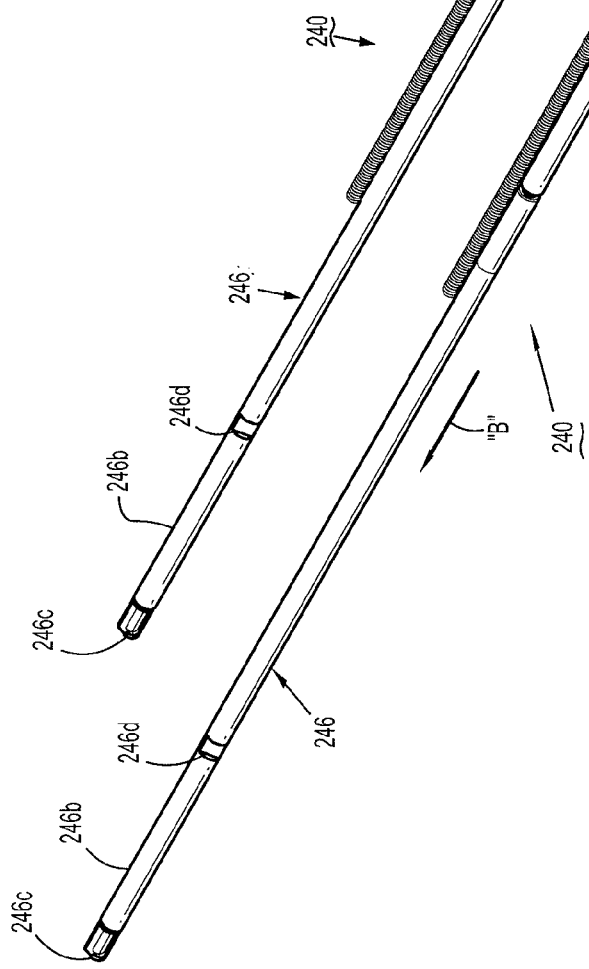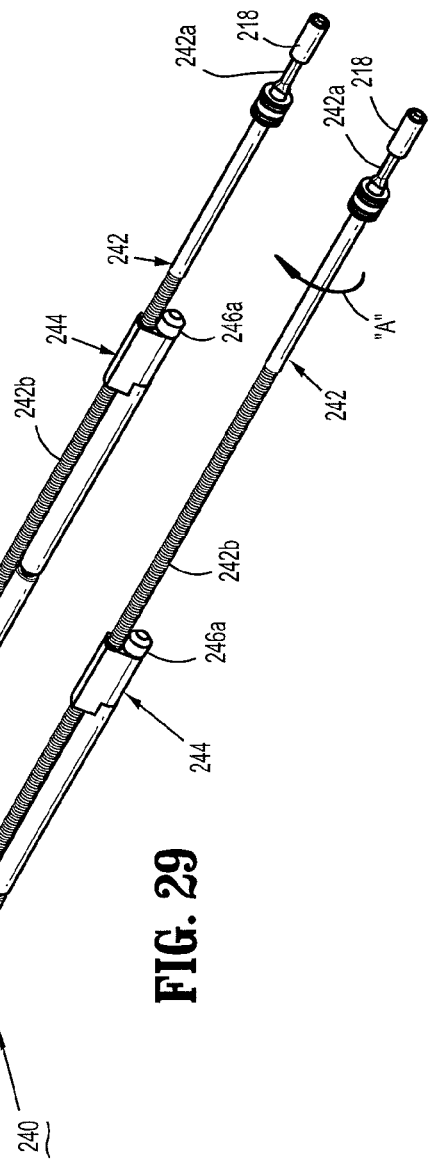

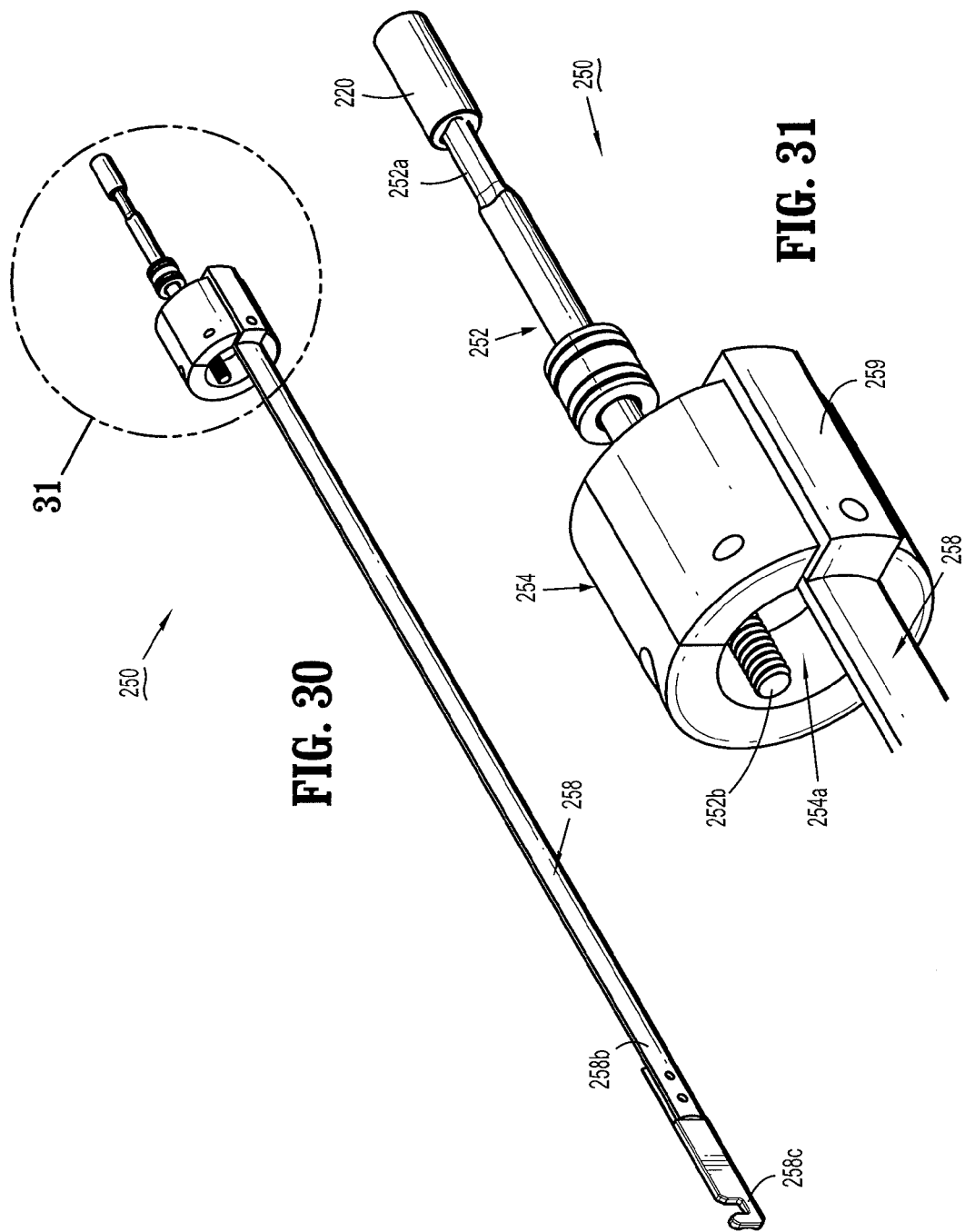

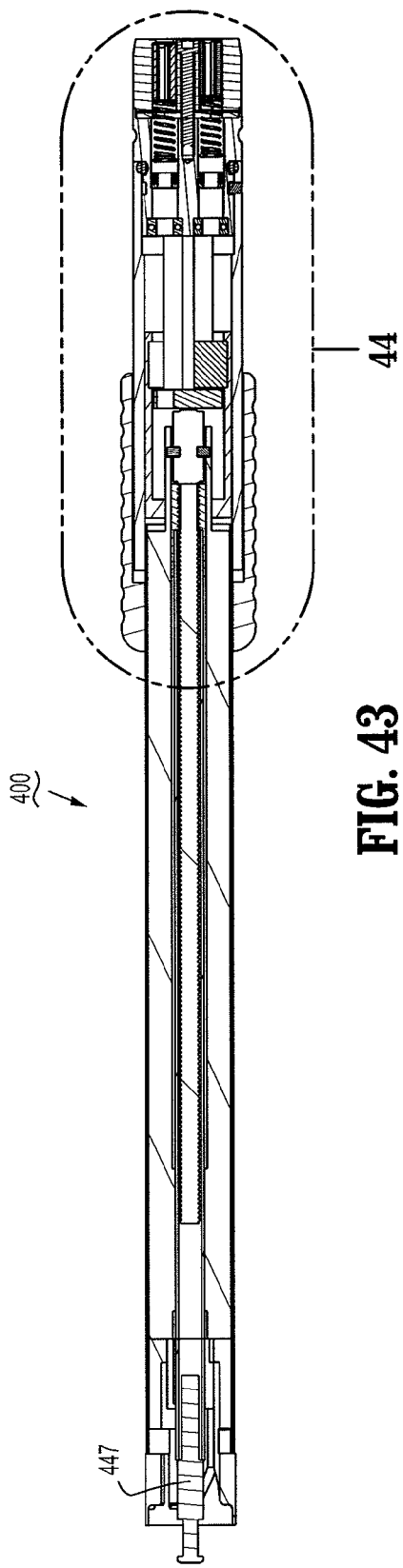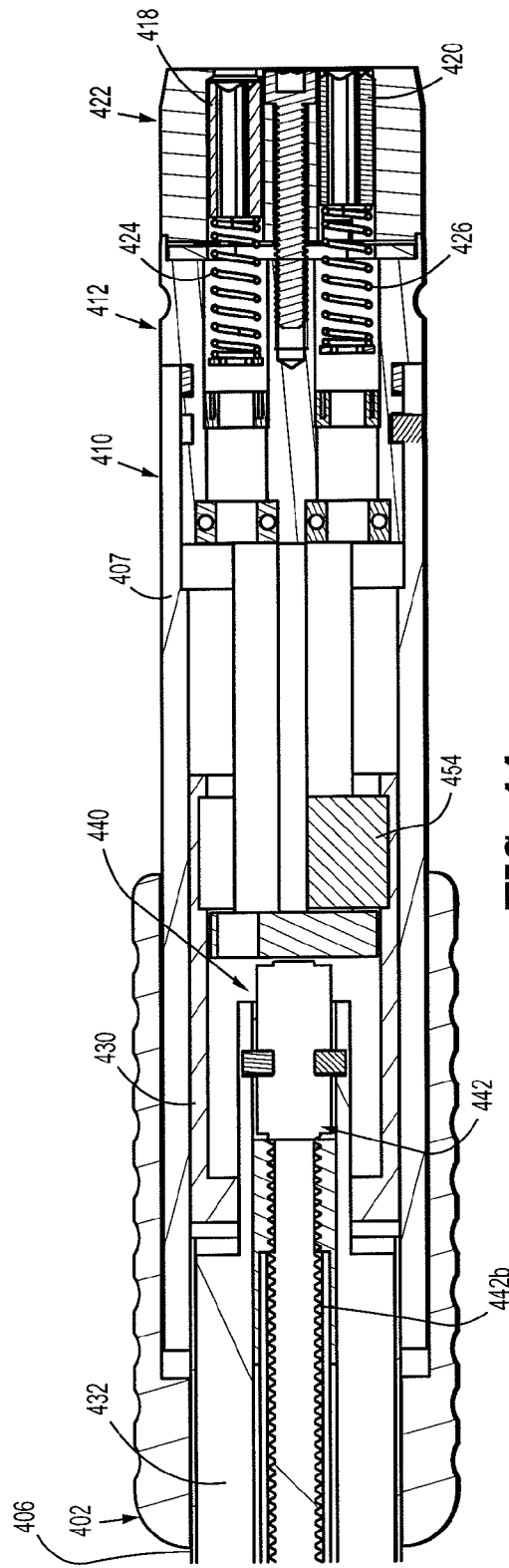
FIG. 43
FIG. 44

ADAPTERS FOR USE BETWEEN SURGICAL HANDLE ASSEMBLY AND SURGICAL END EFFECTOR

CROSS REFERENCE TO RELATED APPLICATION

The present application claims the benefit of and priority to each of U.S. Provisional Application Ser. No. 61/308,045, filed on Feb. 25, 2010, and U.S. Provisional Application Ser. No. 61/265,942, filed on Dec. 2, 2009, the entire content of each of which being incorporate herein by reference.

BACKGROUND

1. Technical Field

The present disclosure relates to adapters used for surgical devices and/or systems. More specifically, the present disclosure relates to adapters and/or adapter assemblies for use between and for interconnecting a powered, rotating and/or articulating surgical device or handle assembly and an end effector for clamping, cutting and/or stapling tissue.

2. Background of Related Art

A number of surgical device manufacturers have developed product lines with proprietary drive systems for operating and/or manipulating the surgical device. In many instances the surgical devices include a handle assembly, which is reusable, and a disposable end effector or the like that is selectively connected to the handle assembly prior to use and then disconnected from the end effector following use in order to be disposed of or in some instances sterilized for re-use.

Many of the existing end effectors for use with many of the existing surgical devices and/or handle assemblies are driven by a linear force. For examples, end effectors for performing endo-gastrointestinal anastomosis procedures, end-to-end anastomosis procedures and transverse anastomosis procedures, each typically require a linear driving force in order to be operated. As such, these end effectors are not compatible with surgical devices and/or handle assemblies that use a rotary motion to deliver power or the like.

In order to make the linear driven end effectors compatible with surgical devices and/or handle assemblies that use a rotary motion to deliver power, a need exists for adapters and/or adapter assemblies to interface between and interconnect the linear driven end effectors with the rotary driven surgical devices and/or handle assemblies.

BRIEF DESCRIPTION OF THE DRAWINGS

Embodiments of the present disclosure are described herein with reference to the accompanying drawings, wherein:

FIG. 1 is a perspective view of an exemplary surgical device and/or handle assembly supporting an adapter assembly according to an embodiment of the present disclosure;

FIG. 5 is a perspective view of the adapter assembly of FIGS. 1-4, illustrated with the outer tube and the knob housing removed therefrom;

FIG. 6 is an enlarged perspective view of the indicated area of detail of FIG. 5;

FIG. 9 is a longitudinal, cross-sectional view as taken through 9-9 of FIG. 5;

FIG. 10 is an enlarged view of the indicated area of detail of FIG. 9;

FIG. 14 is a right side, perspective view of a first and second drive converter of the adapter assembly of FIGS. 1-13;

FIG. 15 is an enlarged perspective view of a distal end of the first and second drive converters of the adapter assembly of FIGS. 1-14, illustrating an operation of the first drive converter;

FIG. 16 is a left side, perspective view of the first and second drive converter of the adapter assembly of FIGS. 1-13;

FIG. 17 is an enlarged perspective view of a distal end of the first and second drive converters of the adapter assembly of FIGS. 1-14, illustrating an operation of the second drive converter;

FIG. 24 is a longitudinal, cross-sectional view of the adapter assembly of FIGS. 18-22, as taken through 24-24 of FIG. 18;

FIG. 25 is an enlarged view of the indicated area of detail of FIG. 24;

FIG. 28 is a rear, perspective view of a first drive assembly of the adapter assembly of FIGS. 18-27, shown in a first condition;

FIG. 29 is a rear, perspective view of the first drive assembly of FIG. 28, illustrating an operation thereof;

FIG. 30 is a perspective view of a second drive assembly of the adapter assembly of FIGS. 18-27, shown in a first condition;

FIG. 31 is an enlarged view of the indicated area of detail of FIG. 30;

FIG. 43 is a longitudinal cross-section of the adapter assembly of FIGS. 37 and 38, as taken through 43-43 of FIG. 37;

FIG. 44 is an enlarged view of the indicated area of detail of FIG. 43;

DETAILED DESCRIPTION OF EMBODIMENTS

Figure 1A:
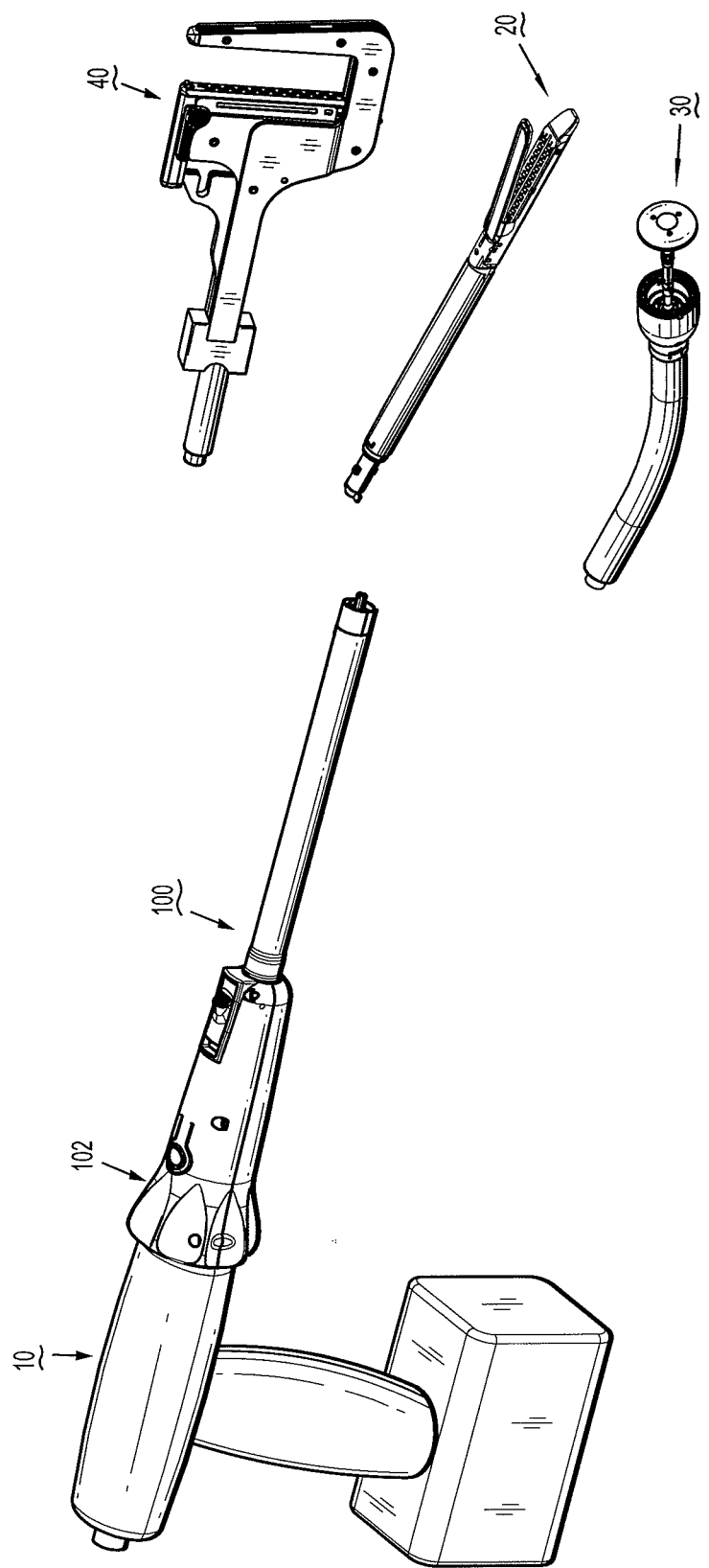
FIG. 1A is a perspective view of the exemplary surgical device and/or handle assembly of FIG. 1, illustrating the potential use with various end effectors.
Figure 2:
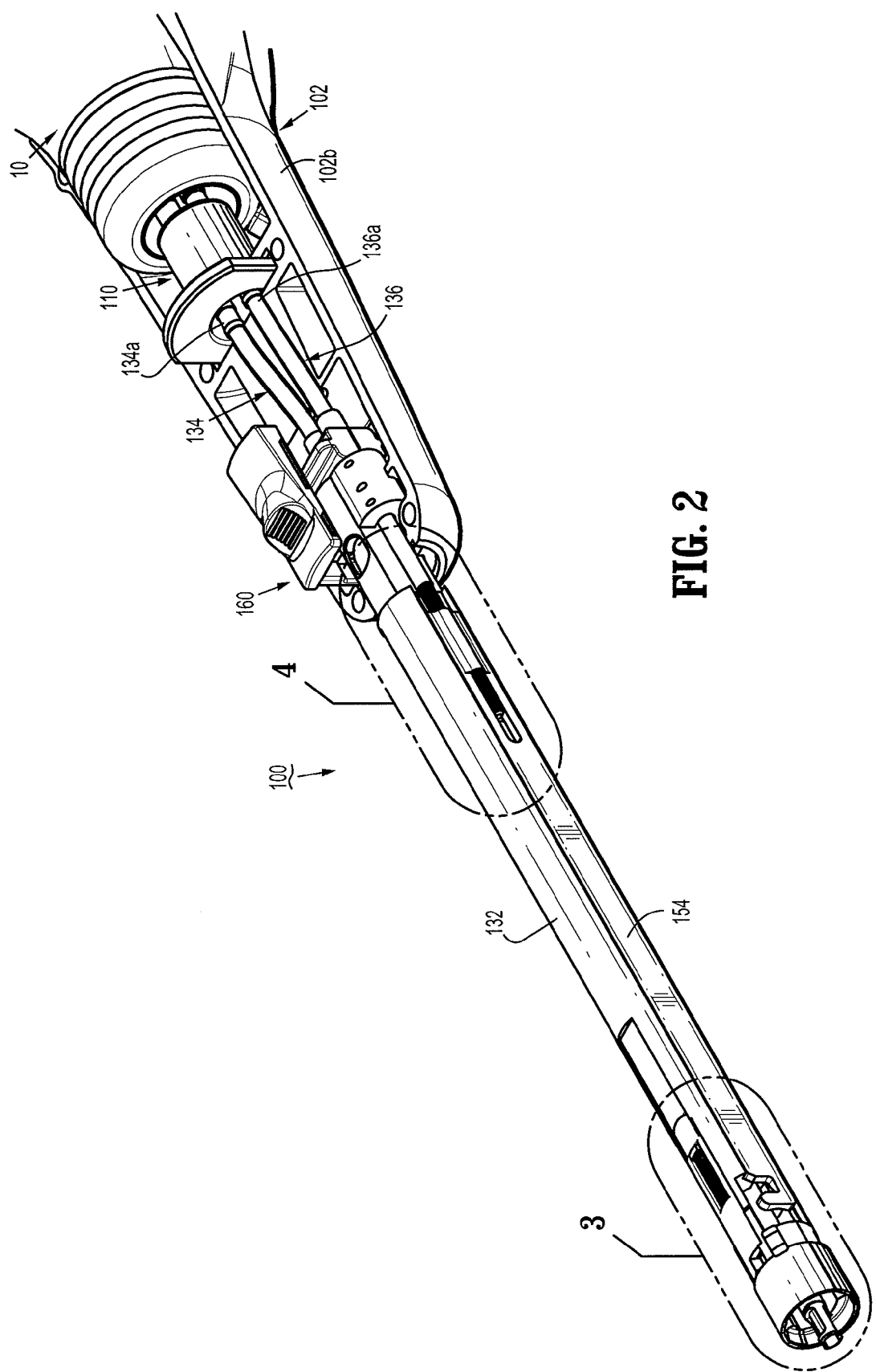
FIG. 2 is an enlarged perspective view of the adapter assembly of FIG. 1, shown supported on a distal end of the exemplary surgical device and/or handle assembly of FIG. 1 and shown with an outer tube and an upper knob housing half-section removed therefrom.
Figure 3:
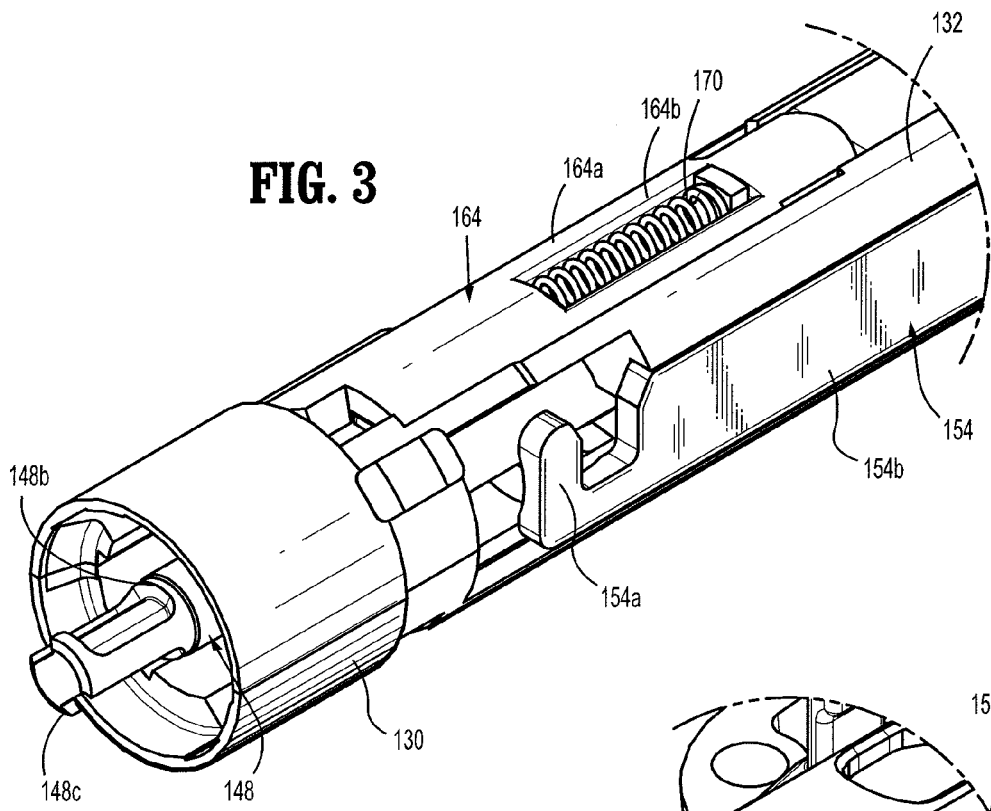
FIG. 3 is an enlarged perspective view of the indicated area of detail of FIG. 2.
Figure 4:
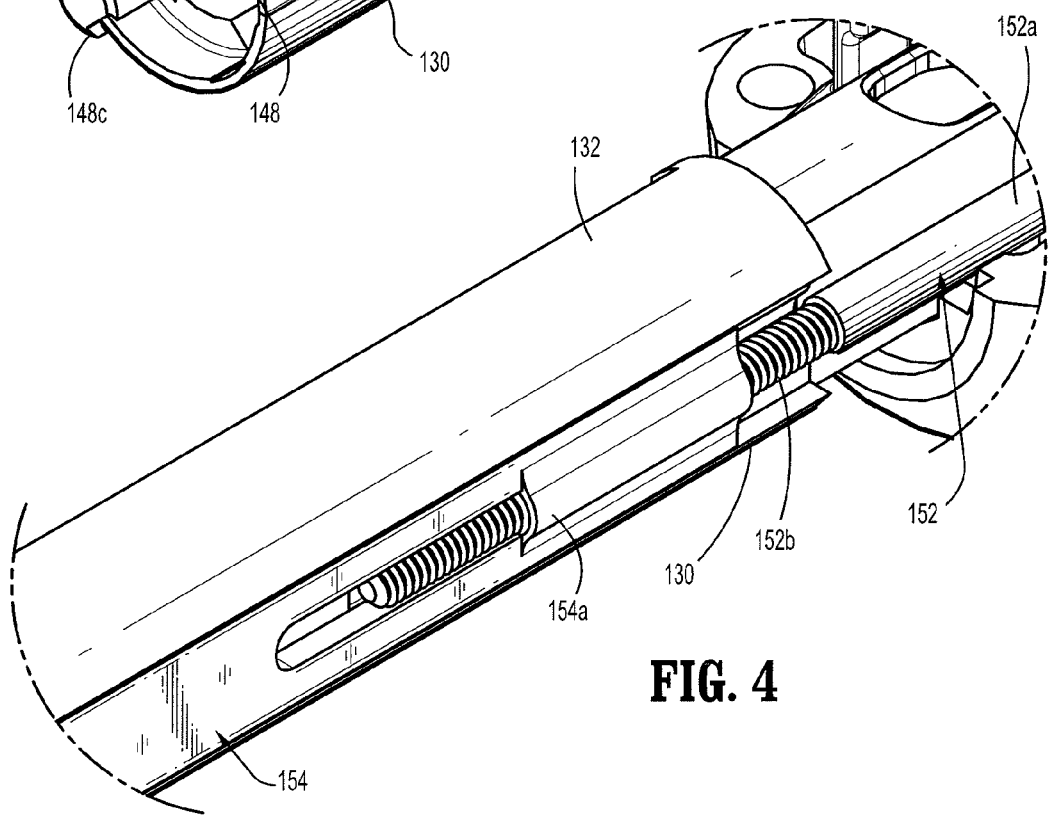
FIG. 4 is an enlarged perspective view of the indicated area of detail of FIG. 2.

Embodiments of the presently disclosed adapter assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

Referring initially to FIGS. 1 and 1A, an adapter assembly in accordance with an embodiment of the present disclosure is shown and generally designated 100. As seen in FIGS. 1 and 1A, adapter assembly 100 is shown connected to or otherwise supported on a surgical device 10, here shown as a hand held powered surgical driver or the like. Reference may be made to International Application No. PCT/US2008/077249, filed Sep. 22, 2008 (Inter. Pub. No. WO 2009/039506), the entire content of which is incorporated herein by reference, for a detailed description of the construction and operation of exemplary surgical devices 10, for use with adapter assembly 100. Surgical devices 10 may include a housing, at least one drive motor, at least one energy source for powering the at least one drive motor, and at least one rotatable drive shaft connected to the drive motor.

In accordance with the present disclosure, surgical device 10 includes a first and a second drive motor, and a first and a second rotatable drive member or shaft, respectively connected to the first and second drive motors. In use, as the first drive motor is activated, the first drive motor will cause the first drive shaft to selectively rotate along its axis in either a first or clock-wise direction, or in a second or counter clock-wise direction. Additionally, as the second drive motor is activated, the second drive motor will cause the second drive shaft to selectively rotate along its axis in either a first or clock-wise direction, or in a second or counter clock-wise direction.

Figure 36:
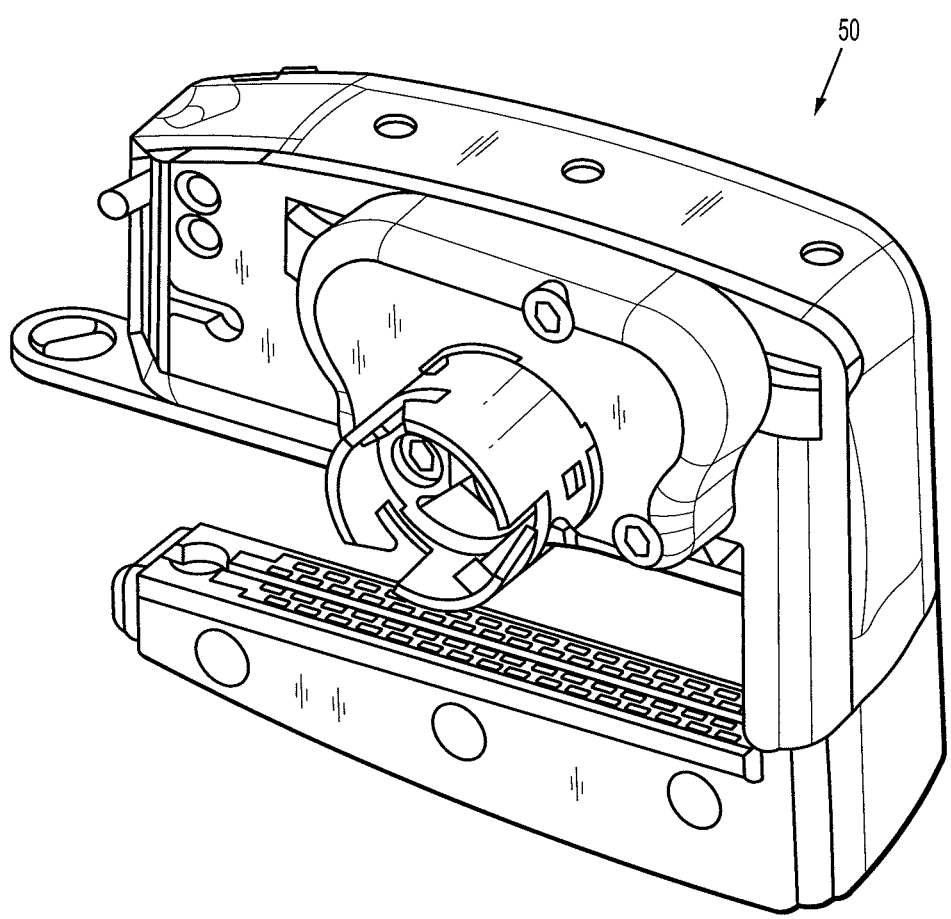
FIG. 36 is a perspective view of a right angled linear cutter/stapler end effector for use with an adapter system according to an embodiment of the present disclosure.
Figure 37:
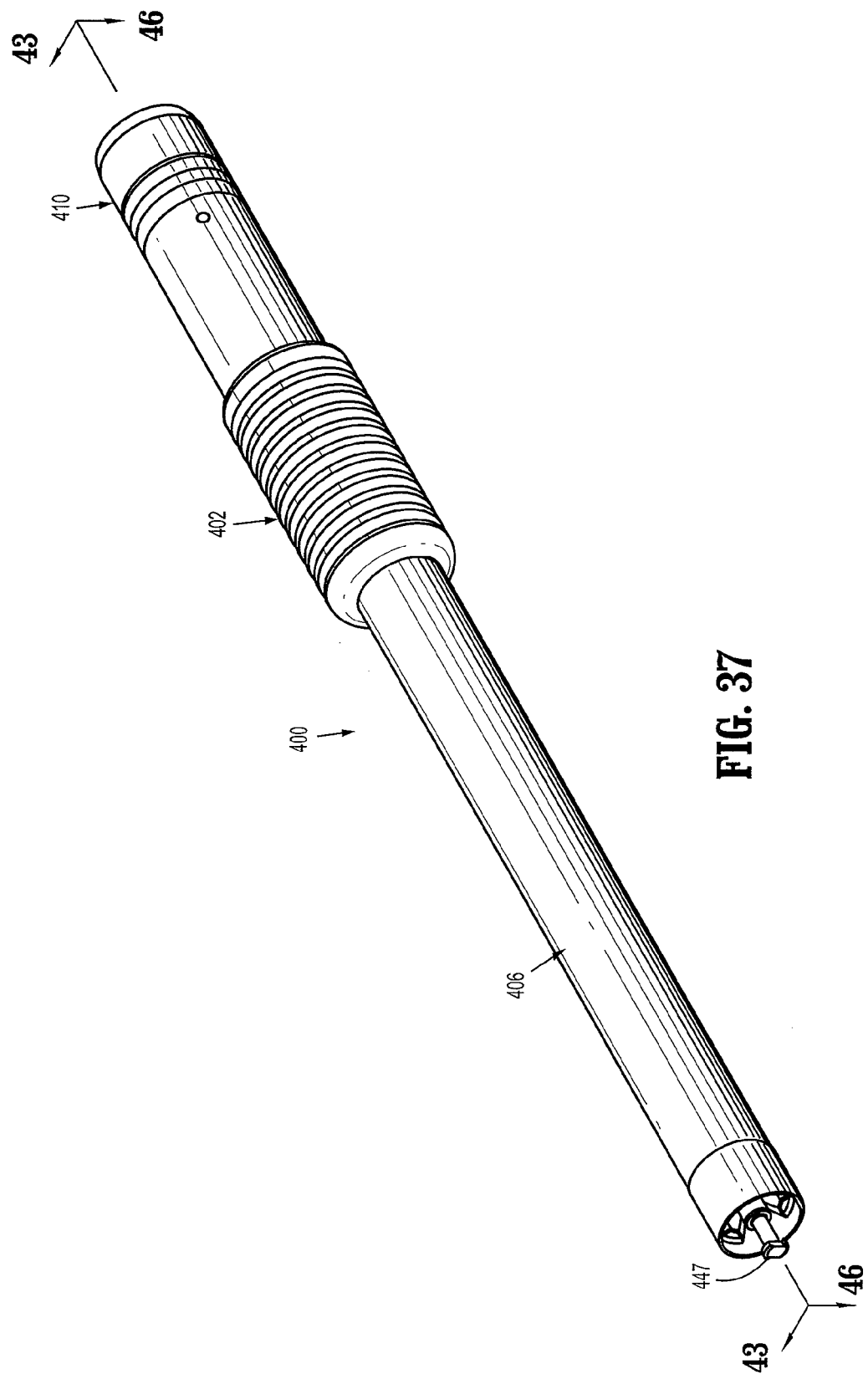
FIG. 37 is a front perspective view of an adapter assembly according to yet another embodiment of the present disclosure.
Figure 38:
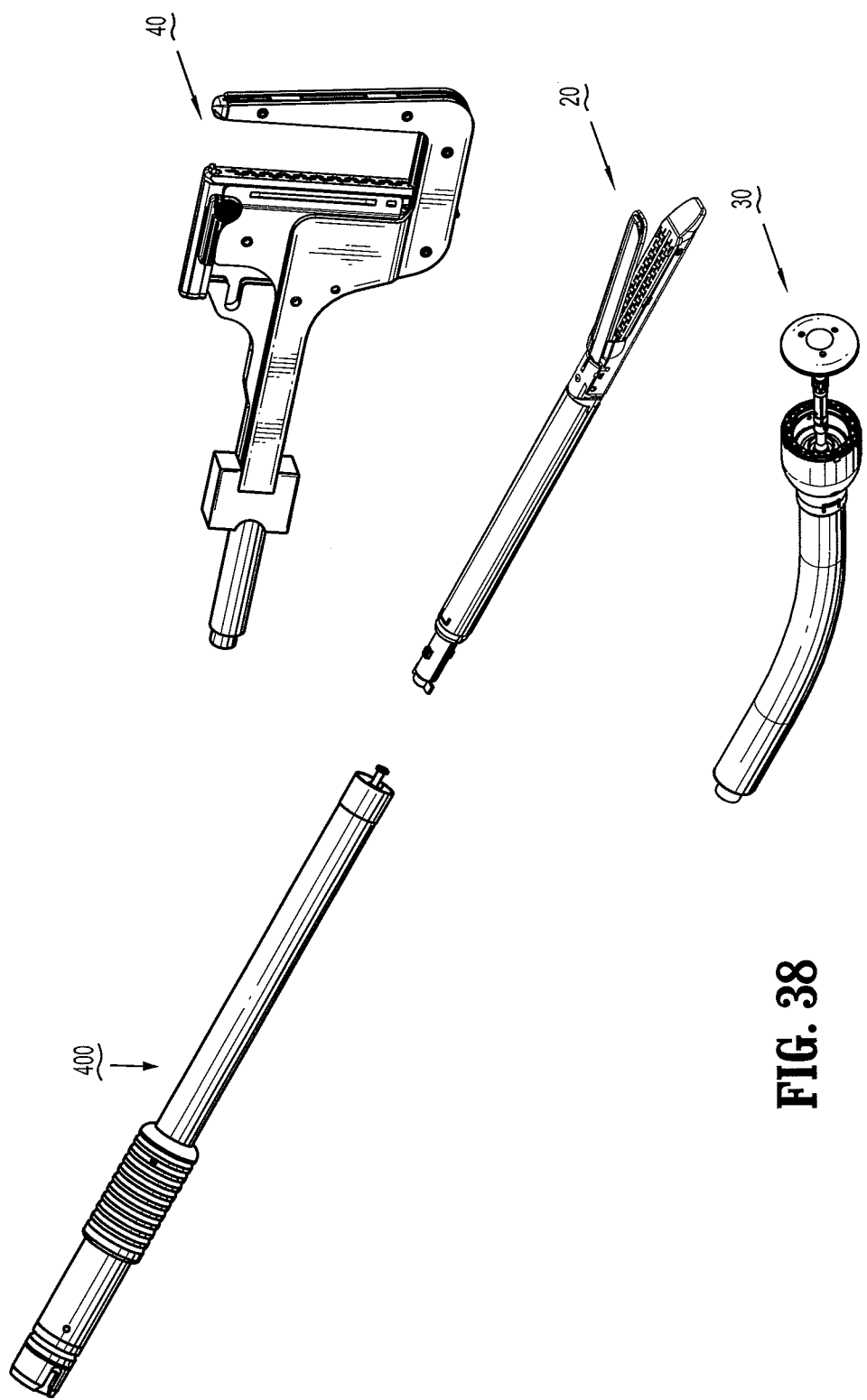
FIG. 38 is a perspective view of the adapter assembly of FIG. 37, illustrating the potential use thereof with various end effectors.

As seen in FIG. 1A, adapter assembly 100 is configured and adapted to operatively interconnect and couple any one of a number of end effectors to surgical device 10. For example, adapter assembly 100 is configured and adapted to operatively interconnect and couple an endo-gastrointestinal anastomosis end effector 20, an end-to-end anastomosis end effector 30 or a transverse anastomosis end effector 40 to surgical device 10. An adapter may be provided for connecting a right angled linear cutter/stapler end effector 50, as seen in FIG. 36, to surgical device 10, as needed and/or desired.

Reference may be made to U.S Patent Publication No. 2009/0145947, filed Jan. 14, 2009, the entire content of which is incorporated herein by reference for a detailed discussion of the construction and operation of the endo-gastrointestinal anastomosis end effector 20.

Reference may be made to U.S Patent Publication No. 2009/0179063, filed Mar. 20, 2009, the entire content of which is incorporated herein by reference for a detailed discussion of the construction and operation of the end-to-end anastomosis end effector 30.

Reference may be made to U.S. Pat. No. 6,817,508, issued Nov. 16, 2004, the entire content of which is incorporated herein by reference for a detailed discussion of the construction and operation of the transverse anastomosis end effector 40.

Reference may be made to U.S Patent Publication No. 2003/0130677, filed Mar. 8, 2002, the entire content of which is incorporated herein by reference for a detailed discussion of the construction and operation of the right angled linear cutter/stapler end effector 50 (see FIG. 36).

Each of end effectors 20, 30 and 40 includes at least one axially translatable drive member therein that is configured and adapted to at least one of open and close the jaw assemblies by approximating or separating the anvil assembly and the cartridge assembly to/away from one another, and to fire the end effector to expel staples contained in the cartridge assembly for formation against the anvil assembly and possibly to actuate a knife blade along the staple line. Each of end effectors 20, 30 and 40 may further include an axially translatable drive member therein that is configured and adapted to cause an articulation of end effector 20, 30 and/or 40.

Meanwhile end effector 50 includes at least one rotatably drive member therein that is configured and adapted to at least one of open and close the jaw assemblies by approximating or separating the anvil assembly and the cartridge assembly to/away from one another, and to fire the end effector to expel staples contained in the cartridge assembly for formation against the anvil assembly and possibly to actuate a knife blade along the staple line.

With continued reference to FIGS. 1 and 1A, and with reference to FIGS. 2-17, a detailed description of the construction and operation of adapter assembly 100 is provided. Adapter assembly 100 includes a knob housing 102 configured and adapted to connect to a nose of surgical device 10. Knob housing 102 includes a release button 104 that is actuatable to disconnect adapter assembly 100 from surgical device 10. Knob housing 102 may be formed in a pair of housing halves, namely an upper housing half 102a and a lower housing half 102b. Adapter assembly 100 further includes an outer tube 106 extending from a distal end of knob housing 102. Knob housing 102 and outer tube 106 are configured and dimensioned to house the components of adapter assembly 100. Outer tube 106 may be dimensioned such that outer tube may pass through a typical trocar port, cannula or the like.

As seen in FIGS. 2 and 5-7, adapter assembly 100 includes a surgical device drive coupling assembly 110. Drive coupling assembly 110 includes a distal drive coupling housing 112 rotatably supporting a first and a second proximal drive shaft 114, 116, respectively. Each proximal drive shaft 114, 116 includes a proximal portion 114a, 116a having a shaped or non-circular transverse cross-sectional profile. Drive coupling assembly 110 includes a first and a second coupling sleeve 118, 120, respectively, that is connected to, and extend proximally from, respective proximal portions 114a, 116a of proximal drive shafts 114, 116. Drive coupling assembly 110 includes a proximal drive coupling housing 122 configured to rotatably support first and second coupling sleeves 118, 120. Each of first and second coupling sleeves 118, 120 is configured to mate with a distal end of respective first and second drive shafts (not shown) of surgical device 10.

Figure 7:
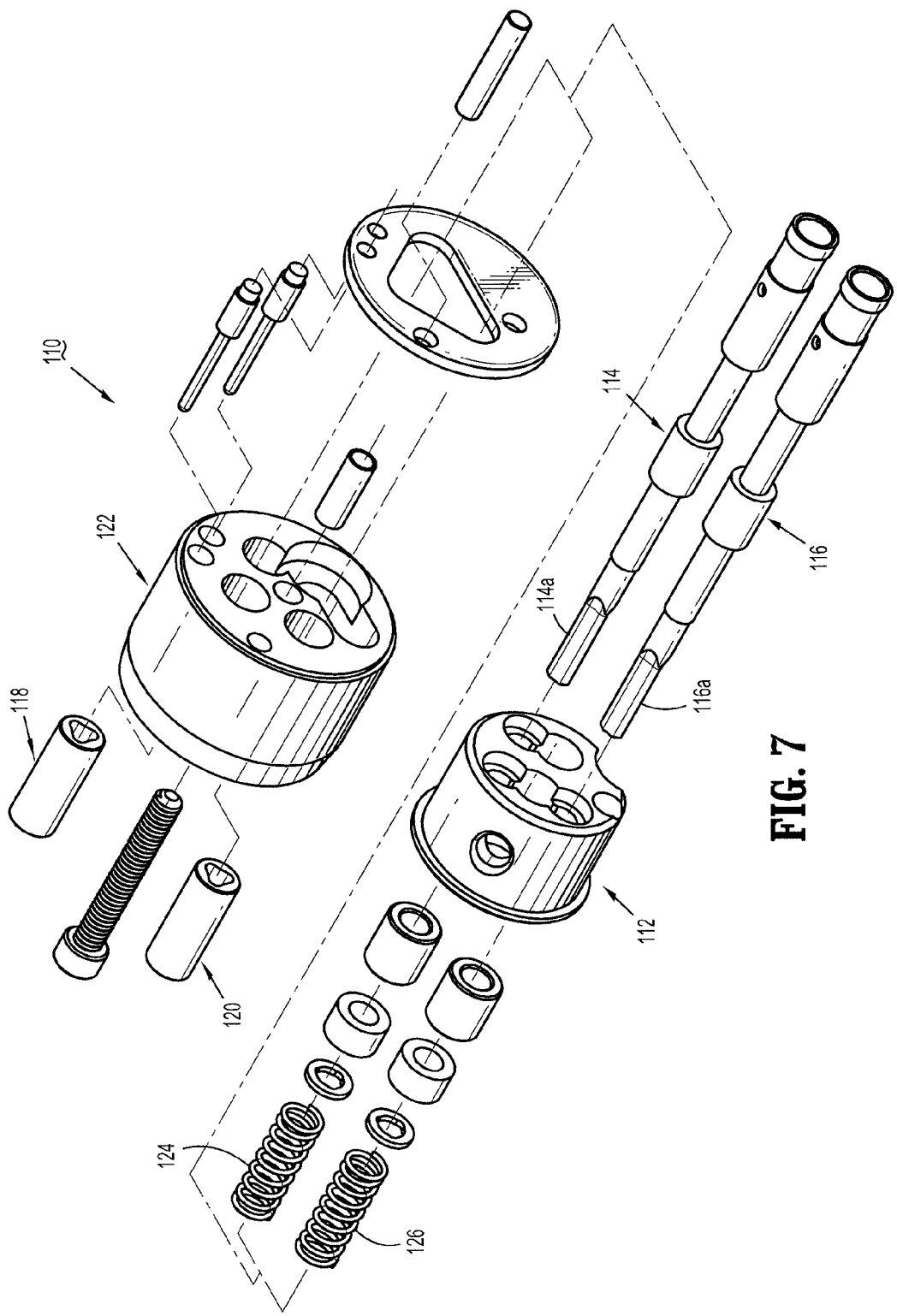
FIG. 7 is an exploded perspective view of the enlarged indicated area of the adapter assembly illustrated in FIG. 6.

As seen in FIGS. 5-7, drive coupling assembly 110 includes a first and a second spring 124, 126 disposed about respective first and second proximal drive shafts 114, 116, and disposed distally of first and second coupling sleeves 118, 120. First and second springs 124, 126 act on first and second coupling sleeves 118, 120 to help maintain coupling sleeves 118, 120 engaged with the distal end of respective first and second drive shafts (not shown) of surgical device 10 when adapter assembly 100 is connected to surgical device 10.

First and second springs 124, 126 function to bias respective first and second coupling sleeves 118, 120 in a proximal direction. In this manner, during assembly of adapter assembly 100 to surgical device 10, if first and second sleeves 118, 120 are misaligned with the driving shafts of surgical device 10, first and/or second spring(s) 124, 126 are compressed. Thus, when the drive motor of surgical device 10 is engaged, the driving shaft of surgical device 10 will rotate and first and/or second spring(s) 124, 126 will cause respective first and/or second coupling sleeve 118, 120 to slide back proximally, effectively coupling the drive rods of surgical device 10 to first and/or second proximal drive shaft(s) 114, 116 of drive coupling assembly 110.

Turning now to FIGS. 2-5 and 8, adapter assembly 100 includes a first and a second drive converter assembly 140, 150, respectively. Each drive converter assembly 140, 150 is configured and adapted to convert a rotation of a respective first and second drive shaft (not shown) of surgical device 10, and concomitant rotation of respective first and second proximal drive shafts 114, 116, into axial translation of respective drive members or the like of adapter assembly 100.

As seen in FIGS. 2-5 and 8, adapter assembly 100 includes a lower housing half 130 and an upper housing half 132 disposed within outer tube 106. A proximal end of housing halves 130, 132 is supported in a distal end of knob housing 102 and is spaced an axial distance from drive coupling assembly 110. A distal end of housing halves 130, 132 may be configured and adapted to selectively engage and couple with a proximal end of any of the end effectors 20, and/or 40. It is contemplated that the distal end of housing halves 130, 132 may be configured to receive the proximal end of any of the end effectors 20, 30 and/or 40 is a bayonet-type configuration or coupling, or any other coupling known by one having skill in the art.

Adapter assembly 100 includes a first flexible drive cable 134 having a proximal end 134a connected to a distal portion of first proximal drive shaft 114, and a second flexible drive cable 136 having a proximal end 136a connected to a distal portion of second proximal drive shaft 116. In this manner, as either of first and/or second proximal drive shafts 114, 116 is/are rotated, the rotation is transmitted to respective first and/or second flexible drive cables 134, 136. Use of flexible drive cables allows for a radial shifting of an axis of rotation of first and/or second proximal drive shafts 114, 116.

Figure 8:
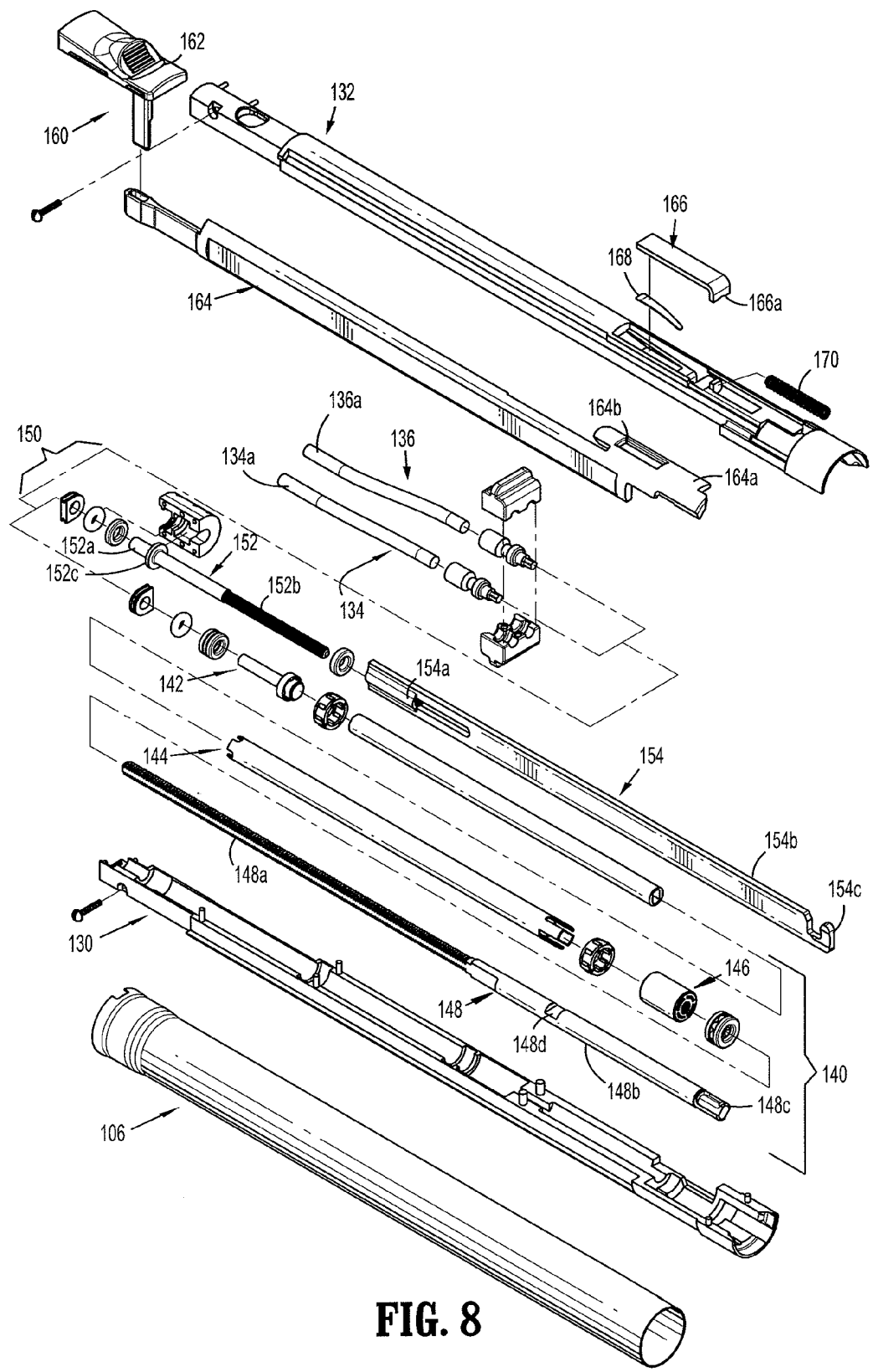
FIG. 8 is an exploded perspective view of a distal end of the adapter assembly of FIGS. 1-5.
Figure 11:
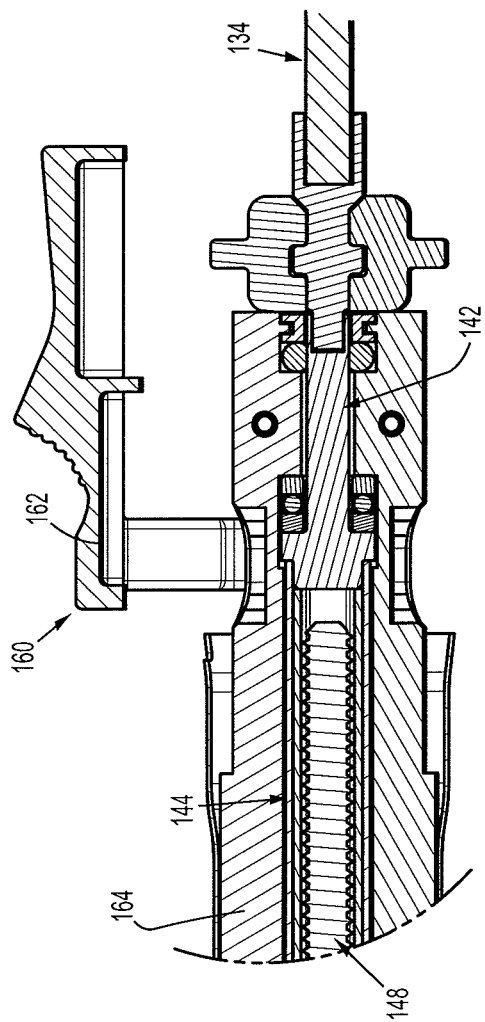
FIG. 11 is an enlarged view of the indicated area of detail of FIG. 9.
Figure 12:
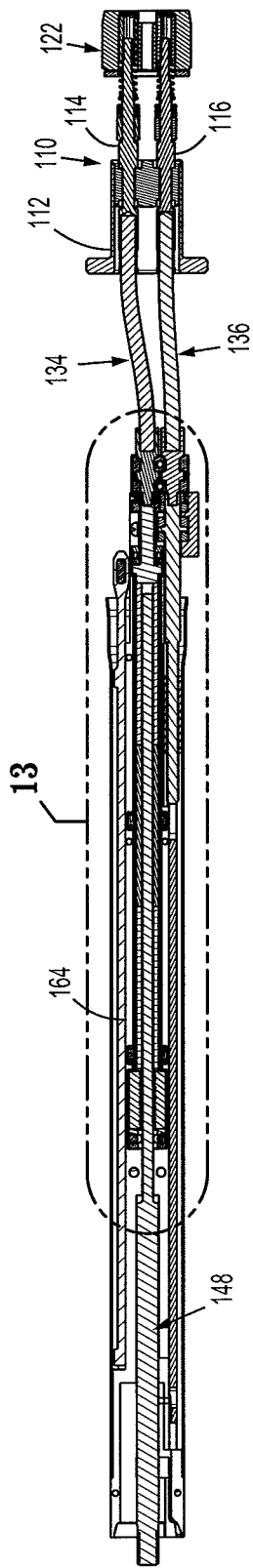
FIG. 12 is a longitudinal, cross-sectional view as taken through 12-12 of FIG. 9.
Figure 13:
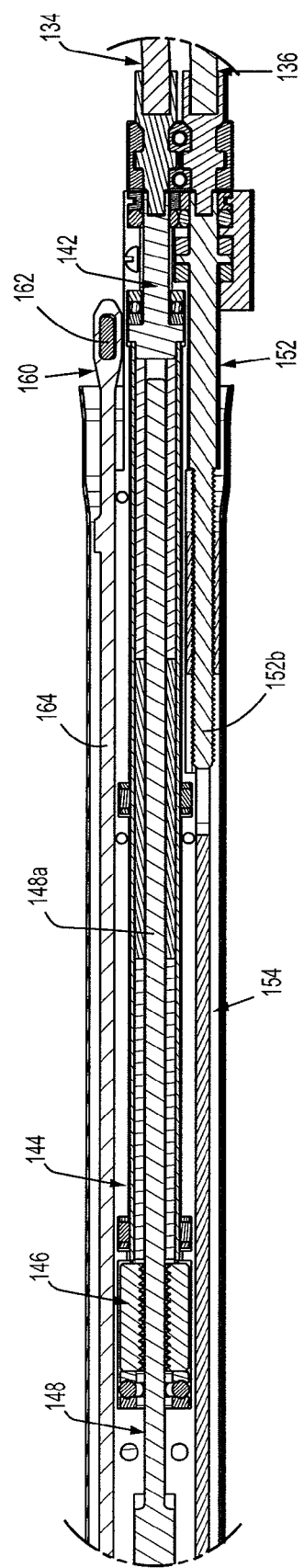
FIG. 13 is an enlarged view of the indicated area of detail of FIG. 12.
Figure 18:
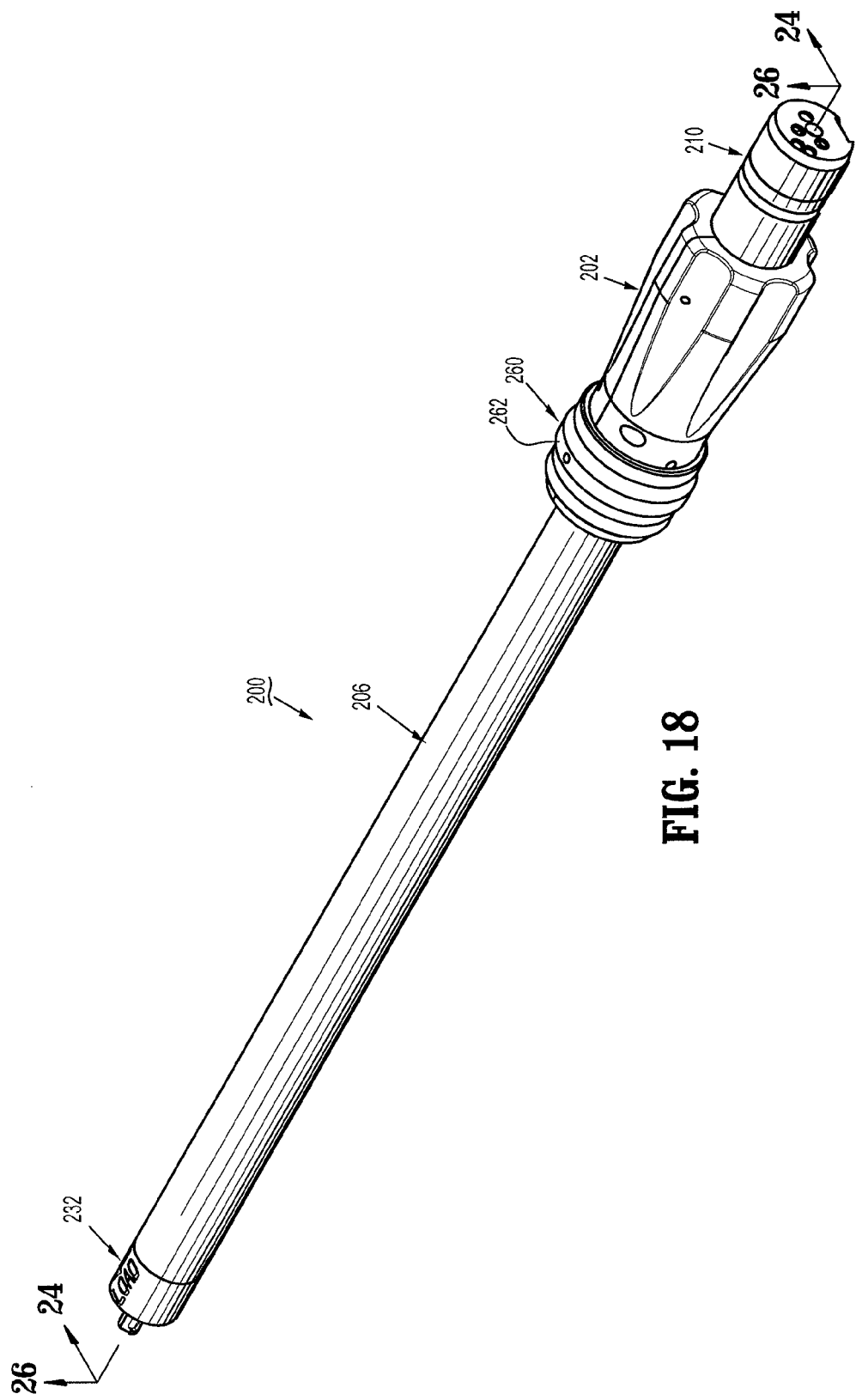
FIG. 18 is a rear perspective view of an adapter assembly according to another embodiment of the present disclosure.
Figure 19:
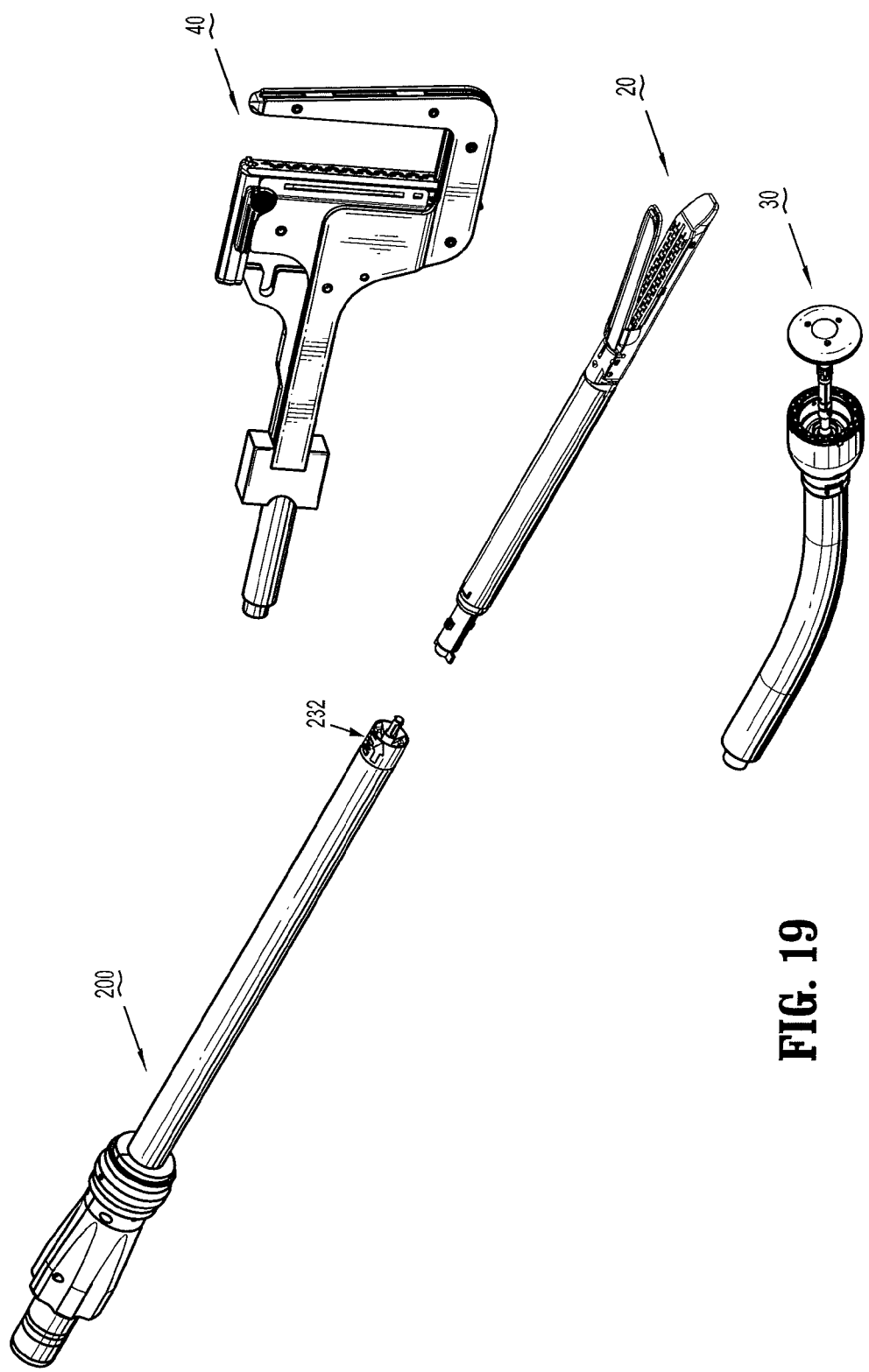
FIG. 19 is a perspective view of the adapter assembly of FIG. 18, illustrating the potential use thereof with various end effectors.
Figure 20:
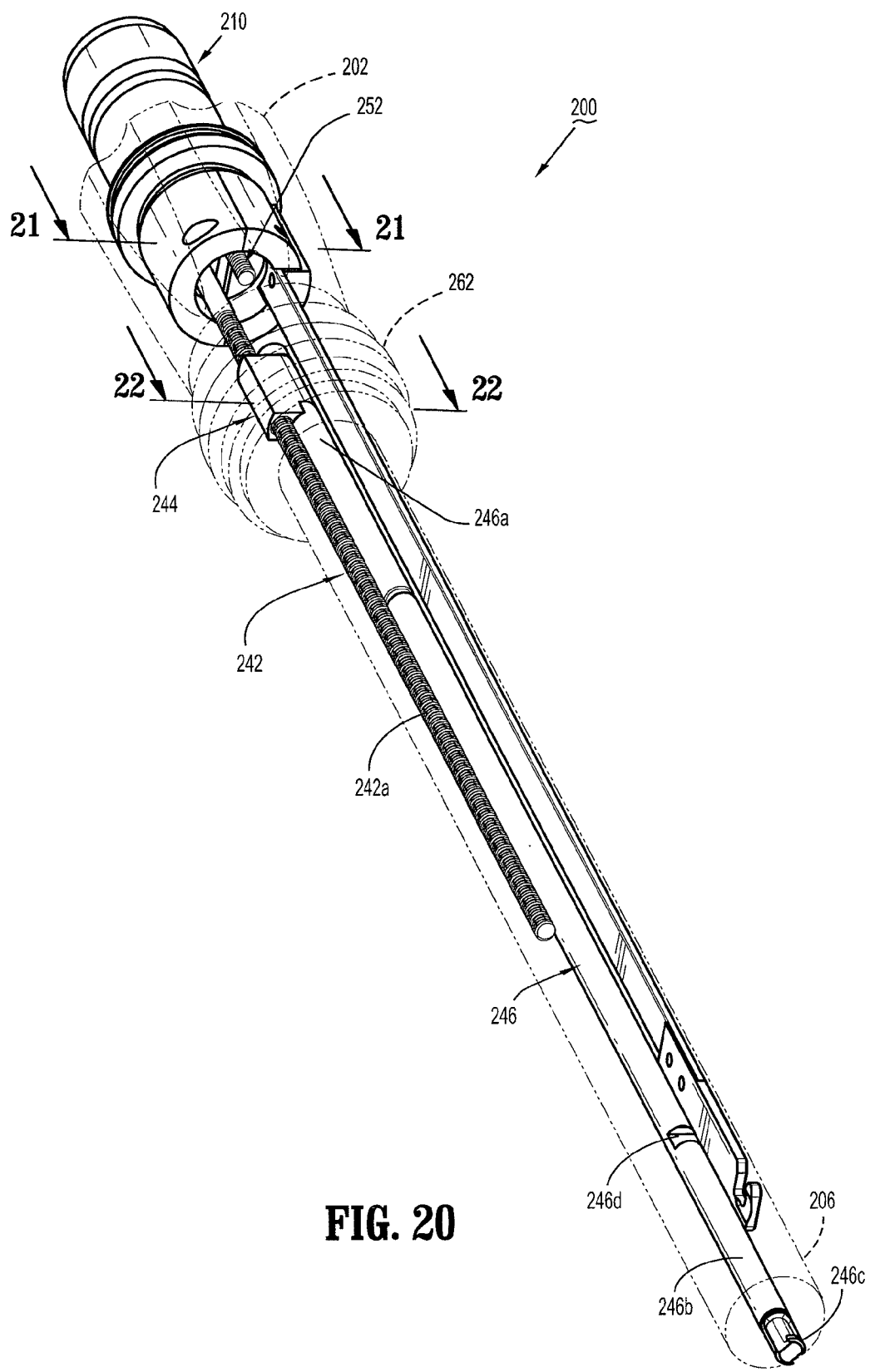
FIG. 20 is a front, perspective view of the adapter assembly of FIGS. 18 and 19, with a knob housing and an outer tube thereof shown in phantom.
Figure 21:
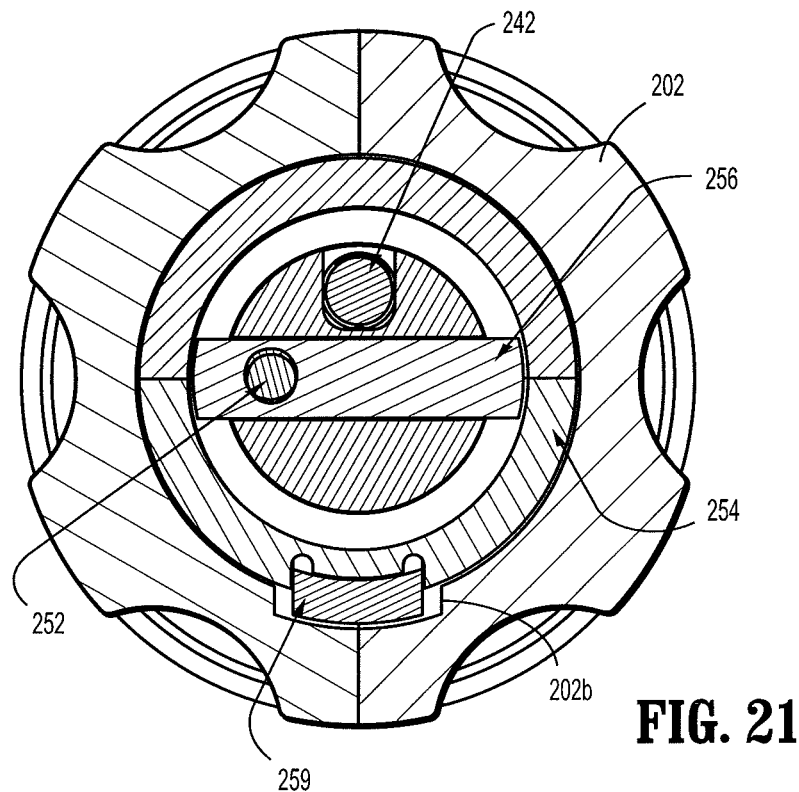
FIG. 21 is a cross-sectional view as taken through 21-21 of FIG. 20.
Figure 22:
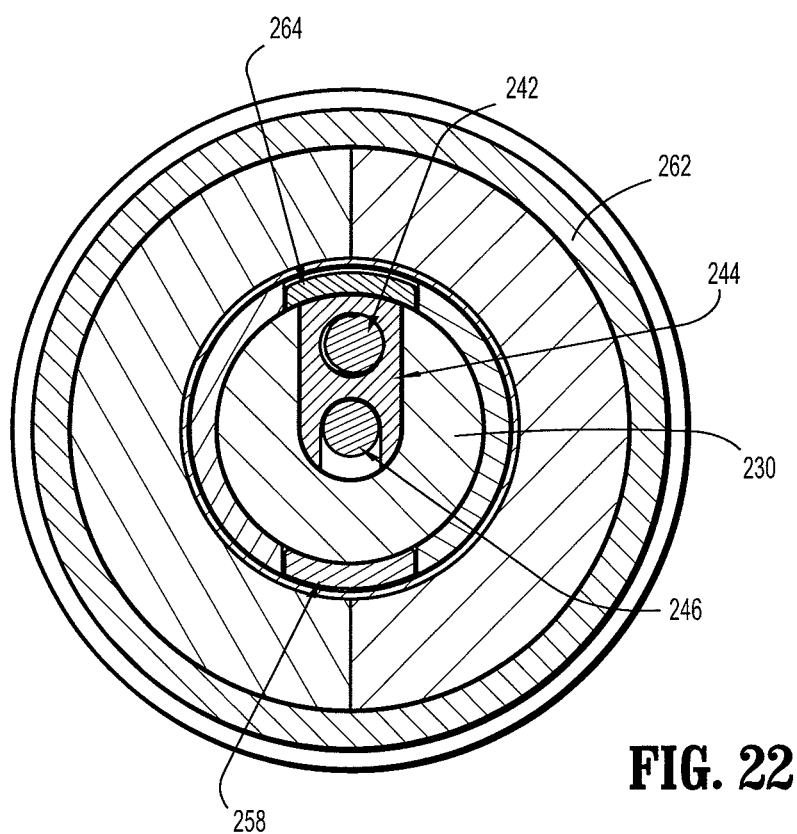
FIG. 22 is a cross-sectional view as taken through 22-22 of FIG. 20.

As seen in FIG. 8, a distal end 134b of first flexible drive cable 134 is connected to first drive converter assembly 140, and a distal end 136b of second drive cable 136 is connected to second drive converter assembly 150.

First drive converter assembly 140 includes a proximal coupling 142 connected to distal end 134b of first flexible drive cable 134 and rotatably supported between lower housing half 130 and upper housing half 132, a tubular sleeve 144 connected to proximal coupling 142 and rotatably supported between lower housing half 130 and upper housing half 132, and a distal coupling nut 146 connected to a distal end of tubular sleeve 144 and rotatably supported between lower housing half 130 and upper housing half 132. Each of proximal coupling 142, tubular sleeve 144 and coupling nut 146 may be rotatably supported between lower housing half 130 and upper housing half 132 by any number of appropriately positioned and sized bearings and/or bushings (not numbered).

As seen in FIGS. 8 and 10, first drive converter assembly 140 further includes a drive shaft 148 translatably supported for axial reciprocation between lower housing half 130 and upper housing half 132. Drive shaft 148 includes a threaded proximal end portion 148a threadably coupled to coupling nut 146 and a distal end portion 148b extending from a distal end of lower housing half 130, upper housing half 132, and outer tube 106. Distal end portion 148b of drive shaft 148 defines a connection member 148c configured and adapted for selective engagement with an axially translatable drive member of any of end effectors 20, 30 and/or 40.

In operation, as seen in FIGS. 16 and 17, as coupling nut 146 is rotated (in the direction of arrow "A") due to a rotation of tubular sleeve 144, proximal coupling 142, first flexible drive cable 132 and the first proximal drive shaft 114, as a result of the rotation of the first drive shaft of surgical device 10, drive shaft 148 is caused to be translated axially (in the direction of arrow "B") relative to coupling nut 146. Accordingly, as drive shaft 148 is translated axially, with connection member 148c thereof connected to a drive member of any of end effectors 20, 30 and/or 40, drive shaft 148 causes concomitant axial translation of the drive member of any of end effectors 20, 30 and/or 40 to effectuate an operation and/or function thereof, such as, for example, the firing of the end effector or the like.

With reference to FIGS. 2-4 and 8, second drive converter assembly 150 includes a drive shaft 152 rotatably supported between lower housing half 130 and upper housing half 132. Drive shaft 152 includes a proximal end portion 152a having a flange 152c extending radially therefrom in order to fix an axial position of drive shaft 152 relative to lower housing half 130 and upper housing half 132. Proximal end portion 152a of drive shaft 152 is coupled to second flexible drive cable 136. Drive shaft 152 further includes a threaded distal portion 152b.

Second drive converter assembly 150 further includes a drive bar 154 translatably supported for axial translation between lower housing half 130 and upper housing half 132. Drive bar 154 includes a threaded proximal end portion 154a threadably coupled to threaded distal portion 152b of drive shaft 152, and a distal end portion 154b defining a coupling hook 154c or the like.

In operation, as seen in FIGS. 14 and 15, as drive shaft 152 is rotated (in the direction of arrow "C") due to a rotation of second flexible drive cable 136 and of second proximal drive shaft 116, as a result of the rotation of the second drive shaft of surgical device 10, drive bar 154 is caused to be translated axially (in the direction of arrow "B") relative to drive shaft 152. Accordingly, as drive bar 154 is translated axially, with hook 154c thereof connected to a drive member of any of end effectors 20, 30 and/or 40, drive bar 154 causes concomitant axial translation of the drive member of any of end effectors 20, 30 and/or 40 to effectuate an operation and/or function thereof, such as, for example, articulation of the end effector, the firing of a knife blade or the like.

With reference to FIGS. 2, 3 and 8-11, adapter assembly 100 further includes a lock mechanism 160 configured and adapted to fix the axial position and radial orientation of drive shaft 148 for the connection and disconnection of end effectors 20, 30 and/or 40 thereto. Lock mechanism 160 includes a button or lever 162 slidably supported on knob housing 102. Lock button 162 is connected to an actuation bar 164 that extends longitudinally through outer tube 106. Actuation bar 164 is interposed between outer tube 106 and lower housing half 130 and upper housing half 132. Actuation bar 164 is configured and dimensioned such that movement of lock button 162 results in movement of actuation bar 164. Actuation bar 164 includes a distal portion 164a defining a window 164b therein. As seen in FIG. 10, a distal end of window 164b defines a cam surface 164c.

Lock mechanism 160 further includes a lock arm 166 supported on upper housing half 132 at a location in registration with window 164b of distal portion 164a of actuation bar 164. Lock arm 166 includes a tab 166a extending toward drive shaft 148. Tab 166a of lock arm 166 is configured and dimensioned to selectively engage a cut-out 148d formed in drive shaft 148. Lock mechanism 160 further includes a biasing member 168 tending to maintain lock arm 166 and tab 166a thereof spaced away from drive shaft 148.

In operation, in order to lock the position and/or orientation of drive shaft 148, a user moves lock button 162 from a distal position to a proximal position, thereby causing cam surface 164c of actuation bar 164 to engage lock arm 166 and urge lock arm 166 toward drive shaft 148, against the bias of biasing member 168, such that tab 166a of lock arm 166 is received in cut-out 148d of drive shaft 148. In this manner, drive shaft 148 is prevented from distal and/or proximal movement. When lock button 162 is moved from the proximal position to the distal position, cam surface 164c is disengaged from lock arm 166 thereby allowing biasing member 168 to urge lock arm 166 and tab 166a thereof out of cut-out 148d of drive shaft 148.

It is contemplated that lock mechanism 160 may include a biasing member 170 tending to maintain lock button 162 and actuation bar 164 in the distal position.

Turning now to FIGS. 18-34, an adapter assembly, configured and adapted to operatively interconnect and couple any one of a number of end effectors to surgical device 10, in accordance with another embodiment of the present disclosure, is generally designated as adapter assembly 200.

Adapter assembly 200 includes a knob housing 202 configured and adapted to connect to a nose of surgical device 10. Adapter assembly 200 further includes an outer tube 206 extending from a distal end of knob housing 202. Knob housing 202 and outer tube 206 are configured and dimensioned to house the components of adapter assembly 200. Outer tube 206 may be dimensioned such that outer tube may pass through a typical trocar port, cannula or the like.

As seen in FIGS. 20 and 23-27, adapter assembly 200 includes a surgical device drive coupling assembly 210. Drive coupling assembly 210 includes a distal drive coupling housing 212 rotatably supported in knob housing 202. Drive coupling assembly 210 includes a proximal drive coupling housing 222 configured to rotatably support first and second coupling sleeves 218, 220. Each of first and second coupling sleeves 218, 220 is configured to mate with a distal end of respective first and second drive shafts (not shown) of surgical device 10. It is contemplated that drive coupling assembly 210 includes a first and a second biasing member (not shown) disposed distally of first and second coupling sleeves 218, 220 to act on first and second coupling sleeves 218, 220 to help maintain coupling sleeves 218, 220 engaged with the distal end of respective first and second drive shafts (not shown) of surgical device 10 when adapter assembly 200 is connected to surgical device 10.

Figure 23:
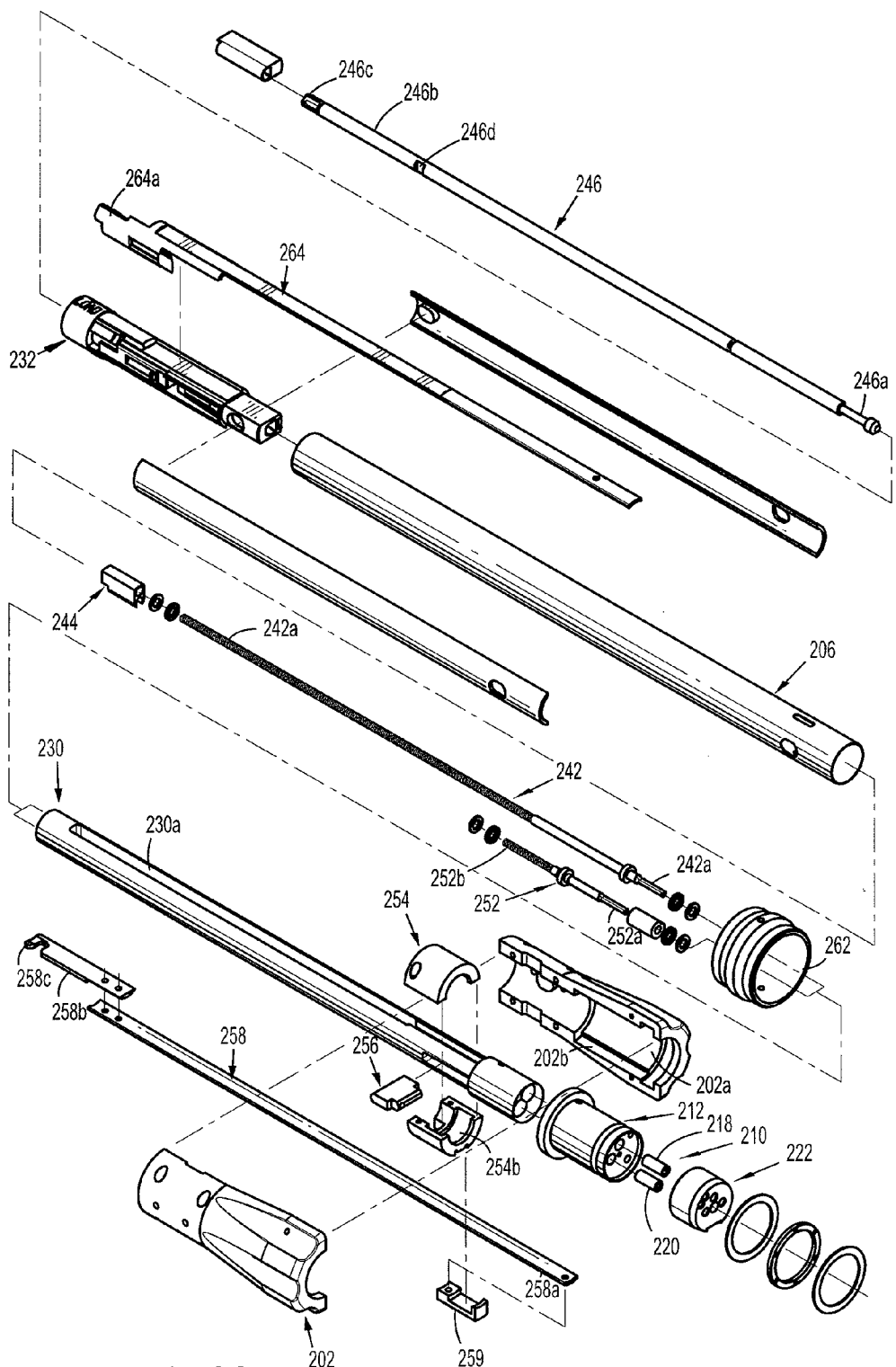
FIG. 23 is a rear, exploded perspective view of the adapter assembly of FIGS. 18-22.
Figure 26:
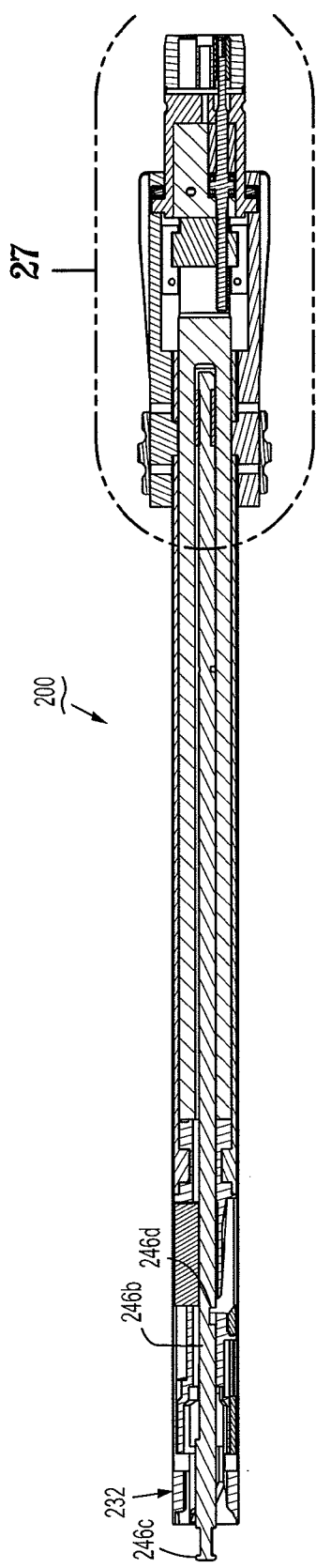
FIG. 26 is a longitudinal, cross-sectional view of the adapter assembly of FIGS. 18-25, as taken through 26-26 of FIG. 18.
Figure 27:
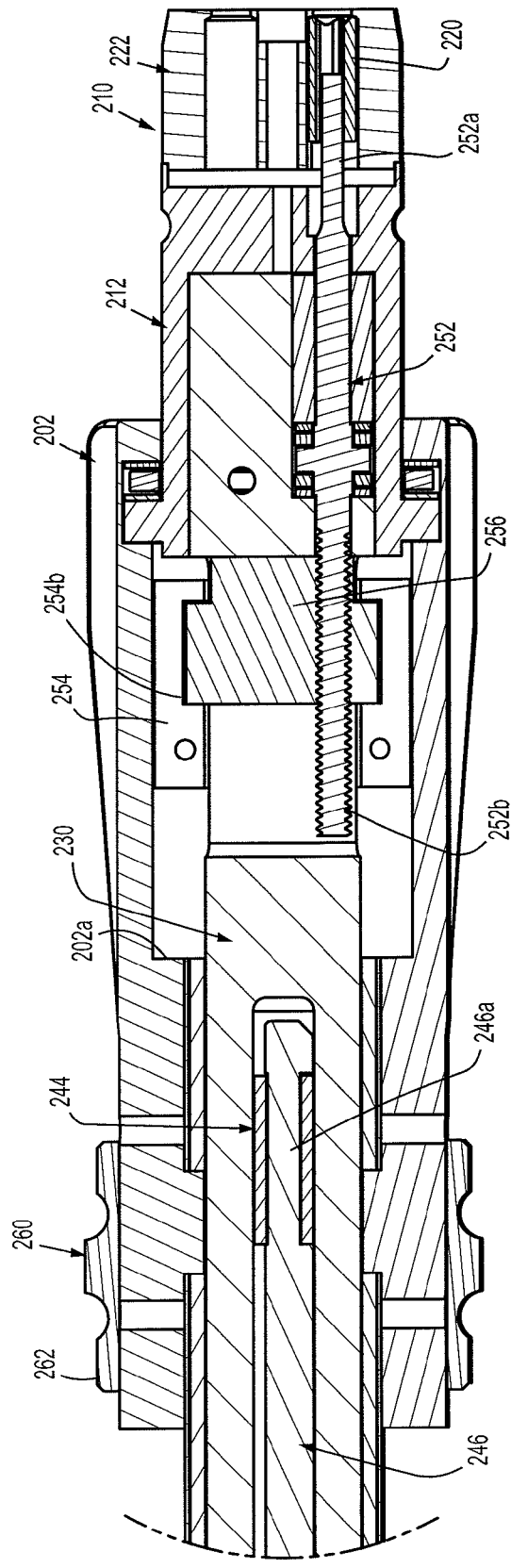
FIG. 27 is an enlarged view of the indicated area of detail of FIG. 26.
Figure 32:
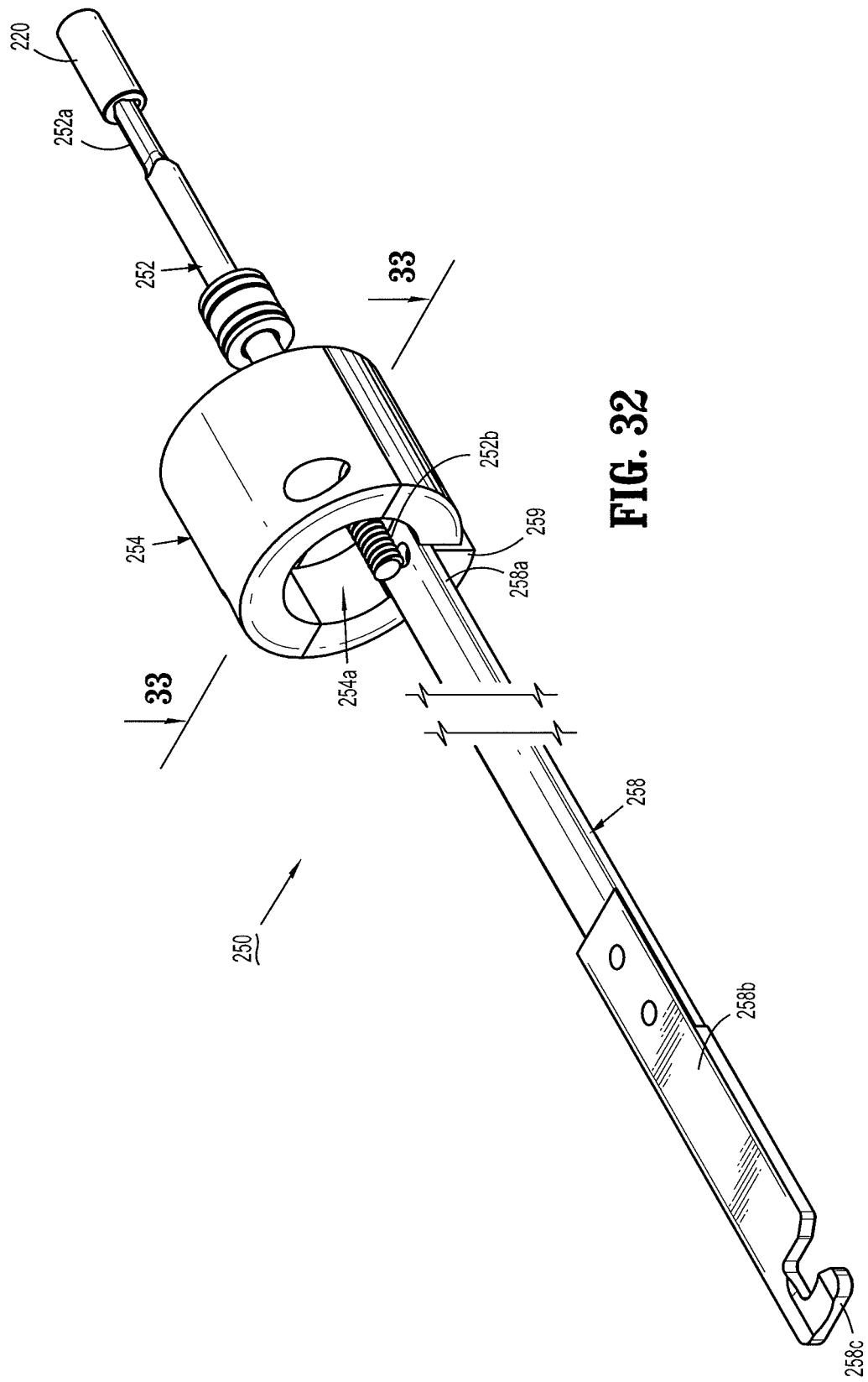
FIG. 32 is a further perspective view of the second drive assembly of FIGS. 30 and 31.
Figure 33:
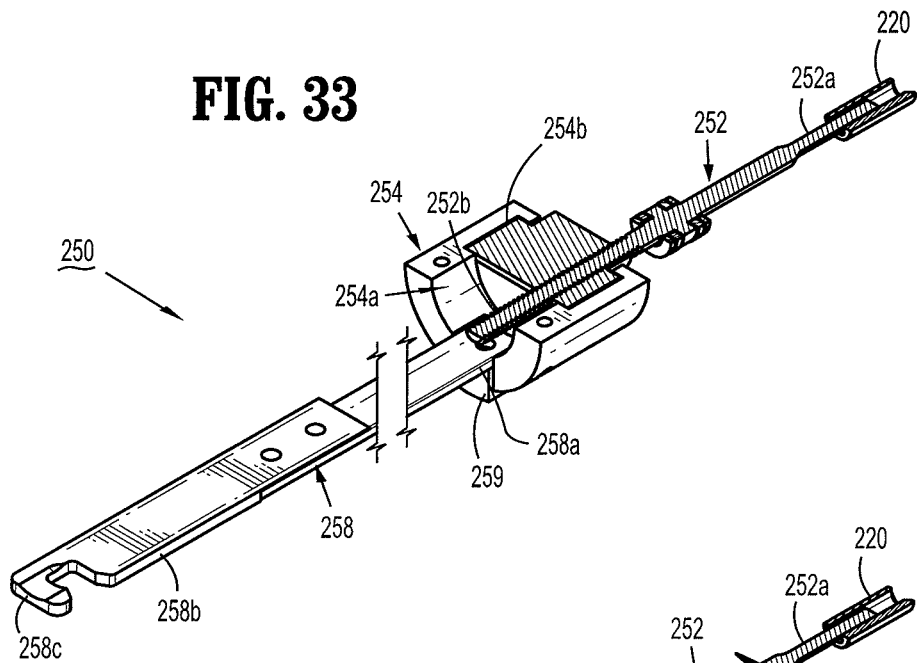
FIG. 33 is a cross-sectional view of the second drive assembly as taken through 33-33 of FIG. 32.
Figure 34:
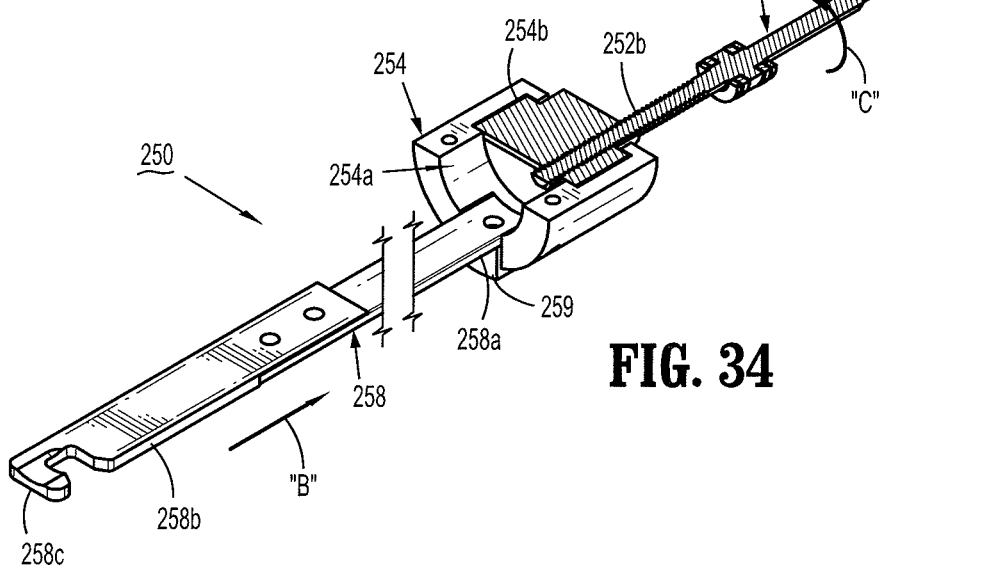
FIG. 34 is a cross-sectional, perspective view of the second drive assembly of FIGS. 30-33, as taken through 33-33 of FIG. 32, illustrating an operation thereof.

Turning now to FIGS. 20-27, adapter assembly 200 includes a first and a second drive converter assembly 240, 250, respectively (see FIG. 23). Each drive converter assembly 240, 250 is configured and adapted to convert a rotation of a respective first and second drive shaft (not shown) of surgical device 10 into axial translation of respective drive members or the like of adapter assembly 200.

As seen in FIGS. 18-27, adapter assembly 200 includes a proximal tubular housing 230 disposed within outer tube 206, and a distal housing 232 disposed at least partially within a distal portion of outer tube 206. Proximal tubular housing 230 defines a longitudinally extending slot 230a formed along a length thereof. A proximal end of proximal tubular housing 230 extends through knob housing 202 and is supported in a distal end of distal drive coupling housing 212 of drive coupling assembly 210. A distal end of distal housing 232 may be configured and adapted to selectively engage and couple with a proximal end of any of the end effectors 20, 30 and/or 40. It is contemplated that the distal end of distal housing 232 may be configured to receive the proximal end of any of the end effectors 20, 30 and/or 40 is a bayonet-type configuration or coupling, or any other coupling known by one having skill in the art.

As seen in FIGS. 20-27, first drive converter assembly 240 includes a first drive shaft 242 rotatably supported within proximal tubular housing 230. First drive shaft 242 includes a non-circular or shaped proximal end portion 242a configured for connection with first coupling sleeve 218 which is connected to the distal end of a first drive shaft (not shown) of surgical device 10. First drive shaft 242 further includes a distal end portion 242b having a threaded outer profile or surface.

First drive converter assembly 240 further includes a drive coupling nut 244 rotatably coupled to threaded distal end portion 242a of first drive shaft 242, and which is slidably disposed within longitudinal slot 230a of proximal housing portion 230. Drive coupling nut 244 is shaped so as to not rotate within longitudinal slot 230a of proximal housing portion 230 as first drive shaft 242 is rotated. In this manner, as first drive shaft 242 is rotated, drive coupling nut 244 is translated through and/or along longitudinal slot 230a of proximal housing portion 230.

First drive converter assembly 240 further includes a first drive bar 246 having a proximal end portion 246a connected to drive coupling nut 244 and a distal end portion 246b extending through distal housing 232. Distal end portion 246b of first drive bar 246 defines a connection member 246c configured and adapted for selective engagement with an axially translatable drive member of any of end effectors 20, 30 and/or 40.

In operation, as seen in FIGS. 24-29, as first drive shaft 242 is rotated (in the direction of arrow "A") due to a rotation of first coupling sleeve 218, as a result of the rotation of the first drive shaft of surgical device 10, drive coupling nut 244 is caused to be translated axially through longitudinal slot 230a of proximal housing portion 230. As drive coupling nut 244 is caused to be translated axially through longitudinal slot 230a of proximal housing portion 230, first drive bar 246 is caused to be translated axially (in the direction of arrow "B") relative to distal housing portion 232. Accordingly, as drive bar 246 is translated axially, with connection member 246c thereof connected to a drive member of any of end effectors 20, 30 and/or 40, drive bar 246 causes concomitant axial translation of the drive member of any of end effectors 20, 30 and/or 40 to effectuate an operation and/or function thereof, such as, for example, the firing of the end effector or the like.

With reference to FIGS. 18-27, second drive converter assembly 250 includes a second drive shaft 252 rotatably supported within drive coupling assembly 210. Second drive shaft 252 includes a non-circular or shaped proximal end portion 252a configured for connection with second coupling sleeve 220 which is connected to the distal end of a second drive shaft (not shown) of surgical device 10. Second drive shaft 252 further includes a distal end portion 252b having a threaded outer profile or surface.

Second drive converter assembly 250 further includes a coupling cuff 254 rotatably and translatably supported within an annular race or recess 202a formed in knob housing 202. Coupling cuff 254 defines a lumen 254a therethrough, and an annular race or recess 254b formed in a surface of lumen 254a. Second drive converter assembly 250 further includes a coupling slider 256 extending across lumen 254a of coupling cuff 254 and slidably disposed within race 254b of coupling cuff 254a. Coupling slider 256 is threadably connected to threaded distal end portion 252b of second drive shaft 252. As so configured, coupling cuff 254 may rotate about second drive shaft 252, thereby maintaining a radial position of second drive shaft 252 relative to first drive shaft 242 and the like.

Second drive shaft 252 defines an axis of rotation, and coupling cuff 254 defines an axis of rotation that is spaced a radial distance from the axis of rotation of second drive shaft 252. Coupling slider 256 defines an axis of rotation that is coincident with the axis of rotation of coupling cuff 254.

Second drive converter assembly 250 further includes a drive bar 258 translatably supported for axial translation through outer tube 206. Drive bar 258 includes a proximal end portion 258a coupled to coupling cuff 254, and a distal end portion 258b defining a coupling hook 258c or the like.

Second drive converter assembly 250 further includes a tab or rib 259 projecting from coupling cuff 254 that is translatably disposed within a longitudinally extending groove 202b formed in knob housing 202.

In operation, as seen in FIGS. 24-27 and 30-34, as drive shaft 252 is rotated (in the direction of arrow "C") due to a rotation of second coupling sleeve 220, as a result of the rotation of the first drive shaft of surgical device 10, coupling slider 256 is caused to be translated axially which in turn causes coupling cuff 254 to be translated axially relative to knob housing 202. As coupling cuff 254 is translated axially, drive bar 258 is caused to be translated axially (in the direction of arrow "B"). Accordingly, as drive bar 258 is translated axially, with hook 258c thereof connected to a drive member of any of end effectors 20, 30 and/or 40, drive bar 258 causes concomitant axial translation of the drive member of any of end effectors 20, 30 and/or 40 to effectuate an operation and/or function thereof, such as, for example, articulation of the end effector, the firing of a knife blade or the like.

Also, in operation, since tab 259 of coupling cuff 254 is translatably disposed within a longitudinally extending groove 202b formed in knob housing 202, as knob housing 202 is rotated about a longitudinal axis, tab 259 and drive bar 258 are caused to be rotated about the longitudinal axis. As such, any of end effectors 20, 30 and/or 40 connected to adapter assembly 200 is also caused to be rotated about the longitudinal axis.

With reference to FIGS. 23-27, it is contemplated that adapter assembly 200 may include a lock mechanism 260 whose construction and operation is substantially similar to lock mechanism 160 of adapter assembly 100.

Lock mechanism 260 includes a lock/release collar 262 translatably supported on knob housing 202 and that is actuatable to fix the axial position and radial orientation of a first drive shaft 246 for the connection and disconnection of end effectors 20, 30 and/or 40 thereto. Lock/release collar 262 is connected to an actuation bar 264 that extends longitudinally through outer tube 206. Actuation bar 264 is interposed between outer tube 206 and proximal housing portion 230 and distal housing portion 232. A connecting member, in the form of a pin or the like (not shown), interconnects lock/release collar 262 and actuation bar 264. The connecting member extends through a slot formed in knob housing 202 and a slot formed in outer tube 206. Actuation bar 264 is configured and dimensioned such that movement of lock/release collar 262 results in movement of actuation bar 264.

Actuation bar 264 includes a distal portion 264a that is configured and adapted to function in a manner substantially similar to distal portion 164a of actuation bar 164 of lock mechanism 160, described above. Accordingly, reference may be made to lock mechanism 160 for a detailed discussion of the construction and operation of distal portion 264a of actuation bar 264 of lock mechanism 260.

Similar to lock mechanism 160, lock mechanism 260 further includes a lock arm supported on the distal housing portion at a location in registration with a window formed in distal portion 264a of actuation bar 264. The lock arm includes a tab extending toward drive shaft 246. The tab of the lock arm is configured and dimensioned to selectively engage a cut-out 246d formed in drive shaft 246 (see FIGS. 20, 23, 26 and 28-29). Lock mechanism 260 further includes a biasing member tending to maintain the lock arm and the tab thereof spaced away from drive shaft 246.

In operation, in order to lock the position and/or orientation of drive shaft 246, a user moves lock/release collar 262 from a distal position to a proximal position, thereby causing the cam surface of actuation bar 264 to engage the lock arm and urge the lock arm toward drive shaft 246, against the bias of the biasing member, such that the tab of the lock arm is received in cut-out 246d of drive shaft 246. In this manner, drive shaft 246 is prevented from distal and/or proximal movement. When lock/release collar 262 is moved from the proximal position to the distal position, the cam surface is disengaged from the lock arm thereby allowing the biasing member to urge the lock arm and the tab thereof out of cut-out 246d of drive shaft 246.

Figure 35:
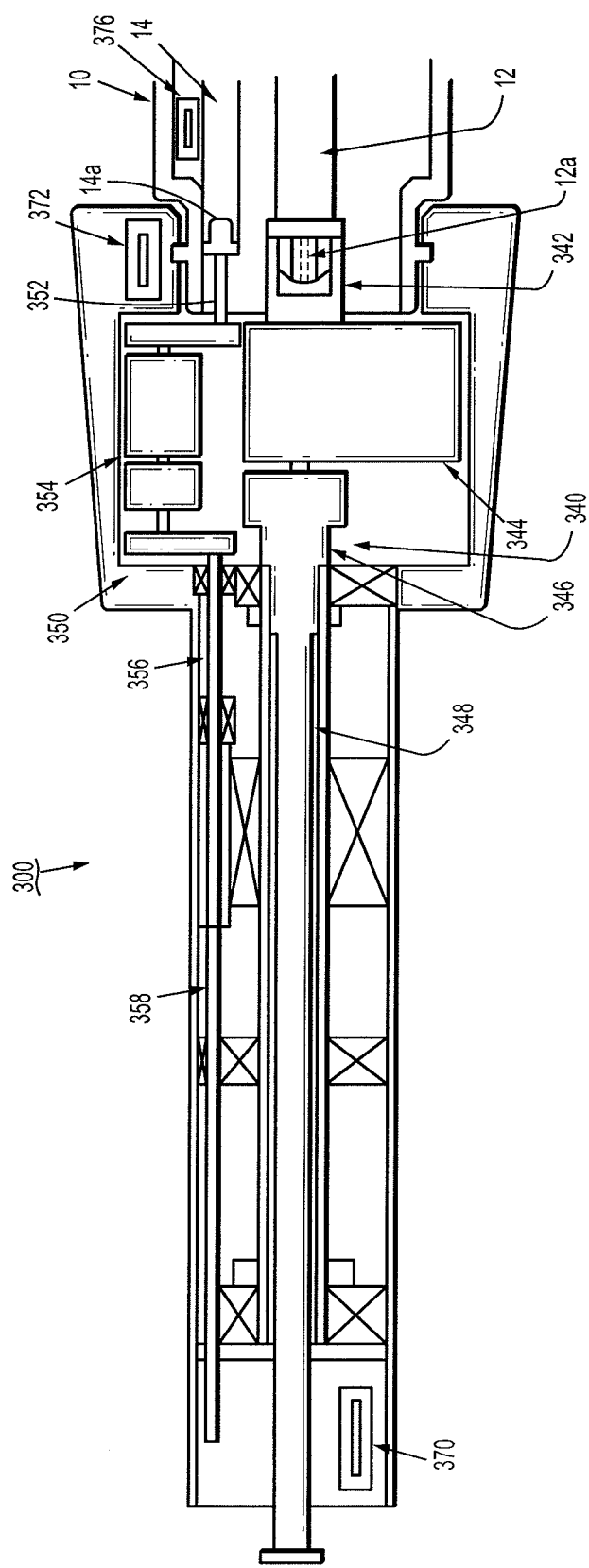
FIG. 35 is a schematic, longitudinal, cross-sectional view of an adapter assembly, in accordance with an embodiment of the present disclosure, shown connected to a distal end of a surgical device.

Turning now to FIG. 35, an adapter assembly 300, in accordance with an embodiment of the present disclosure, is shown connected to or supported on a distal end of surgical device 10. As seen in FIG. 35, adapter assembly 300 includes a first and a second drive converter assembly 340, 350, respectively. Each drive converter assembly 340, 350 is configured and adapted to convert a rotation of a respective first and second drive shaft 12, 14 of surgical device 10, into axial translation of respective drive members or the like of adapter assembly 300.

First drive converter assembly 340 includes a proximal coupling 342 configured for selective connection to a distal end 12a of drive shaft 12, a gear system 344 connected to proximal coupling 342 and rotatably supported within a housing of adapter assembly 300, a distal coupling nut 346 connected to a distal end of gear system 344 and rotatably supported on a threaded portion of a first drive shaft 348.

First drive shaft 348 is supported for axial reciprocation within the housing of adapter assembly. First drive shaft 348 includes a threaded proximal end portion threadably coupled to coupling nut 346 and a distal end portion extending from a distal end of the housing of adapter assembly 300. The distal end portion of first drive shaft 348 defines a connection member configured and adapted for selective engagement with an axially translatable drive member of any of end effectors 20, 30 and/or 40.

In operation, as coupling nut 346 is rotated due to a rotation of gearing system 344 and first drive shaft 12 of surgical device 10, first drive shaft 348 is caused to be translated axially relative to coupling nut 346. Accordingly, as first drive shaft 348 is translated axially, with the distal connection member thereof connected to a drive member of any of end effectors 20, 30 and/or 40, first drive shaft 348 causes concomitant axial translation of the drive member of any of end effectors 20, 30 and/or 40 to effectuate an operation and/or function thereof, such as, for example, the firing of the end effector or the like.

Second drive converter assembly 350 includes a proximal coupling 352 configured for selective connection to a distal end 14a of drive shaft 14, a gear system 354 connected to proximal coupling 352 and rotatably supported within a housing of adapter assembly 300, a distal coupling member 356 connected to a distal end of gear system 354 and rotatably supported on a threaded portion of a second drive shaft 358.

Second drive shaft 358 is supported for axial translation within the housing of adapter assembly. Second drive shaft 358 includes a threaded proximal end portion threadably coupled to coupling member 356 and a distal end portion extending through the housing of adapter assembly 300. The distal end portion of second drive shaft 358 defines a connection member configured and adapted for selective engagement with an axially translatable drive member of any of end effectors 20, 30 and/or 40.

In operation, as coupling member 356 is rotated due to a rotation of gearing system 354 and second drive shaft 14 of surgical device 10, second drive shaft 358 is caused to be translated axially relative to coupling member 356. Accordingly, as drive shaft 348 is translated axially, with the distal connection member thereof connected to a drive member of any of end effectors 20, 30 and/or 40, second drive shaft 358 causes concomitant axial translation of the drive member of any of end effectors 20, 30 and/or 40 to effectuate an operation and/or function thereof, such as, for example, the firing of the end effector or the like.

As seen in FIG. 35, adapter assembly 300 includes a distal recognition sensor 370 supported near a distal end of outer tube 306 or the like. Distal recognition sensor 370 is configured and adapted to identify and/or recognize the end effectors that are attached to the distal end of adapter assembly 300.

Adapter assembly 300 may further include a proximal recognition sensor 372 supported near a proximal end of adapter assembly 300. Proximal recognition sensor 372 may be in communication with distal recognition sensor 370, to thereby transmit the identity and/or recognition parameters of the end effectors that are attached to the distal end of adapter assembly 300, to a sensor or monitor 376 supported in surgical device 10.

In accordance with an embodiment of the present disclosure, as seen in FIG. 36, it is contemplated that an adapter assembly may be provided that includes a first rotatable drive shaft and a second rotatable drive shaft, wherein each of the first and second rotatable drive shafts is configured and dimensioned to operatively interconnect a respective first and second rotatable drive shaft of surgical device 10 to a respective first and second rotatable drive member of end effector 50.

Turning now to FIGS. 37-51, an adapter assembly, configured and adapted to operatively interconnect and couple any one of a number of end effectors to surgical device 10, in accordance with another embodiment of the present disclosure, is generally designated as adapter assembly 400.

Adapter assembly 400 includes a knob housing 402 configured and adapted to connect to a nose of surgical device 10. Adapter assembly 400 further includes an outer tube 406 extending from a distal end of knob housing 402. Knob housing 402 and outer tube 406 are configured and dimensioned to house the components of adapter assembly 400. Outer tube 406 may be dimensioned such that outer tube may pass through a typical trocar port, cannula or the like.

As seen in FIGS. 37, 39-41 and 43-51, adapter assembly 400 includes a surgical device drive coupling assembly 410. Drive coupling assembly 410 includes a distal drive coupling housing 412 and a proximal drive coupling housing 422 rotatably supported in knob housing 402. Drive coupling assembly 410 rotatably supports a first and a second rotatable proximal drive shaft 414 and 415, respectively (see FIGS. 45-48), and a third rotatable proximal drive shaft 416 (see FIGS. 40, 47 and 48) therein.

Drive coupling housing 422 is configured to rotatably support first, second and third coupling sleeves 418, 419 and 420, respectively. Each of coupling sleeves 418-420 is configured to mate with a distal end of respective first, second and third drive shafts (not shown) of surgical device 10. Each of coupling sleeves 418-420 is further configured to mate with a proximal end of respective first, second and third proximal drive shafts 414, 415 and 416.

It is contemplated that drive coupling assembly 410 includes a first, a second and a third biasing member 424, 425 and 426 disposed distally of respective first, second and coupling sleeves 418-420. Each of biasing members 424, 425 and 426 is disposed about respective first, second and third rotatable proximal drive shaft 414, 415 and 416. Biasing members 424-426 act on respective coupling sleeves 418-420 to help maintain coupling sleeves 418-420 engaged with the distal end of respective drive shafts (not shown) of surgical device 10 when adapter assembly 400 is connected to surgical device 10.

In particular, first, second and third biasing members 424, 425 and 426 function to bias respective coupling sleeves 418, 419 and 420 in a proximal direction. In this manner, during assembly of adapter assembly 400 to surgical device 10, if first, second and or third coupling sleeves 418, 419 and/or 420 is/are misaligned with the driving shafts of surgical device 10, first, second and/or third biasing member(s) 424, 425 and/or 426 are compressed. Thus, when the drive motor of surgical device 10 is engaged, the driving shaft of surgical device 10 will rotate and first, second and/or third biasing member(s) 424, 425 and/or 426 will cause respective first, second and/or third coupling sleeve(s) 418, 419 and/or 420 to slide back proximally, effectively coupling the drive rods of surgical device 10 to first, second and/or third proximal drive shaft(s) 414, 415 and 416 of drive coupling assembly 410.

Adapter assembly 400 includes a first, a second and a third drive converter assembly 440, 450, 460, respectively. Each drive converter assembly 440, 450, 460 is configured and adapted to convert a rotation of a respective first, second and third drive shaft (not shown) of surgical device 10 into axial translation of respective drive members or the like of adapter assembly 400.

Figure 39:
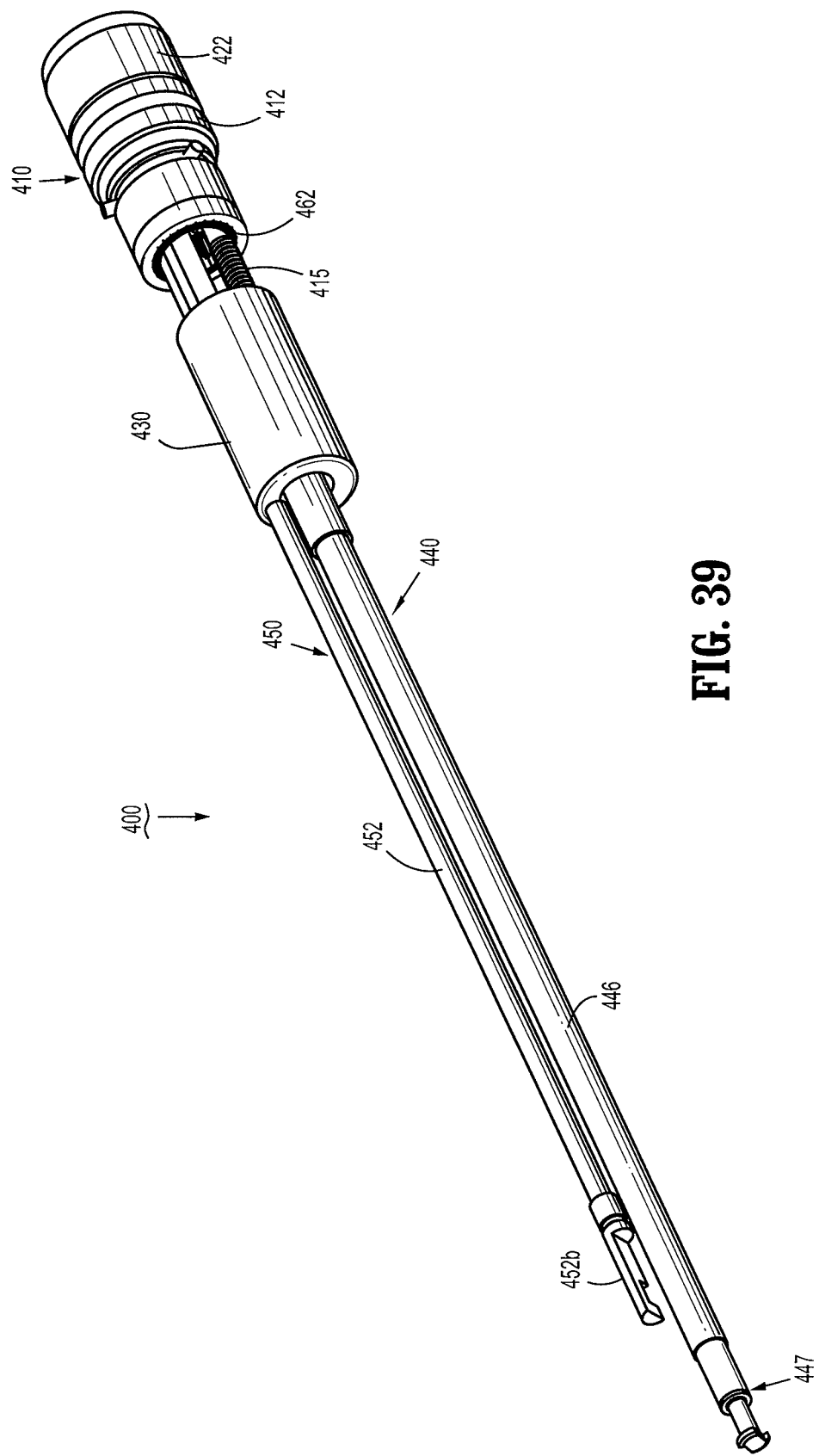
FIG. 39 is a front perspective view of the adapter assembly of FIGS. 37 and 38, with an outer tube removed therefrom.
Figure 40:
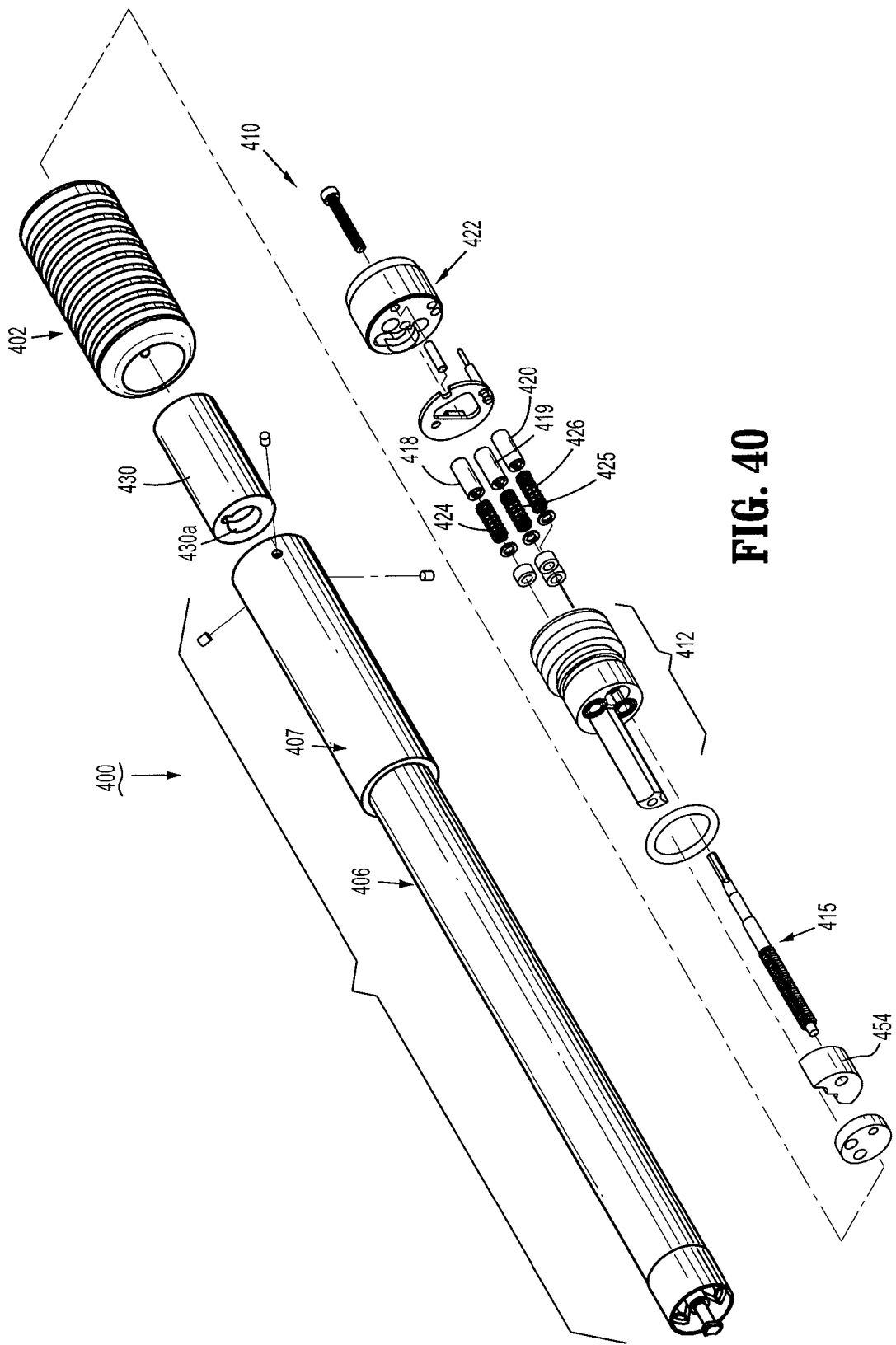
FIG. 40 is a perspective view of the adapter assembly of FIGS. 37 and 38, illustrated with parts of a proximal portion thereof partially separated.
Figure 41:
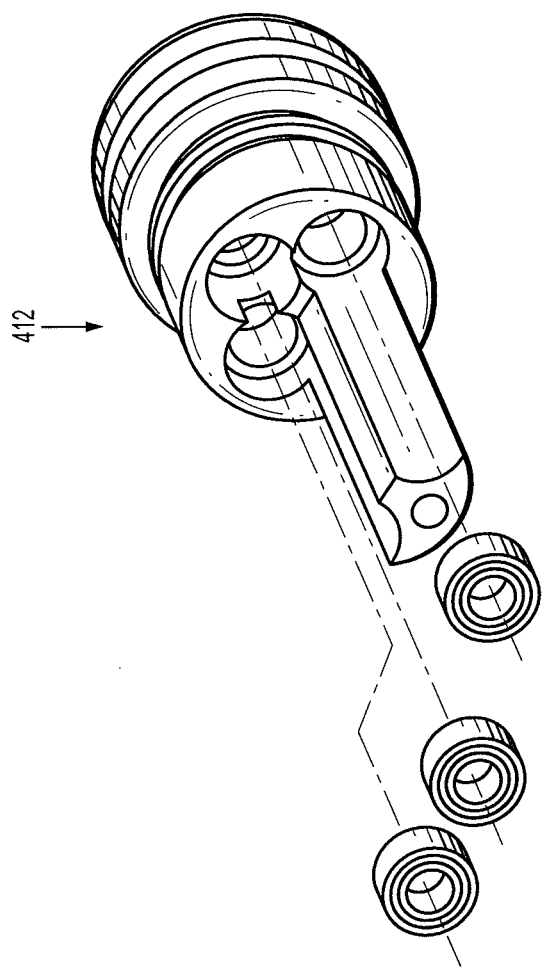
FIG. 41 is an enlarged view of a support hub, illustrated with parts separated, of the adapter assembly of FIGS. 37 and 38.
Figure 42:
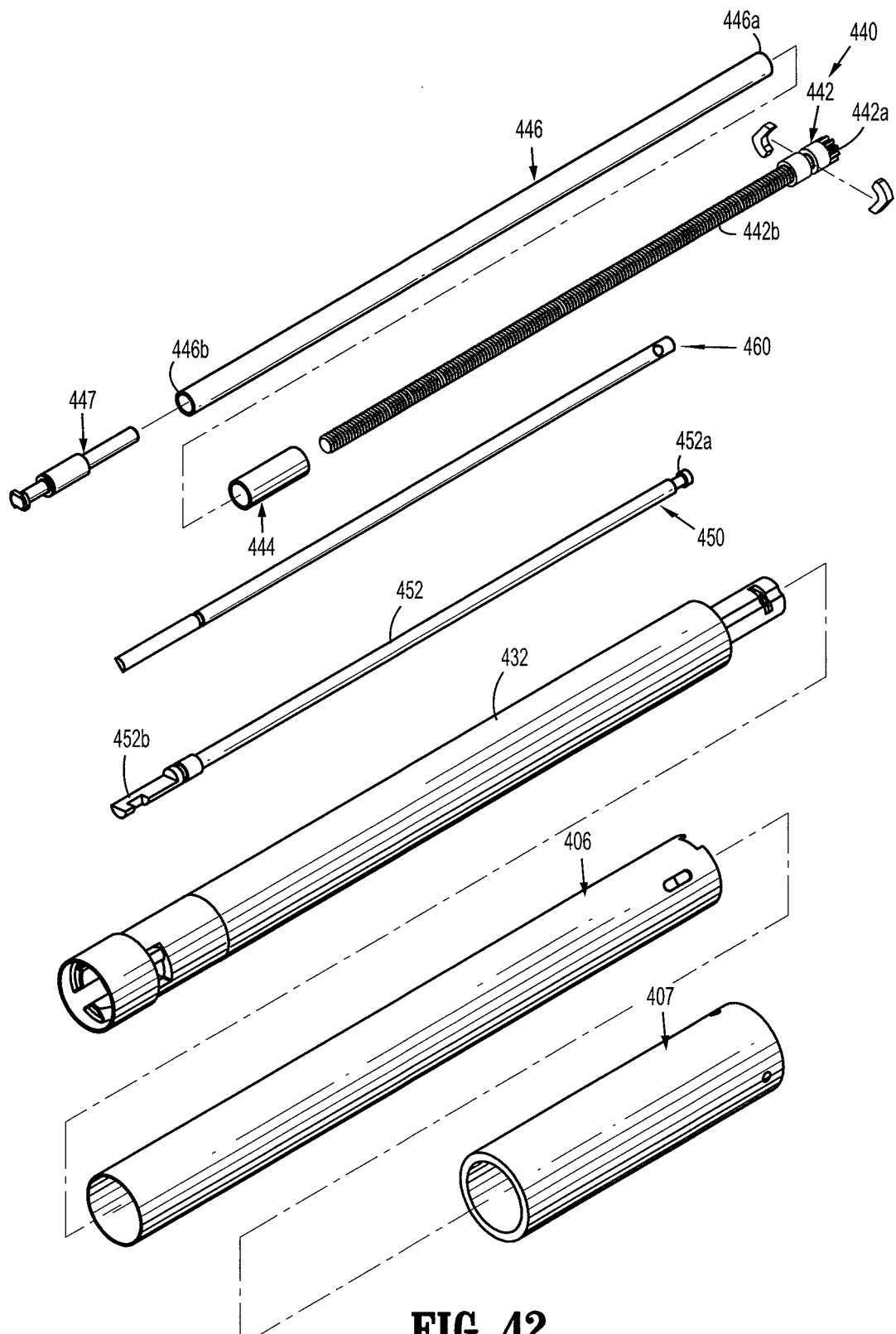
FIG. 42 is a perspective view of the adapter assembly of FIGS. 37 and 38, illustrated with parts of a distal portion thereof partially separated.

As seen in FIGS. 39, 40 and 42, adapter assembly 400 includes a proximal tubular housing 430 rotatably and slidably disposed within proximal outer tube 407, and a distal housing 432 disposed at least partially within outer tube 406. Proximal tubular housing 430 defines a longitudinally extending lumen 430a formed therethrough. Proximal tubular housing 430 receives a distal end of distal drive coupling housing 412 of drive coupling assembly 410. A distal end of distal housing 432 may be configured and adapted to selectively engage and couple with a proximal end of any of the end effectors 20, 30 and/or 40. It is contemplated that the distal end of distal housing 432 may be configured to receive the proximal end of any of the end effectors 20, 30 and/or 40 is a bayonet-type configuration or coupling, or any other coupling known by one having skill in the art.

As seen in FIGS. 42-47, first drive converter assembly 440 includes a first distal drive shaft 442 rotatably supported within proximal tubular housing 430 and distal housing 432. First distal drive shaft 442 includes a spur gear 442a supported on a proximal end thereof which is configured for connection to a spur gear 414a of first rotatable proximal drive shaft 414. First distal drive shaft 442 further includes a distal end portion 442b having a threaded outer profile or surface.

First drive converter assembly 440 further includes a drive coupling nut 444 rotatably coupled to threaded distal end portion 442a of first distal drive shaft 442, and which is slidably disposed within proximal tubular housing 430 and distal housing 432. Drive coupling nut 444 is prevented from rotation as first distal drive shaft 442 is rotated. In this manner, as first distal drive shaft 442 is rotated, drive coupling nut 444 is translated through and/or along proximal tubular housing 430 and distal housing 432.

First drive converter assembly 440 further includes a drive tube 446 surrounding first distal drive shaft 442 and having a proximal end portion 446a connected to drive coupling nut 444 and a distal end portion 446b extending beyond a distal end of first distal drive shaft 442. Distal end portion 446b of drive tube 446 supports a connection member 447 configured and dimensioned for selective engagement with an axially translatable drive member of any of end effectors 20, 30 and/or 40.

In operation, as first rotatable proximal drive shaft 414 is rotated, due to a rotation of first coupling sleeve 418, as a result of the rotation of the first drive shaft of surgical device 10, spur gear 414a of first rotatable proximal drive shaft 414 engages spur gear 442a of first distal drive shaft 442 thereby causing first distal drive shaft 442 to rotate. As first distal drive shaft 442 is rotated, drive coupling nut 444 is caused to be translated axially along first distal drive shaft 442.

As drive coupling nut 444 is caused to be translated axially along first distal drive shaft 442, drive tube 446 is caused to be translated axially relative to distal housing portion 432. Accordingly, as drive tube 446 is translated axially, with connection member 447 connected thereto and connected to a drive member of any of end effectors 20, 30 and/or 40, drive tube 446 causes concomitant axial translation of the drive member of any of end effectors 20, 30 and/or 40 to effectuate an operation and/or function thereof, such as, for example, the firing of the end effector or the like.

With reference to FIGS. 39, 40 and 42-47, second drive converter assembly 450 includes a second distal drive shaft 452 rotatably supported within distal housing 432. Second distal drive shaft 452 includes a proximal end portion 452*a* connected to proximal tubular housing 430. Second distal drive shaft 452 further includes a distal end portion 452*b* configured and dimensioned for selective engagement with an axially translatable drive member of any of end effectors 20, 30 and/or 40.

Figure 47:
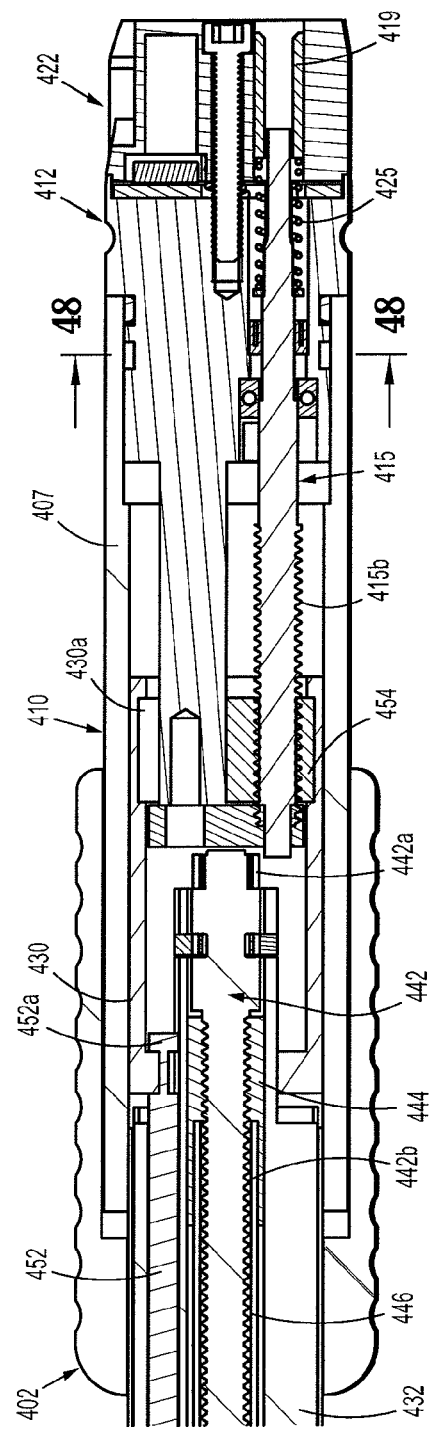
FIG. 47 is an enlarged view of the indicated area of detail of FIG. 46.
Figure 48:
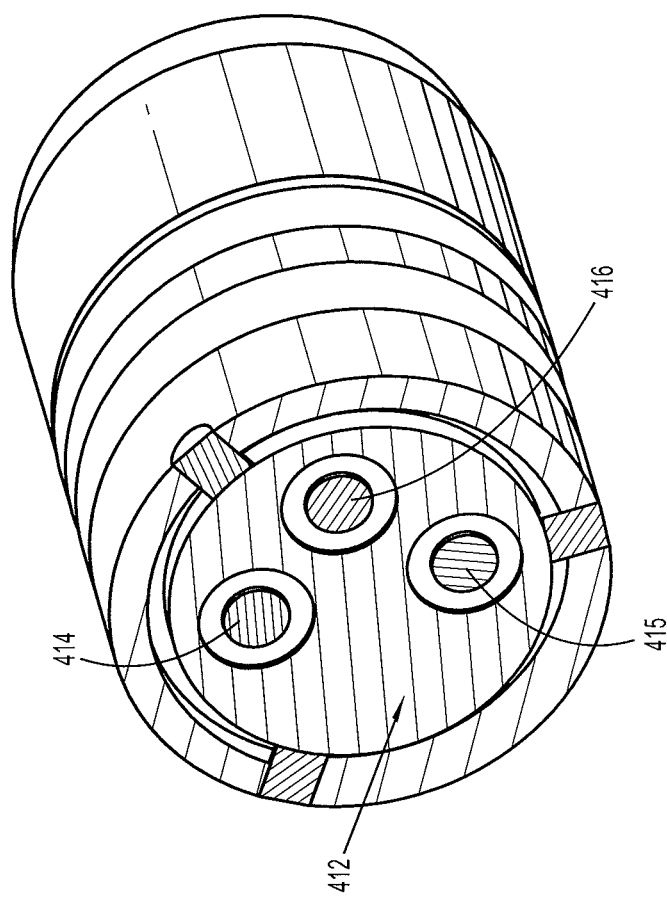
FIG. 48 is a cross-sectional view as taken through 48-48 of FIG. 47.
Figure 49:
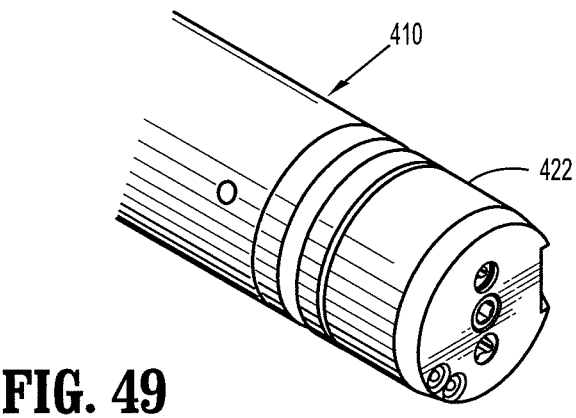
FIG. 49 is a rear perspective view of a proximal end portion of the adapter assembly of FIGS. 37 and 38.

Second drive converter assembly 450 further includes a coupling nut 454 rotatably supported within an annular race or recess 430*a* formed in proximal tubular housing 430 (see FIG. 47). Coupling nut 454 is threadably connected to a threaded distal end portion 415*b* of second rotatable proximal drive shaft 415. In this manner, as second rotatable proximal drive shaft 415 is rotated, coupling nut 454 is translated relative to second rotatable proximal drive shaft 415 thereby causing proximal tubular housing 430 to also translate.

In operation, as second rotatable proximal drive shaft 415 is rotated, due to a rotation of second coupling sleeve 419, as a result of the rotation of the second drive shaft of surgical device 10, coupling nut 454 is caused to be translated axially along second rotatable proximal drive shaft 415.

As coupling nut 454 is caused to be translated axially along second rotatable proximal drive shaft 415, proximal tubular housing 430 to also caused to be translated axially relative to distal housing portion 432. Accordingly, as proximal tubular housing 430 is translated axially, second distal drive shaft 452 is caused to be translated axially. In this manner, with distal end portion 452*b* thereof connected to a drive member of any of end effectors 20, 30 and/or 40, second distal drive shaft 452 causes concomitant axial translation of the drive member of any of end effectors 20, 30 and/or 40 to effectuate an operation and/or function thereof, such as, for example, the firing of the end effector or the like.

Figure 45:
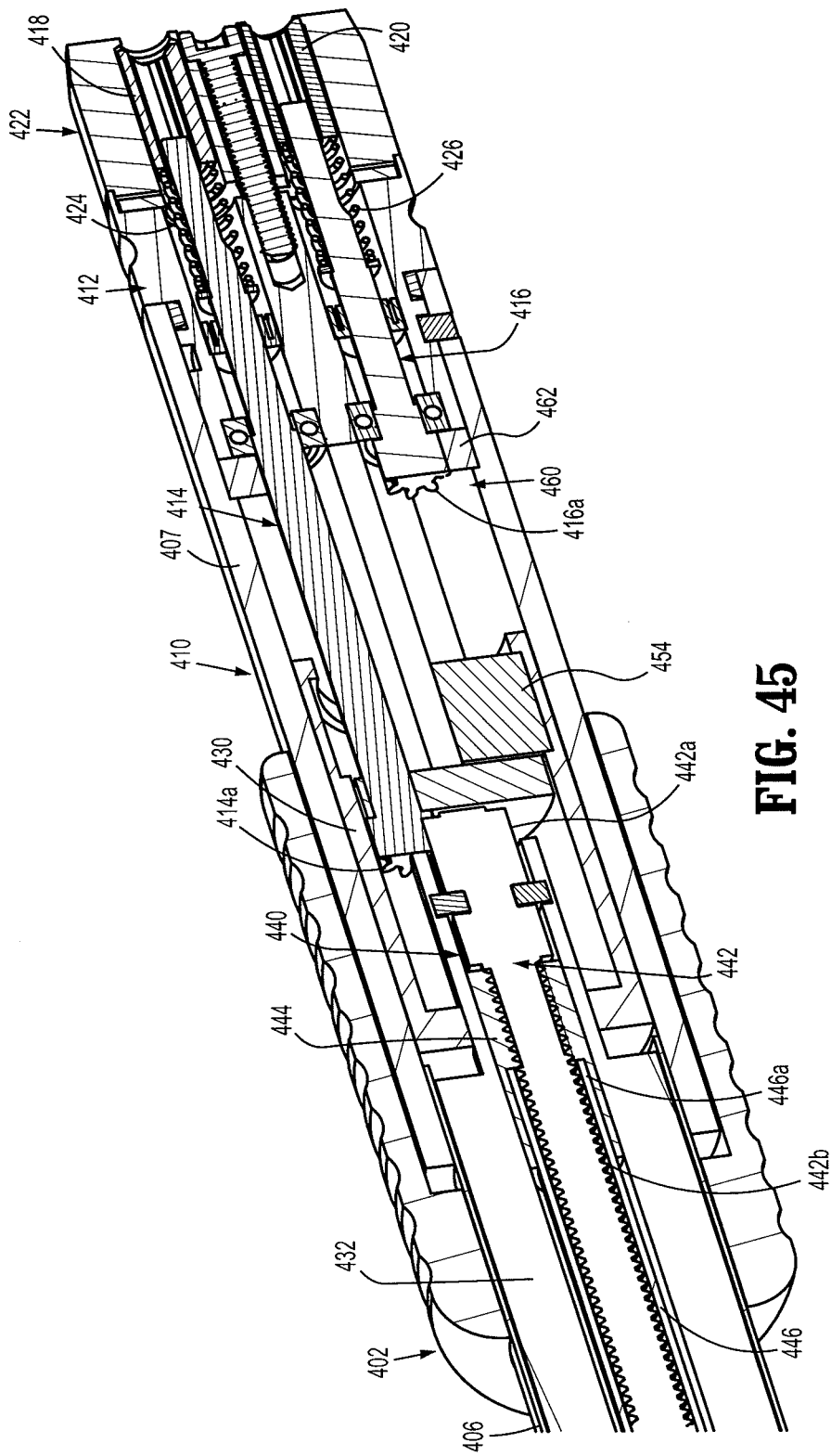
FIG. 45 is a perspective view of the indicated area illustrated in FIG. 44.
Figure 46:
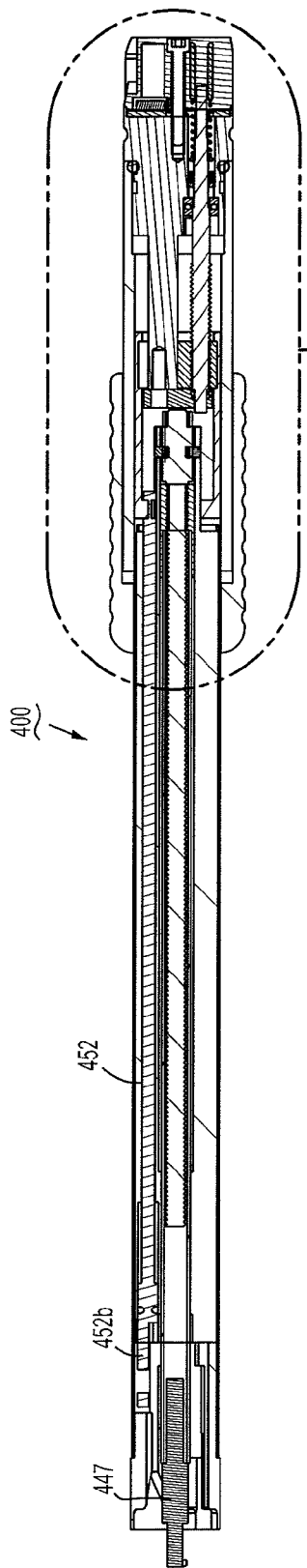
FIG. 46 is a further longitudinal cross-section of the adapter assembly of FIGS. 37 and 38, as taken through 46-46 of FIG. 37.

With reference to FIGS. 39 and 45, third drive converter assembly 460 includes a ring gear 462 connected to an inner surface of proximal outer tube 407 and extending radially therearound. Third drive converter assembly 460 further includes a spur gear 416*a* supported on third rotatable proximal drive shaft 416 and which is configured and located for mating engagement with ring gear 462.

In operation, as third rotatable proximal drive shaft 416 is rotated, due to a rotation of third coupling sleeve 420, as a result of the rotation of the third drive shaft of surgical device 10, spur gear 416*a* of third rotatable proximal drive shaft 416 engages ring gear 462 thereby causing ring gear 462 to rotate. As ring gear 462 is rotated, ring gear 462 causes proximal outer tube 407 to rotate. As proximal outer tube 407 is rotated, distal outer tube 406 is also rotated and so too is any of end effectors 20, 30 and/or 40 that may be coupled thereto.

Figure 50:
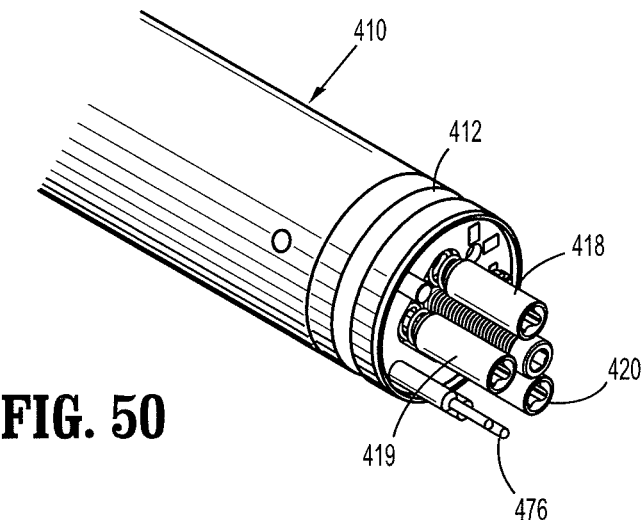
FIG. 50 is a rear perspective view of the proximal end portion of the adapter assembly shown in FIG. 49, with a cap of FIGS. 37 and 38.
Figure 51:
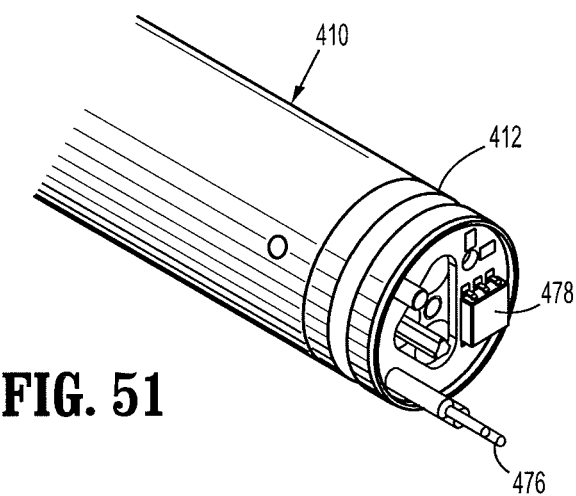
FIG. 51 is a rear perspective view of the proximal end portion of the adapter assembly shown in FIG. 50 with components removed therefrom.
Figure 52:
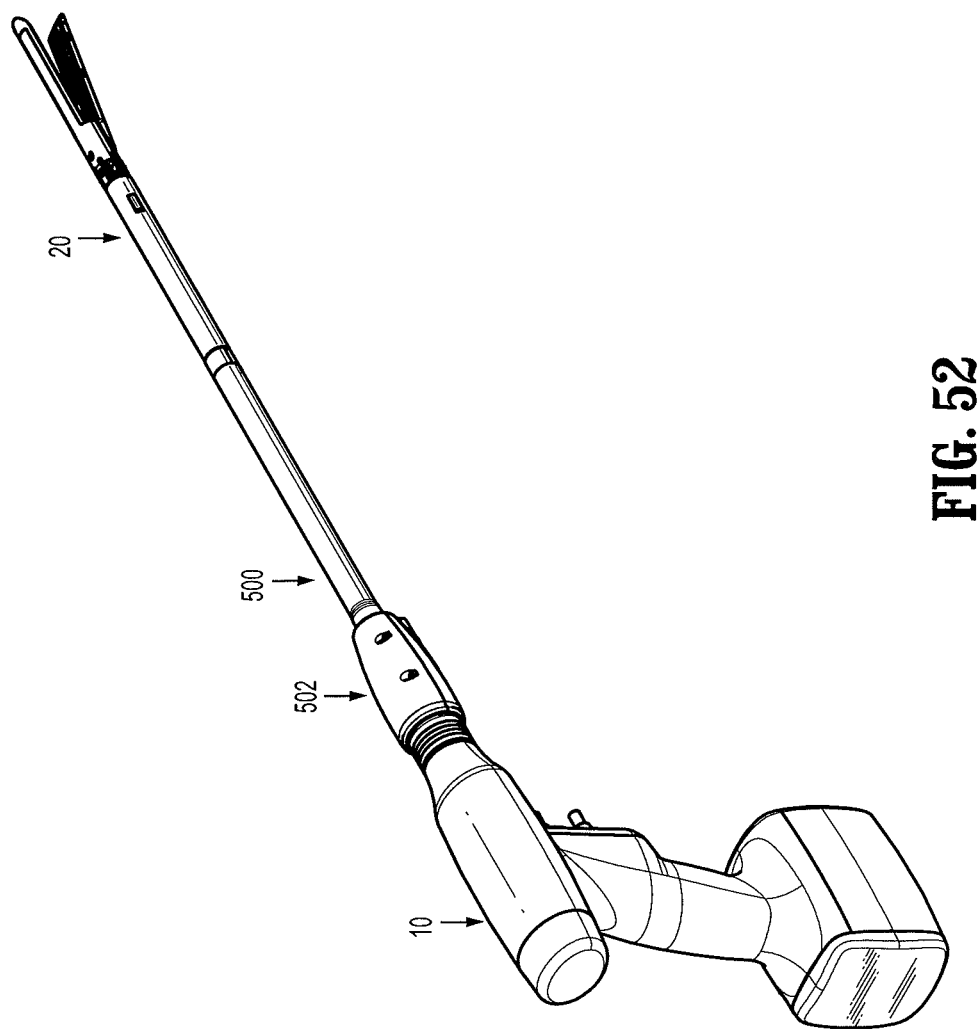
FIG. 52 is a rear, perspective view of an exemplary surgical device and/or handle assembly supporting an adapter assembly according to another embodiment of the present disclosure and illustrating an exemplary end effector supported on an end of the adapter assembly.
Figure 53:
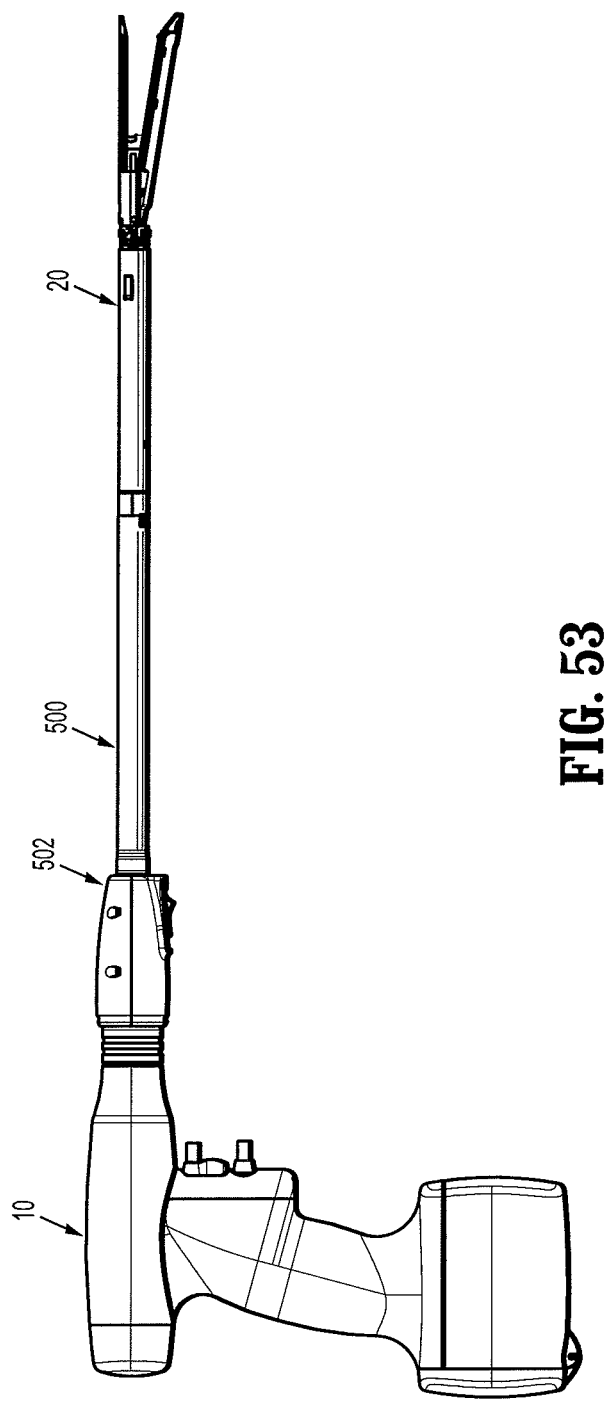
FIG. 53 is a side, elevational view of the surgical device, adapter assembly and end effector shown in FIG. 52.
Figure 54:
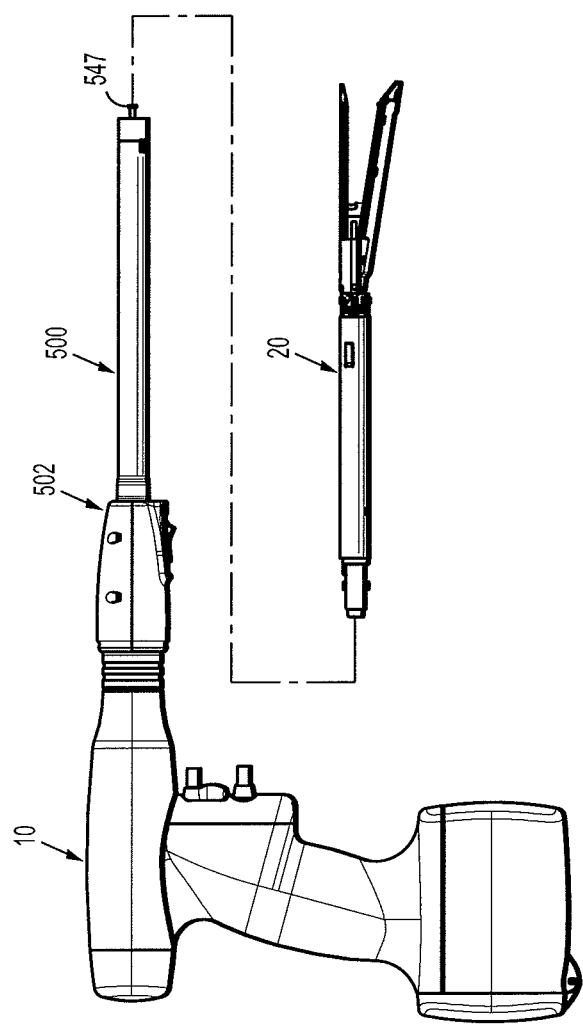
FIG. 54 is a perspective view of the surgical device of FIGS. 52 and 53, illustrating the adapter assembly connected thereto and illustrating the end effector disconnected from the adapter assembly.
Figure 55:
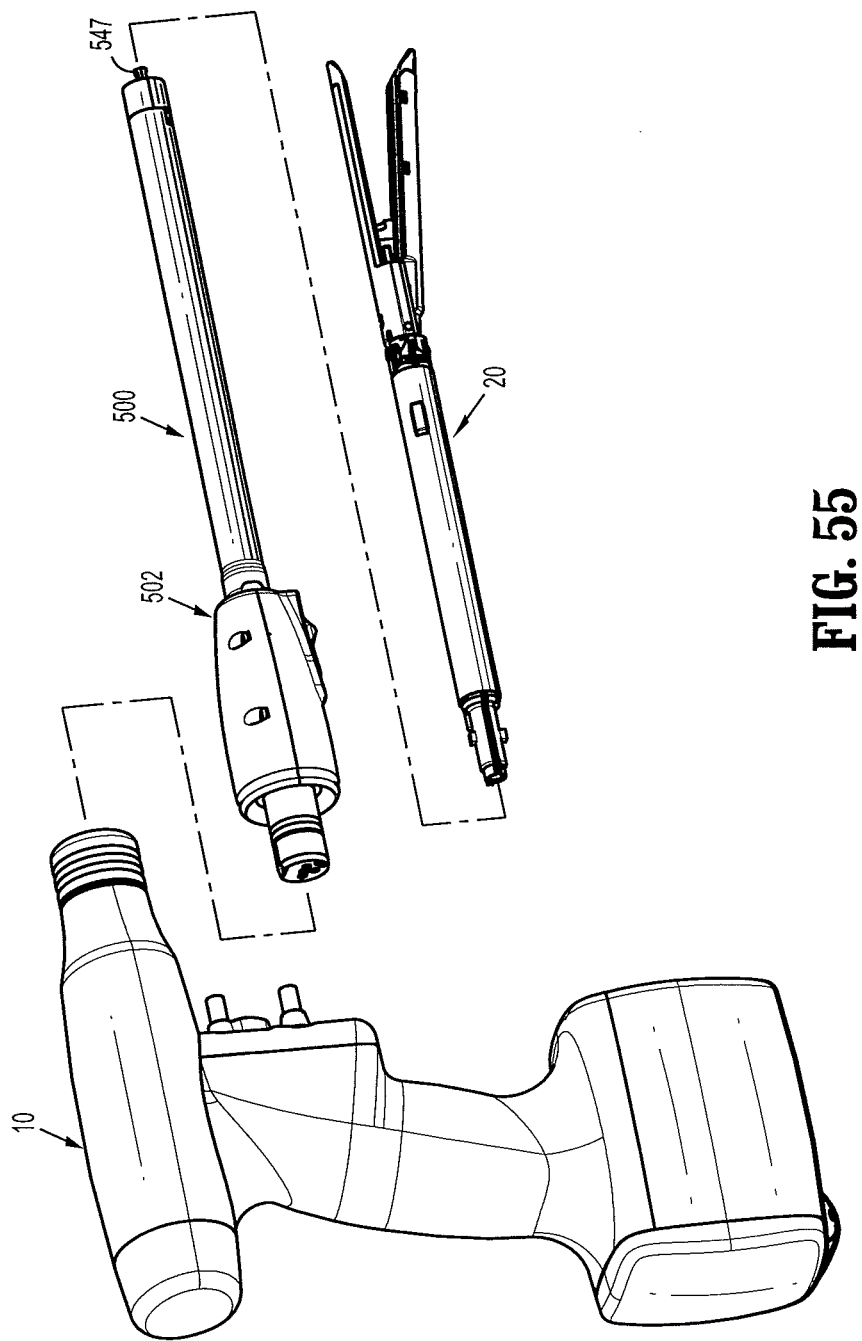
FIG. 55 is a perspective view of the surgical device of FIGS. 52-54, illustrating the adapter assembly disconnected therefrom and illustrating the end effector disconnected from the adapter assembly.

As seen in FIGS. 50 and 51, adapter assembly 400 may include at least one electrical contact 476, in the form of a pin, for electrical connection to a corresponding plug of the surgical device 10. As seen in FIG. 51, adapter assembly 400 may further include at least one conductive, optical, magnetic or radio-frequency identification device 478 for electrical connection to a corresponding plug of the surgical device 10.

Turning now to FIGS. 52-66, an adapter assembly, configured and adapted to operatively interconnect and couple any one of a number of end effectors (here, end effector 20 being shown) to surgical device 10, in accordance with another embodiment of the present disclosure, is generally designated as adapter assembly 500.

Adapter assembly 500 includes a knob housing 502 configured and adapted to connect to a nose of surgical device 10. Adapter assembly 500 further includes an outer tube 506 extending from a distal end of knob housing 502. Knob housing 502 and outer tube 506 are configured and dimensioned to house the components of adapter assembly 500. Outer tube 506 may be dimensioned such that outer tube 506 may pass through a typical trocar port, cannula or the like.

As seen in FIGS. 58-60 and 64-65, adapter assembly 500 includes a surgical device drive coupling assembly 510. Drive coupling assembly 510 includes a distal drive coupling housing 512 and a proximal drive coupling housing 522 rotatably supported in knob housing 502. Drive coupling assembly 510 rotatably supports a first rotatable proximal drive shaft 514, a second rotatable proximal drive shaft 515, and a third rotatable proximal drive shaft 516 therein.

Proximal drive coupling housing 522 is configured to rotatably support first, second and third coupling sleeves 518, 519 and 520, respectively. Each of coupling sleeves 518-520 is configured to mate with a distal end of respective first, second and third drive shafts (not shown) of surgical device 10. Each of coupling sleeves 518-520 is further configured to mate with a proximal end of respective first, second and third proximal drive shafts 514, 515 and 516.

It is contemplated that proximal drive coupling assembly 510 includes a first, a second and a third biasing member 524, 525 and 526 disposed distally of respective first, second and third coupling sleeves 518-520. Each of biasing members 524, 525 and 526 is disposed about respective first, second and third rotatable proximal drive shaft 514, 515 and 516. Biasing members 524, 525 and 526 act on respective coupling sleeves 518, 519 and 520 to help maintain coupling sleeves 518, 519 and 520 engaged with the distal end of respective drive shafts (not shown) of surgical device 10 when adapter assembly 500 is connected to surgical device 10.

In particular, first, second and third biasing members 524, 525 and 526 function to bias respective coupling sleeves 518, 519 and 520 in a proximal direction. In this manner, during assembly of adapter assembly 500 to surgical device 10, if first, second and or third coupling sleeves 518, 519 and/or 520 is/are misaligned with the driving shafts of surgical device 10, first, second and/or third biasing member(s) 524, 525 and/or 526 are compressed. Thus, when the drive motor of surgical device 10 is engaged, the driving shaft of surgical device 10 will rotate and first, second and/or third biasing member(s) 524, 525 and/or 526 will cause respective first, second and/or third coupling sleeve(s) 518, 519 and/or 520 to slide back proximally, effectively coupling the drive rods of surgical device 10 to first, second and/or third proximal drive shaft(s) 514, 515 and 516 of proximal drive coupling assembly 510.

In addition, each of coupling sleeves 518, 519 and 520 is biased or spring-loaded, such that if one or more of coupling sleeves 518, 519 and 520 is/are misaligned with respect to the corresponding with the driving shafts of surgical device 10, while adapter assembly 500 is mated to surgical device 10, biasing member(s) 524, 525 and 526, biasing respective coupling sleeves 518, 519 and 520 proximally, compress and the respective coupling sleeves 518, 519 and 520 is/are allowed to move distally. Upon calibration of surgical device 10, each of the driving shafts of surgical device 10 is rotated and the bias on the coupling sleeves 518, 519 and 520 properly seats the coupling sleeves 518, 519 and 520 over the respective driving shaft of surgical device 10 when the proper alignment is reached.

Adapter assembly 500 includes a first, a second and a third drive converter assembly 540, 550, 560, respectively. Each drive converter assembly 540, 550, 560 is configured and adapted to convert a rotation of a respective first, second and third drive shaft (not shown) of surgical device 10 into axial translation of respective drive members or the like of adapter assembly 500.

As seen in FIGS. 60, 61 and 63-65, first drive converter assembly 540 includes a first distal drive shaft 542 rotatably supported within housing 502 and outer tube 506. A proximal end of first distal drive shaft 542 is keyed to a spur gear 542a which is configured for connection to a spur gear 514a of first rotatable proximal drive shaft 514. First distal drive shaft 542 further includes a distal end portion 542b having a threaded outer profile or surface.

First drive converter assembly 540 further includes a drive coupling nut 544 rotatably coupled to threaded distal end portion 542b of first distal drive shaft 542, and which is slidably disposed within outer tube 506. Drive coupling nut 544 is keyed to outer tube 506 or the like so as to be prevented from rotation as first distal drive shaft 542 is rotated. In this manner, as first distal drive shaft 542 is rotated, drive coupling nut 544 is translated through and/or along outer tube 506.

First drive converter assembly 540 further includes a drive tube 546 surrounding first distal drive shaft 542 and having a proximal end portion connected to drive coupling nut 544 and a distal end portion extending beyond a distal end of first distal drive shaft 542. The distal end portion of drive tube 546 supports a connection member 547 (see FIGS. 54-57) configured and dimensioned for selective engagement with an axially translatable drive member of end effector 20.

In operation, as first rotatable proximal drive shaft 514 is rotated, due to a rotation of first coupling sleeve 518, as a result of the rotation of the first drive shaft of surgical device 10, spur gear 514a of first rotatable proximal drive shaft 514 engages first gear 545a of compound gear 545 causing compound gear 545 to rotate. As compound gear 545 rotates, a second gear 545b of compound gear 545 is rotated and thus causes spur gear 542a of first distal drive shaft 542 that is engaged therewith to also rotate thereby causing first distal drive shaft 542 to rotate. As first distal drive shaft 542 is rotated, drive coupling nut 544 is caused to be translated axially along first distal drive shaft 542.

As drive coupling nut 544 is caused to be translated axially along first distal drive shaft 542, drive tube 546 is caused to be translated axially relative to outer tube 506 of adapter assembly 500. Accordingly, as drive tube 546 is translated axially, with connection member 547 connected thereto and connected to a drive member of end effector 20, drive tube 546 causes concomitant axial translation of the drive member of end effector 20 to effectuate an operation and/or function thereof, such as, for example, the firing of the end effector or the like.

As seen in FIGS. 58-60 and 63-66, adapter assembly 500 includes a transmission assembly 580 having a proximal transmission plate 582 disposed distally of distal drive coupling housing 512 and a distal transmission plate 584 disposed distally of proximal transmission plate 582. Proximal transmission plate 582 and distal transmission plate 584 are located at a fixed spaced axial distance from one another. Each of first, second and third proximal drive shafts 514, 515 and 516 extend into transmission assembly 580. Proximal transmission plate 582 defines an annular array of distally oriented, bi-directional gear teeth 582a.

Since the amount of torque required to provide anti-rotation to drive coupling nut 544 is relatively high, in the present embodiment, a lock assembly, clutch assembly or the like 590 is provided to inhibit rotation of outer tube 506 of adapter assembly 500 and of the end effector 20 when relatively large forces are encountered in the end effector 20.

As seen in FIGS. 58-60 and 63-66, clutch assembly 590 includes a rotation coupler 592, in the form of a plate or ring, interposed between proximal transmission plate 582 and distal transmission plate 584. Rotation coupler 592 defines an annular array of proximally oriented, bi-directional gear teeth 592a configured and dimensioned to engage the annular array of distally oriented, bi-directional gear teeth 582a of proximal transmission plate 582. Gear teeth 592a of rotation coupler 592 are arranged in two spaced apart halves defining recesses 592b therebetween. Clutch assembly 590 includes biasing members 594 interposed between rotation coupler 592 and distal transmission plate 584 for providing positive bias to rotation coupler 592 to ensure that gear teeth 592a of rotation coupler 592 remained locked or engaged with gear teeth 582a of proximal transmission plate 582.

Clutch assembly 590 further includes an internal rotation ring gear 596 interposed between proximal transmission plate 582 and rotation coupler 592. Ring gear 596 defines an internal array of gear teeth 596a. Ring gear 596 includes a pair of diametrically opposed, radially extending protrusions 596b projecting form an outer edge thereof. Ring gear 596 further includes cam surfaces 596c configured to engage respective cam surfaces 592c of rotation coupler 592.

In operation, as ring gear 596 is rotated an initial 20° relative to rotation coupler 592, gear teeth 592a of rotation coupler 592 are caused to be separated from gear teeth 582a of proximal transmission plate 582 due to the camming interaction of cam surfaces 596c of ring gear 596 with cam slots 592c of rotation coupler 592. Following the first 20° of rotation, protrusion 596b or ring gear 596 is in abutment with the end wall of recess 592b of rotation coupler 592. Then, as ring gear 596 is rotated an additional 5°, protrusion 596b of ring gear 596 pushes against the end wall of recess 592b of rotation coupler 592, which is connected to housing 502, to rotate thereby causing housing 502 of adapter assembly 500 and thus end effector 20 to rotate. Rotation coupler 592 is keyed to housing 502 thereby transmitting rotation thereof to housing 502 and on to outer tube 506 and end effector 20.

Rotation of ring gear 596 is accomplished through rotation of third rotatable proximal drive shaft 516 and actuation of third drive converter assembly 560. In particular, as third rotatable proximal drive shaft 516 is rotated, due to a rotation of third coupling sleeve 520, as a result of the rotation of the third drive shaft of surgical device 10, spur gear 516a of third rotatable proximal drive shaft 516 engages an intermediate spur gear 562 of third drive converter assembly 560. As intermediate spur gear 562 is rotated, rotation is transmitted to ring gear 596.

As mentioned above, as ring gear 596 is rotated, ring gear 596 interacts with rotation coupler 592 to cause rotation coupler 592 to rotate and to transmit rotation to housing 502, outer tube 506 and end effector 20.

With reference to FIGS. 60, 61 and 63-65, second drive converter assembly 550 includes a second distal drive shaft 552 supported within housing 502 and outer tube 506 of adapter 500. Second distal drive shaft 552 includes a proximal end portion 552a connected to an articulation link 554. Second distal drive shaft 552 further includes a distal end portion configured and dimensioned for selective engagement with an axially translatable drive member of end effector 20. Articulation link 554 defines a lip 554a configured for receipt in an annular groove 556a of a coupling nut 556. This arrangement enables articulation link 554 to rotate around coupling nut 556 and still be able to transmit axial movement as a result of the rotation of threaded distal end portion 515b of proximal drive shaft 515. Second drive converter assembly 550 may include an inner ring 557a configured to keep articulation link 554 constrained to or connected to coupling nut 556. Second drive converter assembly 550 may further include an outer ring 557b at least partially surrounding inner ring 557a and rotatably connected thereto via complementary annular rings and grooves thereby allowing relative rotation with respect to one another and still providing axial linear movement.

Second drive converter assembly 550 further includes a coupling nut 556 rotatably supported within an annular race or recess formed in housing 502. Coupling nut 556 is threadably connected to a threaded distal end portion 515b of second rotatable proximal drive shaft 515. In this manner, as second rotatable proximal drive shaft 515 is rotated, coupling nut 556 is translated relative to second rotatable proximal drive shaft 515 thereby causing articulation link 554 and second distal drive shaft 552 to also translate.

In operation, as second rotatable proximal drive shaft 515 is rotated, due to a rotation of second coupling sleeve 519, as a result of the rotation of the second drive shaft of surgical device 10, coupling nut 554 is caused to be translated axially along second rotatable proximal drive shaft 515.

As coupling nut 554 is caused to be translated axially along second rotatable proximal drive shaft 515, second distal drive shaft 552 is caused to be translated axially. In this manner, with a distal end portion of second distal drive shaft 552 connected to a drive member of end effector 20, second distal drive shaft 552 causes concomitant axial translation of the drive member of end effector 20 to effectuate an operation and/or function thereof, such as, for example, an articulation of end effector 20.

Figure 62:
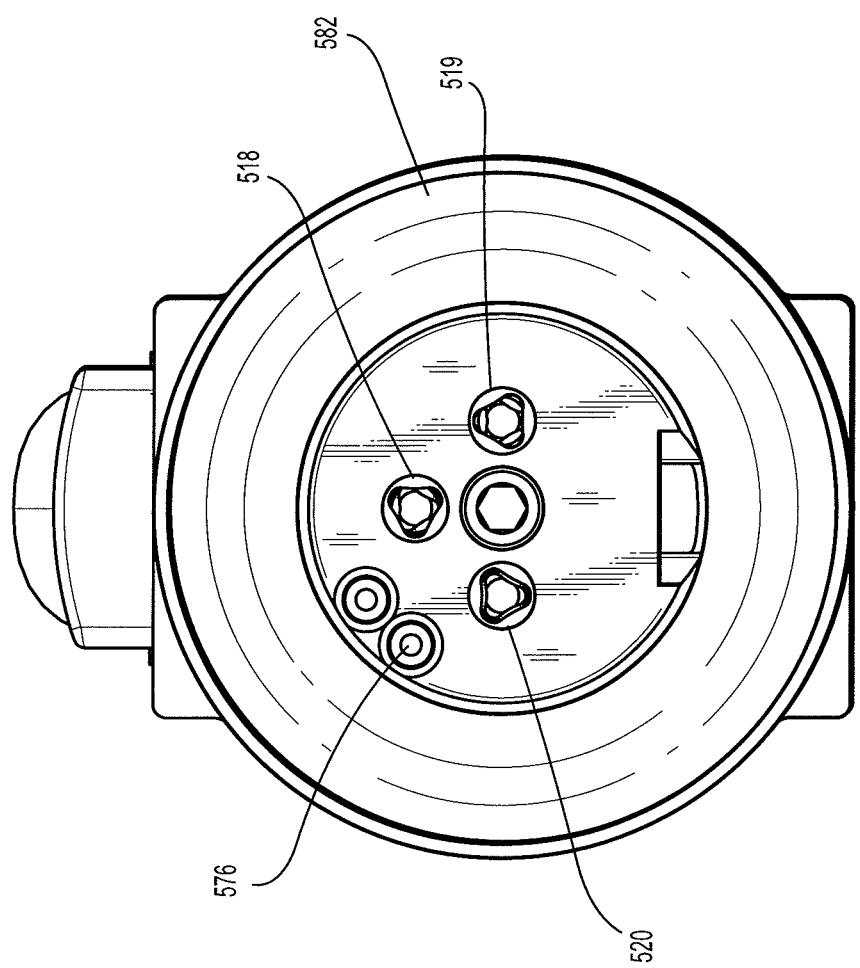
FIG. 62 is a proximal, end view of a clutch assembly of the adapter assembly of FIGS. 52-59.
Figure 63:
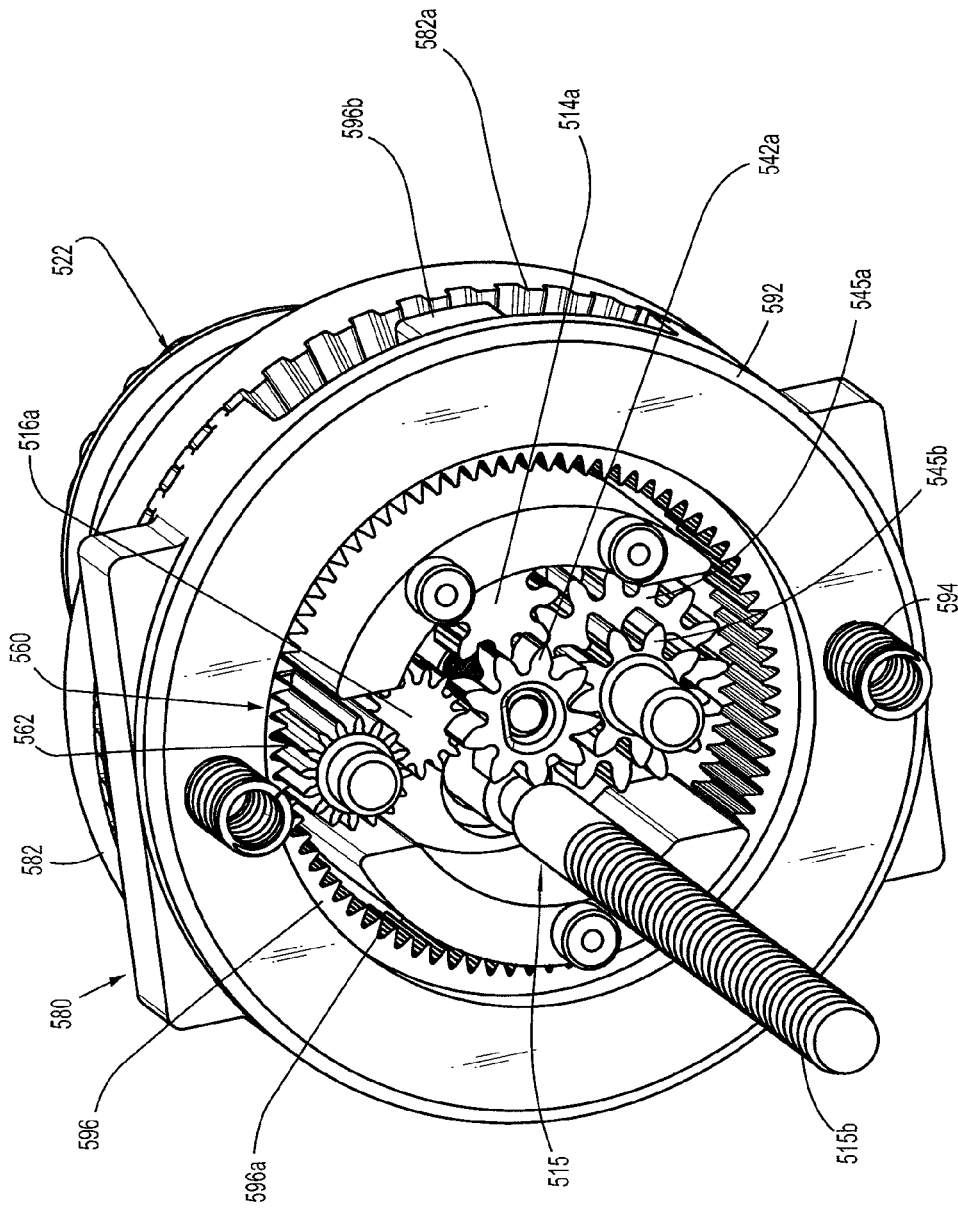
FIG. 63 is a distal, perspective view of the clutch assembly of FIG. 62.
Figure 64:
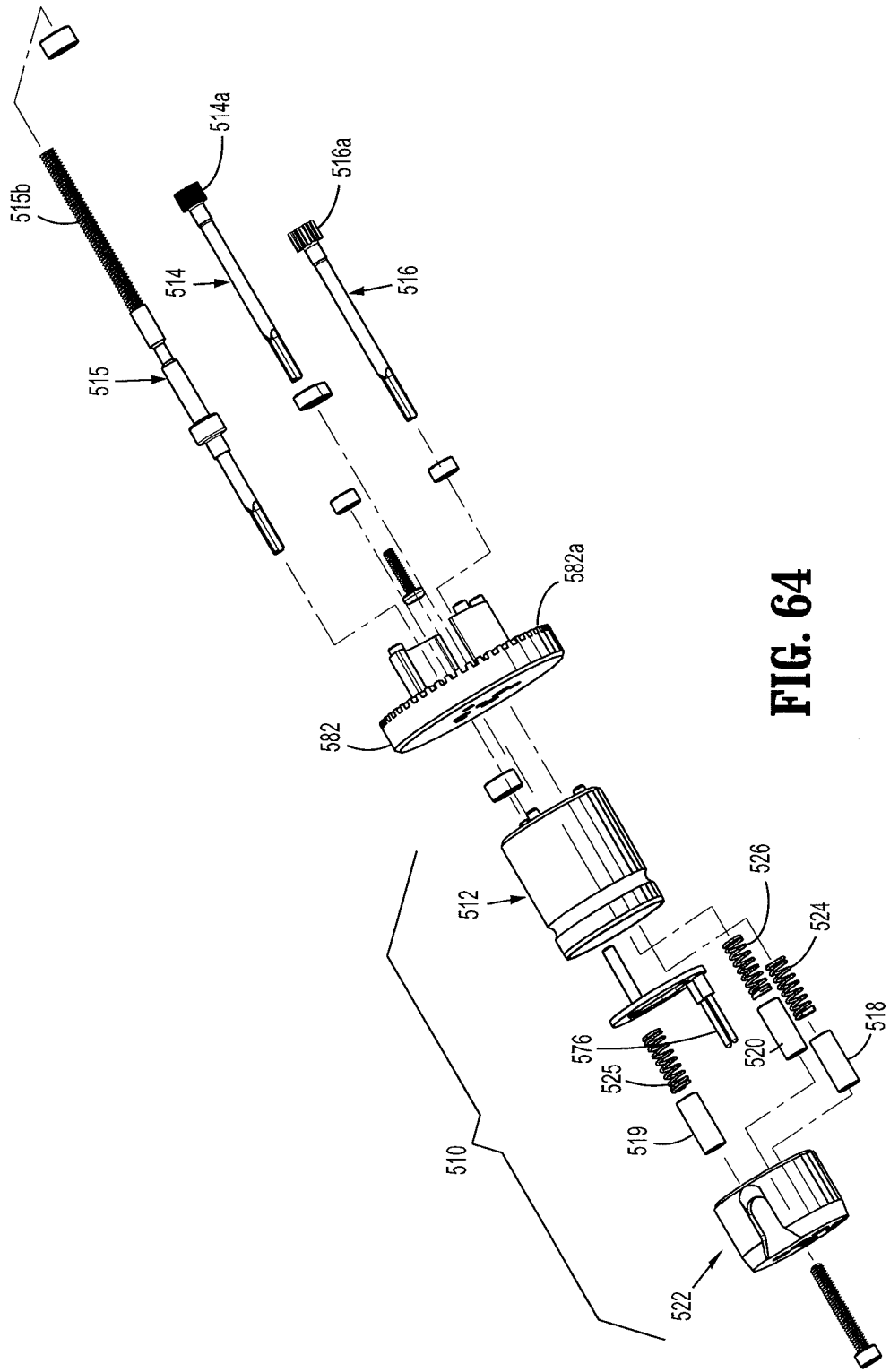
FIG. 64 is a perspective view of a drive coupling assembly of the adapter assembly of FIGS. 52-63.
Figure 65:
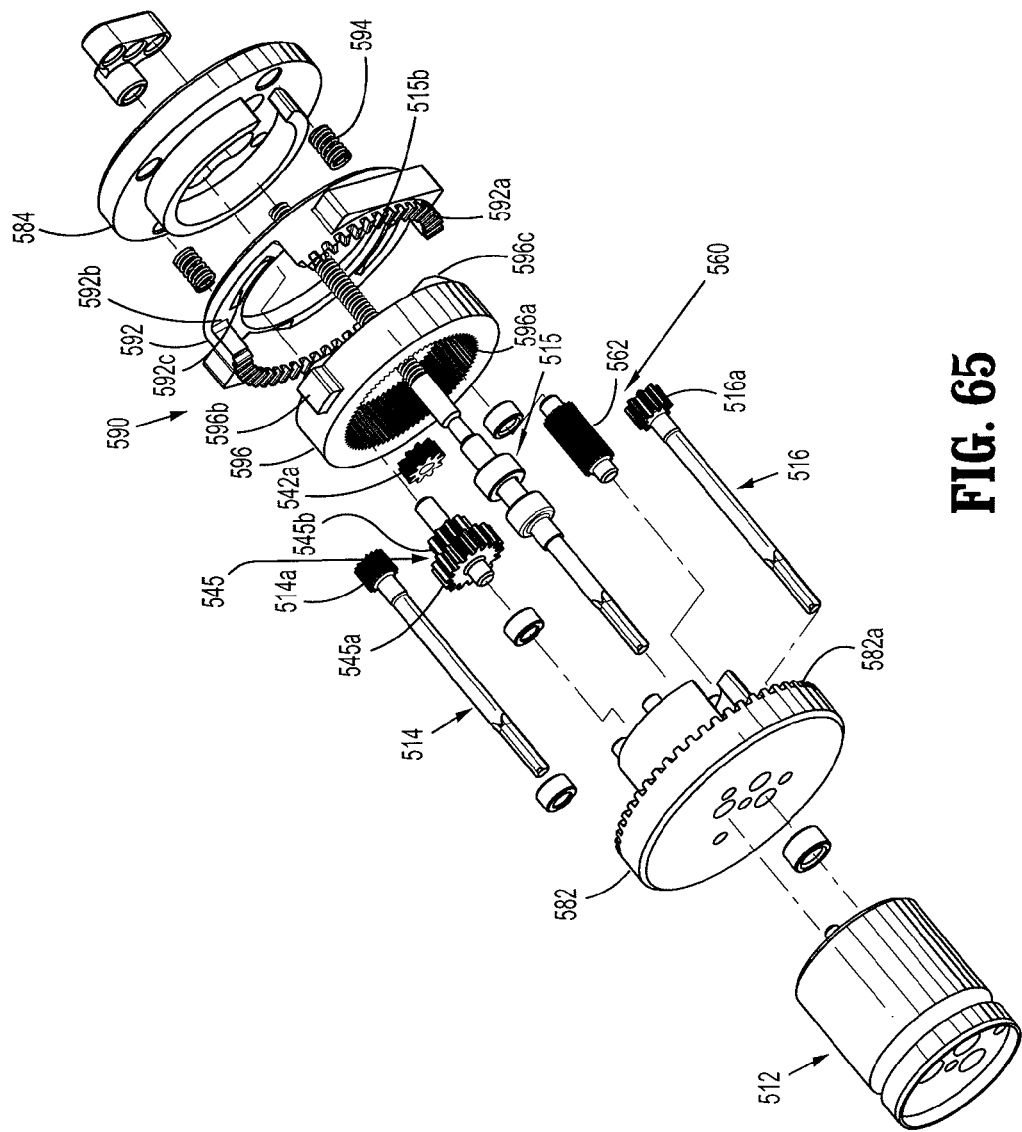
FIG. 65 is a perspective view of a clutch assembly of the adapter assembly of FIGS. 52-63.
Figure 66:
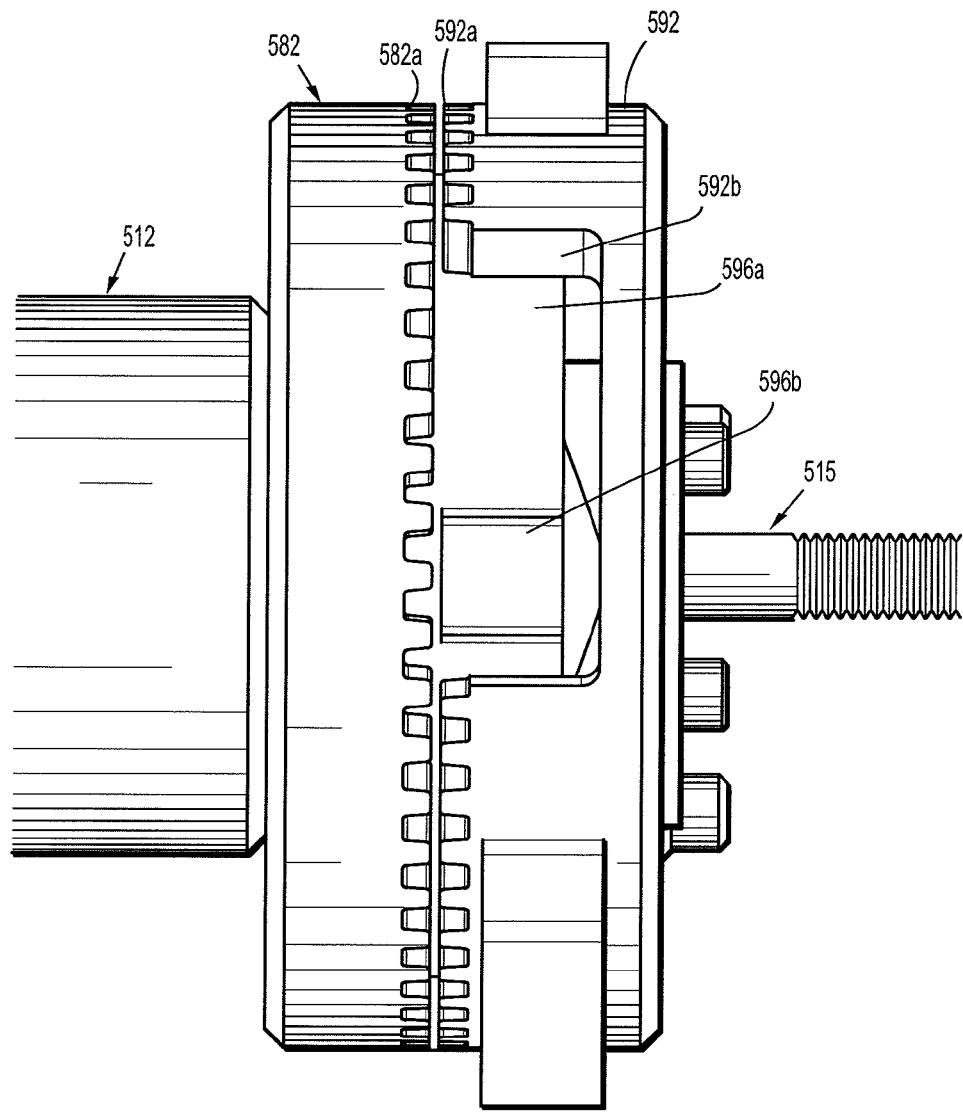
FIG. 66 is a side view of the clutch assembly of FIG. 66 shown in a disengaged condition.

As seen in FIGS. 62 and 64, adapter assembly 500 may include at least one electrical contact 576, in the form of a pin, for electrical connection to a corresponding plug of the surgical device 10.

Figure 56:
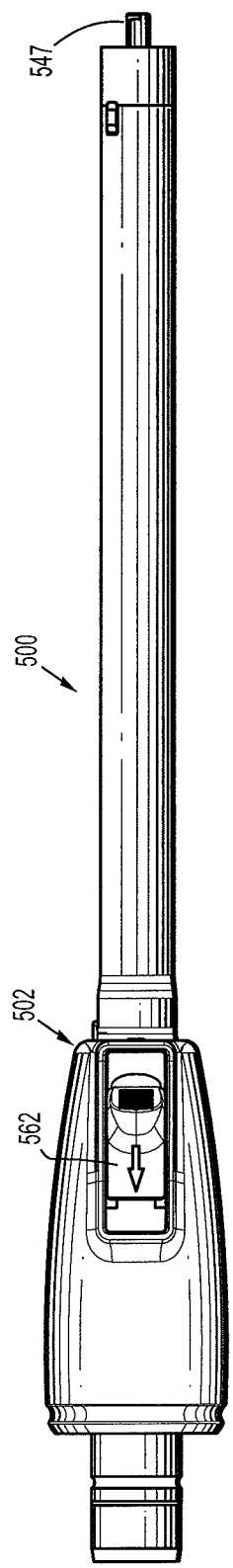
FIG. 56 is a bottom, plan view of the adapter assembly of FIGS. 52-55.
Figure 57:
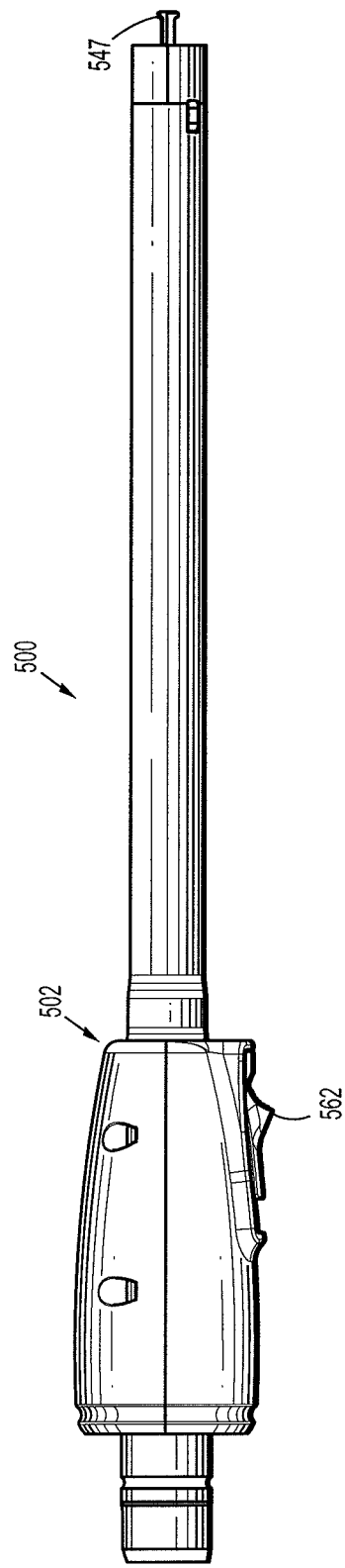
FIG. 57 is a side view of the adapter assembly of FIGS. 52-56.
Figure 58:
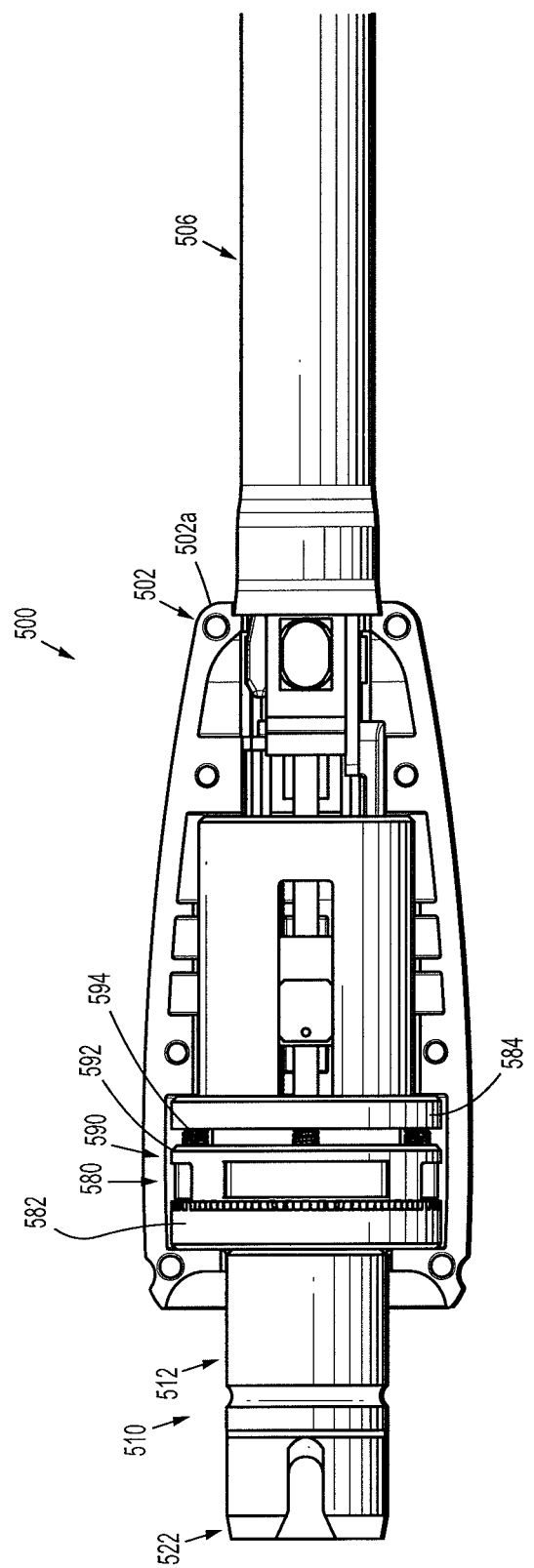
FIG. 58 is a plan view of the adapter assembly of FIGS. 52-57 with a housing half of a knob housing removed therefrom.
Figure 59:
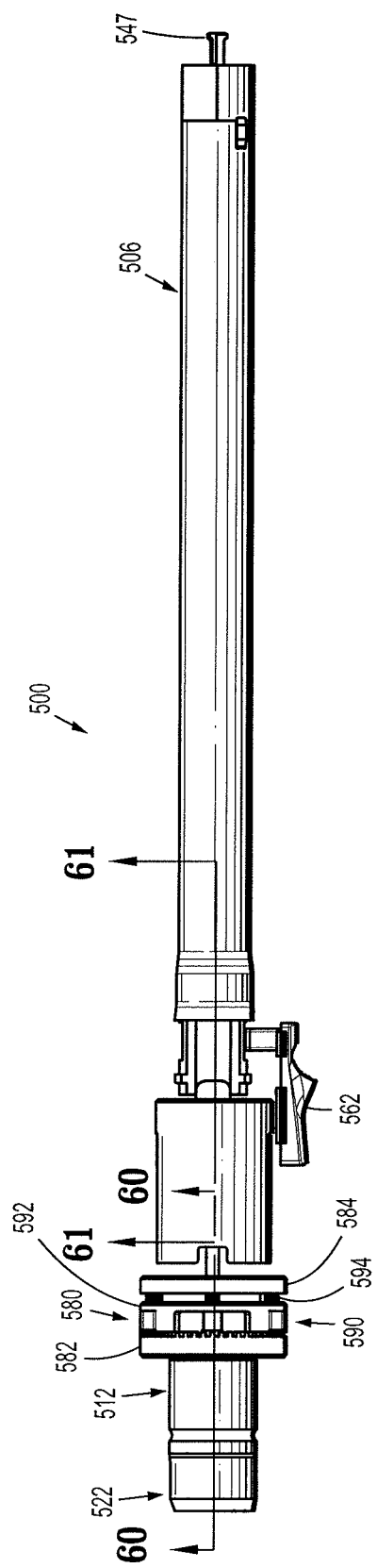
FIG. 59 is a plan view of the adapter assembly of FIGS. 52-58 with the knob housing removed therefrom.
Figure 60:
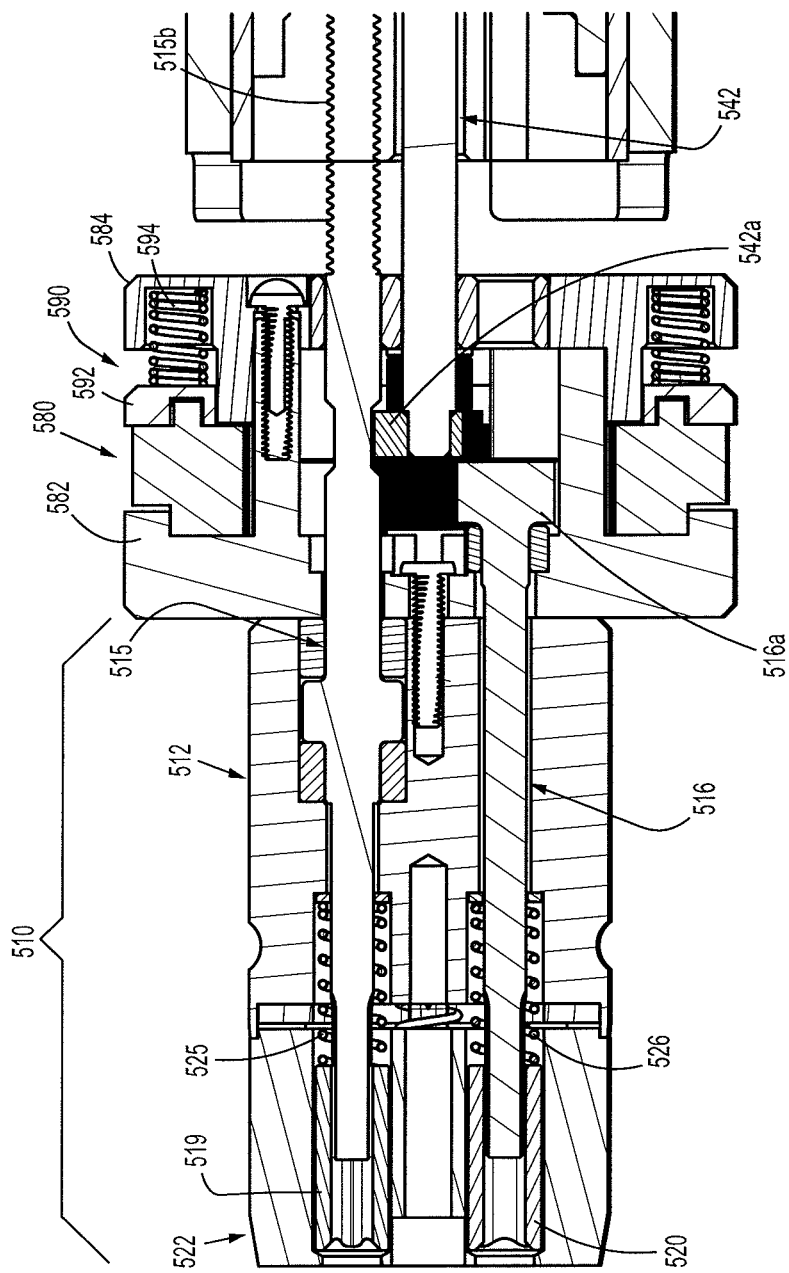
FIG. 60 is a cross-sectional view of the adapter assembly of FIGS. 52-59, as taken through 60-60 of FIG. 59.
Figure 61:
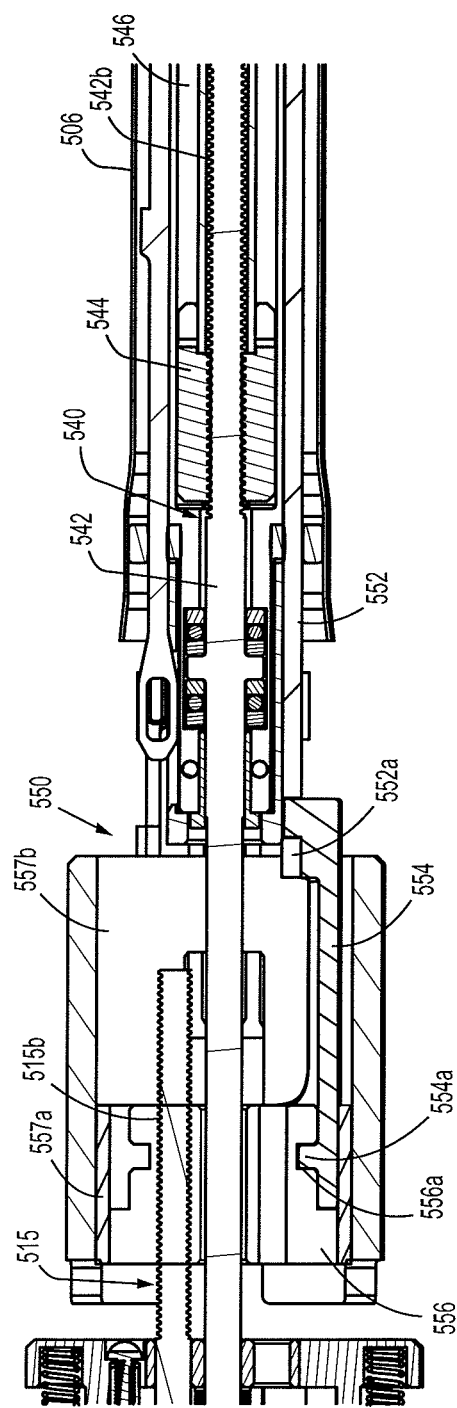
FIG. 61 is a cross-sectional view of the adapter assembly of FIGS. 52-59, as taken through 61-61 of FIG. 59.

As seen in FIGS. 56, 57 and 59, adapter assembly 500 includes a lock mechanism substantially similar to lock mechanism 160 of adapter assembly 100 and thus will only be discussed in detail herein to the extent necessary to describe differences in construction and operation thereof.

The lock mechanism of adapter assembly 500 includes a button or lever 562 slidably supported on knob housing 502 for fixing the axial position and radial orientation of drive tube 546 for the connection and disconnection of end effector 20 thereto.

Figure 67:
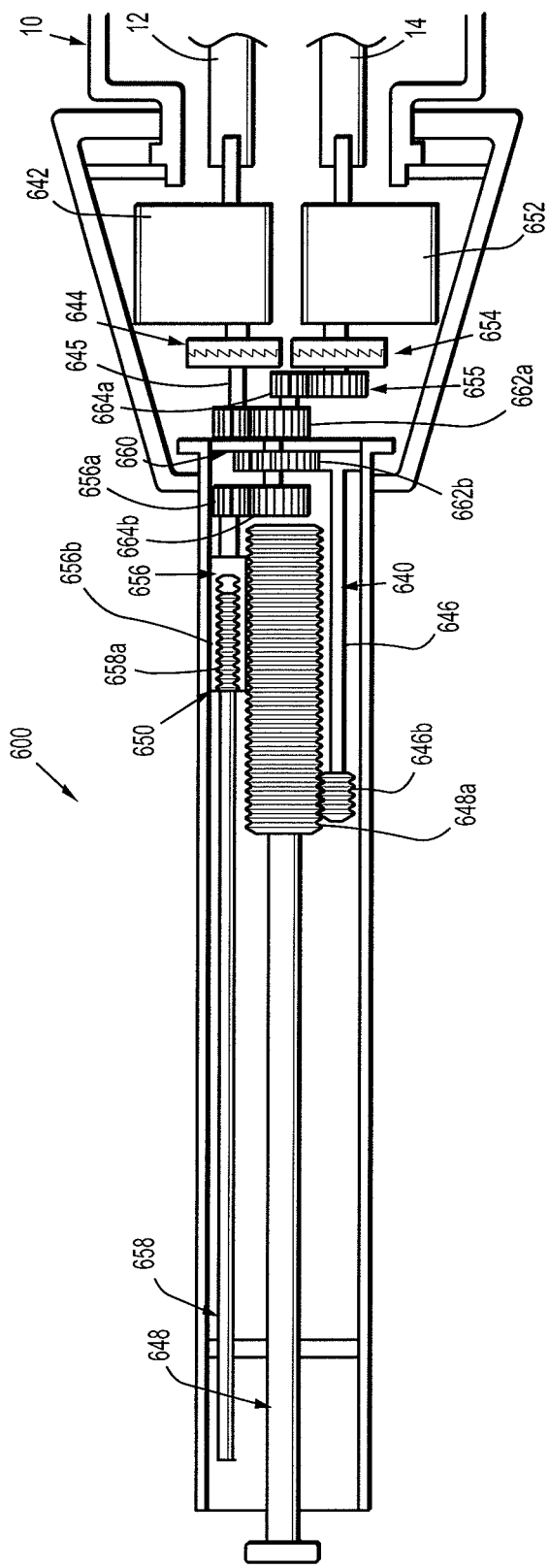
FIG. 67 is a schematic, longitudinal cross-sectional view of an adapter assembly according to another embodiment of the present disclosure.
Figure 68:
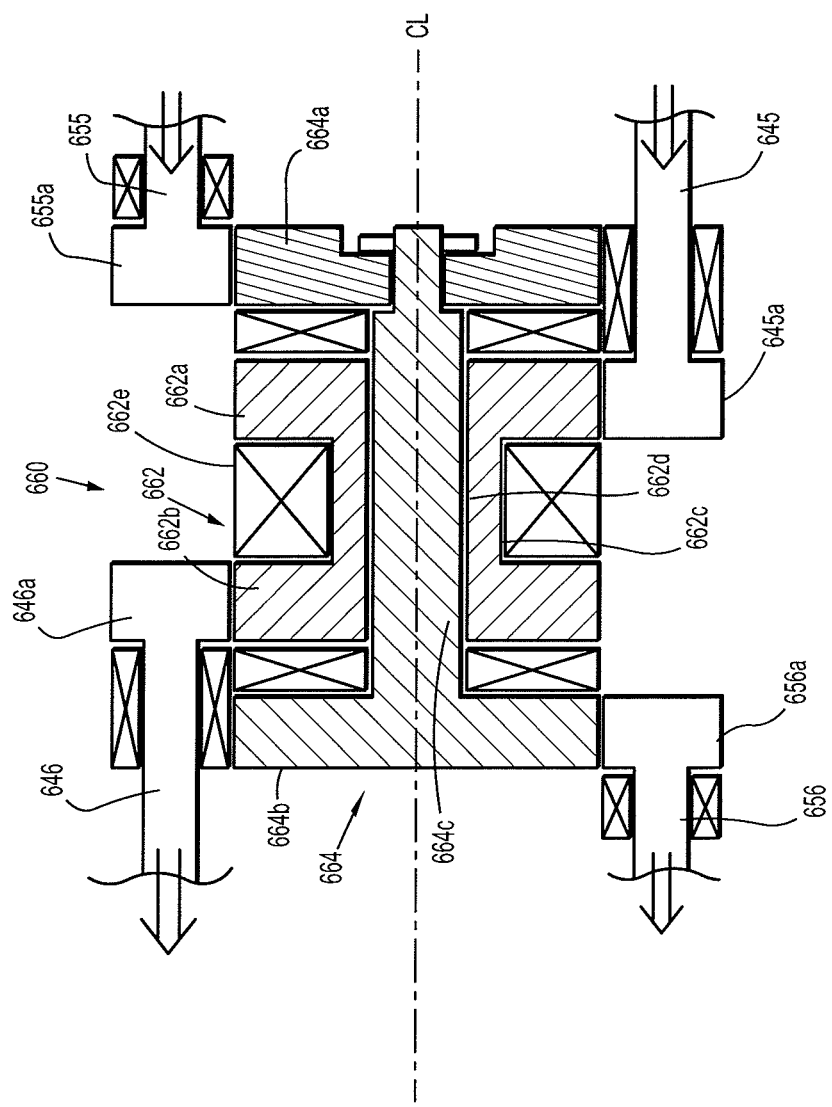
FIG. 68 is a schematic, longitudinal cross-section view of a nested gear set for use in the adapter assembly of FIG. 67.
Figure 69:
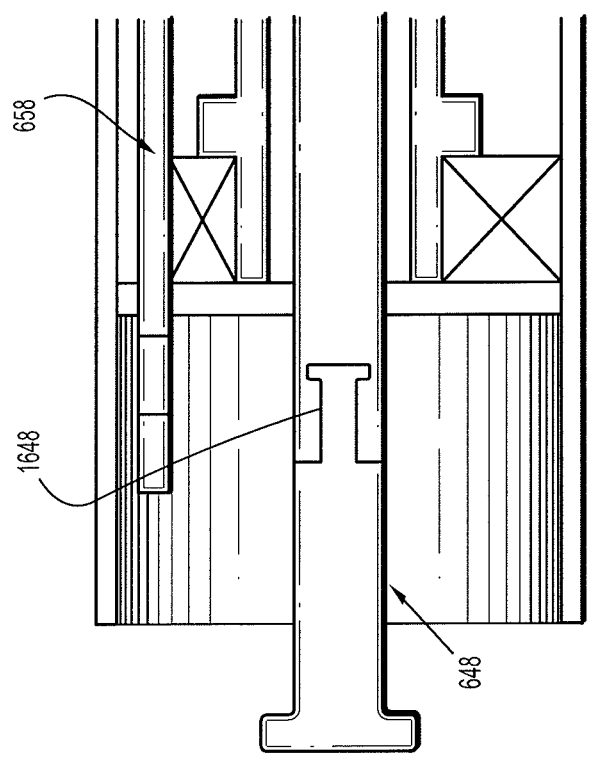
FIG. 69 is an enlarged view of the distal end of the adapter assembly shown in FIG. 67.

Turning now to FIGS. 67-69, an adapter assembly 600, in accordance with an embodiment of the present disclosure, is shown connected to or supported on a distal end of surgical device 10. As seen in FIG. 67, adapter assembly 600 includes a first and a second drive converter assembly 640, 650, respectively. Each drive converter assembly 640, 650 is configured and adapted to convert a rotation of a respective first and second drive shaft 12, 14 of surgical device 10, into axial translation of respective drive members or the like of adapter assembly 600.

As seen in FIGS. 67 and 68, adapter assembly 600 includes a nested gear set 660 having an inner gear 662 and an outer gear 664. Inner gear 662 includes a proximal spur gear 662a and a distal spur gear 662b spaced from one another along a tubular body 662c that is rotatably supported on/in a bearing 662e. Tubular body 662c defines a lumen 662d therethrough. Outer gear 664 includes a proximal spur gear 664a and a distal spur gear 664b spaced from one another along a shaft body 664c that rotatably extends through lumen 662d of inner gear 662. Proximal spur gear 664a and distal spur gear 664b of outer gear 664 are disposed proximally and distally of respective proximal spur gear 662a and distal spur gear 662b of inner gear 662.

First drive converter assembly 640 includes a proximal coupling 642 configured for selective connection to a distal end of drive shaft 12, a slip clutch system 644 connected to proximal coupling 642 and rotatably supported within a housing of adapter assembly 600, and an input drive shaft 645 supporting a spur gear 645a thereon (see FIG. 68) operatively connected to slip clutch system 644 and actuatable thereby.

First drive converter assembly 640 further includes inner gear 662 of nested gear set 660. In particular, spur gear 645a of input drive shaft 645 is engaged with proximal spur gear 662a of inner gear 662. First drive converter assembly 640 further includes an output drive shaft 646 supporting a proximal spur gear 646a that is threadably engaged with distal spur gear 662b of inner gear 662 and supporting a distal spur gear 646b that is threadably engaged with a threaded proximal end portion 648a of first drive shaft 648.

First drive shaft 648 is supported for axial reciprocation within the housing of adapter assembly. First drive shaft 648 includes a threaded proximal end portion 648a threadably coupled to distal spur gear 646b of output drive shaft 646 and a distal end portion extending from a distal end of the housing of adapter assembly 600. The distal end portion of first drive shaft 648 defines a connection member configured and adapted for selective engagement with an axially translatable drive member of any of end effectors 20, 30 and/or 40.

In operation, as inner gear 662 is rotated due to a rotation of input drive shaft 645 and first drive shaft 12 of surgical device 10, first drive shaft 648 is caused to be translated axially relative to distal spur gear 646b of output drive shaft 646. Accordingly, as first drive shaft 648 is translated axially, with the distal connection member thereof connected to a drive member of any of end effectors 20, 30 and/or 40, first drive shaft 648 causes concomitant axial translation of the drive member of any of end effectors 20, 30 and/or 40 to effectuate an operation and/or function thereof, such as, for example, the firing of the end effector or the like.

Second drive converter assembly 650 includes a proximal coupling 652 configured for selective connection to a distal end of drive shaft 14, a slip clutch system 654 connected to proximal coupling 652 and rotatably supported within a housing of adapter assembly 600, and an input drive shaft 655 supporting a spur gear 655a thereon (see FIG. 68) operatively connected to slip clutch system 654 and actuatable thereby.

Second drive converter assembly 650 further includes outer gear 664 of nested gear set 660. In particular, spur gear 655a of input drive shaft 655 is engaged with proximal spur gear 664a of outer gear 664. Second drive converter assembly 650 further includes an output drive shaft 656 supporting a proximal spur gear 656a that is threadably engaged with distal spur gear 664b of outer gear 664 and supporting a distal threaded coupling 656b that is threadably engaged with a threaded proximal end portion 658a of second drive shaft 658.

Second drive shaft 658 is supported for axial reciprocation within the housing of adapter assembly. Second drive shaft 658 includes a threaded proximal end portion 658a threadably coupled to distal threaded coupling 656b of output drive shaft 656 and a distal end portion extending to a distal end of the housing of adapter assembly 600. The distal end portion of second drive shaft 658 defines a connection member configured and adapted for selective engagement with an axially translatable drive member of any of end effectors 20, 30 and/or 40.

In operation, as outer gear 664 is rotated due to a rotation of input drive shaft 655 and second drive shaft 14 of surgical device 10, second drive shaft 658 is caused to be translated axially relative to distal threaded coupling 656b of output drive shaft 656. Accordingly, as second drive shaft 658 is translated axially, with the distal connection member thereof connected to a drive member of any of end effectors 20, 30 and/or 40, second drive shaft 658 causes concomitant axial translation of the drive member of any of end effectors 20, 30 and/or 40 to effectuate an operation and/or function thereof, such as, for example, the articulation of the end effector or the like.

It is contemplated that any of the adapter assemblies described herein may be provided with seals or the like in order to maintain the insufflation of the target site.

It is further contemplated that the outer tubes of the adapter assemblies may be provided with cut-outs or slots to provide for proper cleaning of the adapter assembly in an ultrasonic bath or the like.

In accordance with the present disclosure, it is contemplated that any of the adapter assemblies herein may include any number of lengths, may be rigid or may be flexible in nature.

It is further contemplated that any of the adapter assemblies herein may include any conductive, optical, magnetic or radio-frequency identification device that can relay information from information stored in a memory device (e.g., microchip) of the end effector through to a micro-controller or the like provided in surgical device 10. Such information can be used to determine control parameters for surgical device 10.

It is additionally contemplated that any of the end effectors, any of the adapter assemblies, and the surgical device 10 may be provided with active wireless communication features, such as, for example, ZigBee® (a specification for a suite of high level communication protocols using small, low-power digital radios based on the IEEE 802.15.4-2003 standard for wireless personal area networks (WPANs)) or Bluetooth® (an open wireless protocol for exchanging data over short distances (using short length radio waves) from fixed and mobile devices, creating personal area networks (PANs)); or by passive communication methods, such as, for example, RFiD (radio-frequency identification).

Any of the adapter assemblies herein may include an independent power source (e.g., a battery) to operate specific drives and/or to power specific sensors and/or identification electronics.

Any of the adapter assemblies may incorporate a transmission or gearing portion to optimize the rotational speed and torque or the linear speed and force to control and manipulate specific end effectors.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. An adapter assembly for selectively interconnecting a surgical end effector that is configured to perform a function and a surgical device that is configured to actuate the end effector, the end effector including at least one axially translatable drive member, and the surgical device including at least one rotatable drive shaft, the adapter assembly comprising:
   a housing configured and adapted for selective connection with the surgical device and to be in operative communication with each of the at least one rotatable drive shaft of the surgical device;
   an outer tube having a proximal end supported by the housing and a distal end configured and adapted for selective connection with the end effector, wherein the distal end of the outer tube is in operative communication with each of the at least one axially translatable drive member of the end effector;
   at least one coupling sleeve rotatably supported in the housing, the at least one coupling sleeve being configured and adapted for selective connection to the at least one rotatable drive shaft of the surgical device;
   at least one drive converter assembly for selectively interconnecting a respective one of the at least one rotatable drive shaft of the surgical device and one of the at least one axially translatable drive member of the end effector,
   wherein the at least one drive converter assembly includes:
      a first end that is releasably connectable to a first rotatable drive shaft of the surgical device and a second end that is releasably connectable to a first axially translatable drive member of the end effector;
      a hollow tube rotatably disposed within the housing and the outer tube, wherein a proximal end of the hollow tube is in operative communication with the coupling sleeve;
      a coupling nut connected to a distal end of the hollow tube; and
      an axially translatable drive shaft having a threaded proximal portion connected to the coupling nut and a distal portion configured and adapted for selective connection to the first axially translatable drive member of the end effector,
   wherein the at least one drive converter assembly converts and transmits, within the adapter assembly, a rotation of the first rotatable drive shaft of the surgical device to an axial translation of the first axially translatable drive member of the end effector,
   wherein rotation of the first rotatable drive shaft of the surgical device results in rotation of the at least one coupling sleeve, the hollow tube and the coupling nut, and wherein rotation of the coupling nut results in axial translation of the axially translatable drive shaft of the at least one drive converter assembly and of the first axially translatable drive member of the end effector.

2. The adapter assembly according to claim 1, further comprising a flexible drive cable interconnecting the at least one coupling sleeve and the hollow tube.

3. The adapter assembly according to claim 1, further comprising a lock mechanism for fixing at least one of an axial position and radial orientation of the axially translatable drive shaft of the at least one drive converter assembly.

4. The adapter assembly according to claim 1, further comprising at least one recognition sensor supported adjacent at least one of a distal end thereof and a proximal end thereof.

5. An adapter assembly for selectively interconnecting a surgical end effector that is configured to perform a function and a surgical device that is configured to actuate the end effector, the end effector including at least one axially translatable drive member, and the surgical device including at least one rotatable drive shaft, the adapter assembly comprising:
   a housing configured and adapted for selective connection with the surgical device and to be in operative communication with each of the at least one rotatable drive shaft of the surgical device;
   an outer tube having proximal end supported by the housing and a distal end configured and adapted for selective connection with the end effector, wherein the distal end of the outer tube is in operative communication with each of the at least one axially translatable drive member of the end effector;

at least one coupling sleeve rotatably supported in the housing, the at least one coupling sleeve being configured and adapted for selective connection to the at least one rotatable drive shaft of the surgical device; and at least one drive converter assembly for selectively interconnecting a respective one of the at least one rotatable drive shall of the surgical device and one of the at least one axially translatable drive member of the end effector, wherein the at least one drive converter assembly includes:
- a first end that is releasably connectable to a first rotatable drive shaft of the surgical device and a second end that is releasably connectable to a first axially translatable drive member of the end effector;
- a drive shaft rotatably disposed within the housing and the outer tube of the adapter assembly, wherein a proximal end portion of the drive shaft of the at least one drive converter assembly is in operative communication with the at least one coupling sleeve, and wherein the drive shaft of the at least one drive converter assembly includes a threaded distal end portion; and
- an axially translatable drive bar having a threaded proximal portion connected to the threaded distal portion of the drive shaft of the at least one drive converter assembly and a distal end portion configured and adapted for selective connection to the first axially translatable drive member of the end effector, wherein the at least one drive converter assembly converts and transmits, within the adapter assembly, a rotation of the first rotatable drive shaft of the surgical device to an axial translation of the first axially translatable drive member of the end effector, wherein rotation of the first rotatable drive shaft of the surgical device results in rotation of the at least one coupling sleeve and the drive shaft of the at least one drive converter assembly, and wherein rotation of the drive shaft of the at least one drive converter assembly results in axial translation of the axially translatable drive bar and the first axially translatable drive member of the end effector.

6. The adapter assembly according to claim 5, further comprising a flexible drive cable interconnecting the at least one coupling sleeve and the drive shaft of the at least one drive converter assembly.

7. An adapter assembly
for selectively interconnecting a surgical end effector that is configured to perform a function and a surgical device that is configured to actuate the end effector, the end effector including at least one axially translatable drive member, and the surgical device including at least one rotatable drive shaft, the adapter assembly comprising:

a housing configured and adapted for selective connection with the surgical device and to be in operative communication with each of the at least one rotatable drive shaft of the surgical device;

an outer tube having a proximal end supported by the housing and a distal end configured and adapted for selective connection with the end effector, wherein the distal end of the outer tube is in operative communication with each of the at least one axially translatable drive member of the end effector;

a first coupling sleeve rotatably supported in the housing, the first coupling sleeve being configured and adapted for selective connection to a first rotatable drive shaft of the surgical device;

a second coupling sleeve rotatably supported in the housing, the second coupling sleeve being configured and adapted for selective connection to a second rotatable drive shaft of the surgical device; and at least one drive converter assembly for selectively interconnecting a respective one of the at least one rotatable drive shaft of the surgical device and one of the at least one axially translatable drive member of the end effector, wherein the at least one drive converter assembly includes a first end that is releasably connectable to the first rotatable drive shaft of the surgical device and a second end that is releasably connectable to a first axially translatable drive member of the end effector, wherein the at least one drive converter assembly converts and transmits, within the adapter assembly, a rotation of the first rotatable drive shalt of the surgical device to an axial translation of the first axially translatable drive member of the end effector, wherein the at least one drive converter assembly further includes a first drive converter assembly and a second drive converter assembly;

wherein the first drive converter assembly includes:
- a hollow tube rotatably disposed within the housing and the outer tube, wherein a proximal end of the hollow tube is in operative communication with the first coupling sleeve;
- a coupling nut connected to a distal end of the hollow tube; and
- a first axially translatable drive shaft having a threaded proximal portion connected to the coupling nut and a distal portion configured and adapted for selective connection to the first axially translatable drive member of the end effector;

wherein rotation of the first rotatable drive shaft of the surgical device results in rotation of the first coupling sleeve, the hollow tube and the coupling nut, and wherein rotation of the coupling nut results in axial translation of the first axially translatable drive shaft and of the first axially translatable drive member of the end effector; and wherein the second drive converter assembly includes:
- a drive shaft rotatably disposed within the housing and the outer tube of the adapter assembly, wherein a proximal end portion of the drive shaft of the second drive converter assembly is in operative communication with the second coupling sleeve, and wherein the drive shaft of the second drive converter assembly includes a threaded distal end portion; and
- an axially translatable drive bar having a threaded proximal portion connected to the threaded distal portion of the drive shaft of the second drive converter assembly and a distal end portion configured and adapted for selective connection to a second axially translatable drive member of the end effector;

wherein rotation of the second rotatable drive shaft of the surgical device results in rotation of the second coupling sleeve and of the drive shaft of the second drive converter assembly, and wherein rotation of the drive shaft of the second drive converter assembly results in axial translation of the axially translatable drive bar and of the second axially translatable drive member of the end effector.

8. The adapter assembly according to claim 7, further comprising a first flexible drive cable interconnecting the first coupling sleeve and the hollow tube of the first drive converter assembly, and a second flexible drive cable interconnecting the second coupling sleeve and the drive shaft of the second drive converter assembly.

9. The adapter assembly according to claim 7, further comprising a lock mechanism for fixing at least one of an axial position and radial orientation of the first axially translatable drive shaft of the first drive converter assembly.

10. An adapter assembly for selectively interconnecting a surgical end effector that is configured to perform a function and a surgical device that is configured to actuate the end effector, the end effector including at least one axially translatable drive member, and the surgical device including at least one rotatable drive shaft, the adapter assembly comprising:
   a housing configured and adapted for selective connection with the surgical device and to be in operative communication with each of the at least one rotatable drive shaft of the surgical device;
   an outer tube having a proximal end supported by the housing and a distal end configured and adapted for selective connection with the end effector, wherein the distal end of the outer tube is in operative communication with each of the at least one axially translatable drive member of the end effector;
   at least one coupling sleeve rotatably supported in the housing, the at least one coupling sleeve being configured and adapted for selective connection to the at least one rotatable drive shaft of the surgical device; and
   at least one drive converter assembly for selectively interconnecting a respective one of the at least one rotatable drive shaft of the surgical device and one of the at least one axially translatable drive member of the end effector, wherein the at least one drive converter assembly includes:
      a first end that is releasably connectable to a first rotatable drive shaft of the surgical device and a second end that is releasably connectable to a first axially translatable drive member of the end effector;
      a drive shaft rotatably disposed within the housing and the outer tube, wherein a proximal end of the drive shaft of the at least one drive converter assembly is in operative communication with the at least one coupling sleeve, wherein the drive shaft of the at least one drive converter assembly has a threaded distal end portion;
      a drive coupling nut threadably connected to the threaded distal end portion of the drive shaft of the at least one drive converter assembly, wherein the drive coupling nut is inhibited from axial rotation relative to the drive shaft of the at least one drive converter assembly; and
      an axially translatable drive bar having a proximal portion connected to the drive coupling nut and a distal portion configured and adapted for selective connection to the first axially translatable drive member of the end effector,
   wherein the at least one drive converter assembly converts and transmits within the adapter assembly, a rotation of the first rotatable drive shaft of the surgical device to an axial translation of the first axially translatable drive member of the end effector,
   wherein rotation of the first rotatable drive shaft of the surgical device results in rotation of the drive shaft of the at least one drive converter assembly, and wherein rotation of the drive shaft of the at least one drive converter assembly results in axial translation of the drive coupling nut and the axially translatable drive bar that is connected thereto.

11. An adapter assembly for selectively interconnecting a surgical end effector that is configured to perform a function and a surgical device that is configured to actuate the end effector, the end effector including at least one axially translatable drive member, and the surgical device including at least one rotatable drive shaft, the adapter assembly comprising:
   a housing configured and adapted for selective connection with the surgical device and to be in operative communication with each of the at least one rotatable drive shaft of the surgical device;
   an outer tube having a proximal end supported by the housing and a distal end configured and adapted for selective connection with the en effector, wherein the distal end of the outer tube is in operative communication with each of the at least on axially translatable drive member of the end effector;
   at least one coupling sleeve rotatably supported in the housing, the at least one coupling sleeve being configured and adapted for selective connection to the at least one rotatable drive shaft of the surgical device; and
   at least one drive converter assembly for selectively interconnecting a respective one of the at least one rotatable drive shaft of the surgical device and one of the at least one axially translatable drive member of the end effector, wherein the at least one drive converter assembly includes:
      a first end that is releasably connectable to a first rotatable drive shaft of the surgical device and a second end that is releasably connectable to a first axially translatable drive member of the end effector;
      a drive shaft rotatably disposed within the housing and the outer tube, wherein a proximal end of the drive shaft of the at least one drive converter assembly is in operative communication with the at least one coupling sleeve, wherein the drive shaft of the at least one drive converter assembly has a threaded distal end portion;
      a coupling cuff threadably connected to the threaded distal end portion of the drive shaft of the at least one drive converter assembly, wherein the coupling cuff is supported for axial translation and rotation within the housing of the adapter assembly; and
      an axially translatable drive bar having a proximal portion connected to the coupling cuff and a distal portion configured and adapted for selective connection to the first axially translatable drive member of the end effector,
   wherein the at least one drive converter assembly converts and transmits, within the adapter assembly, a rotation of the first rotatable drive shaft of the surgical device to an axial translation of the first axially translatable drive member of the end effector,
   wherein rotation of the first rotatable drive shaft of the surgical device results in rotation of the drive shaft of the at least one drive converter assembly, and wherein rotation of the drive shaft of the at least one drive converter assembly results in axial translation of the coupling cuff and the axially translatable drive bar that is connected thereto.

12. The adapter assembly according to claim 11, wherein the drive shaft of the at least one drive converter assembly defines an axis of rotation, and wherein the coupling cuff defines an axis of rotation that is spaced a radial distance from the axis of rotation of the drive shaft of the at least one drive converter assembly.

13. An adapter assembly for selectively interconnecting a surgical end effector that is configured to perform a function and a surgical device that is configured to actuate the end effector, the end effector including at least one axially translatable drive member, and the surgical device including at least one rotatable drive shaft, the adapter assembly comprising:
  a housing configured and adapted for selective connection with the surgical device and to be in operative communication with each of the at least one rotatable drive shaft of the surgical device;
  an outer tube having a proximal end supported by the housing and a distal end configured and adapted for selective connection with the end effector, wherein the distal end of the outer tube is in operative communication with each of the at least one axially translatable drive member of the end effector;
  a first coupling sleeve rotatably supported in the housing, the first coupling sleeve being configured and adapted for selective connection to a first rotatable drive shaft of the surgical device;
  a second coupling sleeve rotatably supported in the housing, the second coupling sleeve being configured and adapted for selective connection to a second rotatable drive shaft of the surgical device; and
  at least one drive converter assembly for selectively interconnecting a respective one of the at least one rotatable drive shaft other surgical device and one of the at least one axially translatable drive member of the end effector,
  wherein the at least one drive converter assembly includes a first end that is releasably connectable to the first rotatable drive shaft of the surgical device and a second end that is releasably connectable to a first axially translatable drive member of the end effector,
  wherein the at least one drive converter assembly converts and transmits, within the adapter assembly, a rotation of the first rotatable drive shaft of the surgical device to an axial translation of the first axially translatable drive member of the end effector,
  wherein the at least one drive converter assembly further includes a first drive converter assembly and a second drive converter assembly;
  wherein the first drive converter assembly includes:
    a first drive shaft rotatably disposed within the housing and the outer tube, wherein a proximal end of the first drive shaft of the first drive converter assembly is in operative communication with the first coupling sleeve, wherein the first drive shaft of the first drive converter assembly has a threaded distal end portion;
    a drive coupling nut threadably connected to the distal end portion of the first drive shaft of the first drive converter assembly, wherein the drive coupling nut is inhibited from axial rotation relative to the first drive shaft of the first drive converter assembly; and
    a first axially translatable drive bar having a proximal portion connected to the drive coupling nut and a distal portion configured and adapted for selective connection to the first axially translatable drive member of the end effector, wherein rotation of the first rotatable drive shaft of the surgical device results in rotation of the first drive shaft of the first drive converter assembly, and wherein rotation of the first drive shaft of the first drive converter assembly results in axial translation of the drive coupling nut and the first axially translatable drive bar that is connected thereto; and
  wherein the second drive converter assembly includes:
    a second drive shaft rotatably disposed within the housing and the outer tube, wherein a proximal end of the second drive shaft of the second drive converter assembly is in operative communication with the second coupling sleeve, wherein the second drive shaft of the second drive converter assembly has a threaded distal end portion;
    a coupling cuff threadably connected to the threaded distal end portion of the second drive shaft of the second drive converter assembly, wherein the coupling cuff is supported for axial translation and rotation within the housing of the adapter assembly; and
    a second axially translatable drive bar having a proximal portion connected to the coupling cuff and a distal portion configured and adapted for selective connection to a second axially translatable drive member of the end effector,
  wherein rotation of the second rotatable drive shaft of the surgical device results in rotation of the second drive shaft of the second drive converter assembly, and wherein rotation of the second drive shaft of the second drive converter assembly results in axial translation of the coupling cuff and the second axially translatable drive bar that is connected thereto.

14. The adapter assembly according to claim 13, further comprising a lock mechanism for fixing at least one of an axial position and radial orientation of the first axially translatable drive shaft of the first drive converter assembly.

* * * * *